(12) United States Patent
Liang et al.

(10) Patent No.: US 9,023,809 B2
(45) Date of Patent: May 5, 2015

(54) PHENYLALANINE DIPEPTIDE DERIVATIVES, COMPOSITIONS AND USE THEREOF

(75) Inventors: Guangyi Liang, Guiyang (CN); Bixue Xu, Guiyang (CN); Changxiao Liu, Tianjin (CN); Zhengming Huang, Beijing (CN); Peixue Cao, Guiyang (CN); Zegui Cai, Guiyang (CN); Yuming Liu, Guiyang (CN)

(73) Assignees: The Key Laboratory of Chemistry For Natural Products of Guizhou Province and Chinese Academy of Sciences (CN); Tianjin Institute of Pharmaceutical Research (CN); 302 Hospital of PLA, China (CN)

( * ) Notice: Subject to any disclaimer, the term of this patent is extended or adjusted under 35 U.S.C. 154(b) by 1188 days.

(21) Appl. No.: 12/056,506

(22) Filed: Mar. 27, 2008

(65) Prior Publication Data
US 2009/0247470 A1 Oct. 1, 2009

(51) Int. Cl.
| | |
|---|---|
| A61K 38/05 | (2006.01) |
| C07K 5/06 | (2006.01) |
| C07D 295/155 | (2006.01) |
| C07C 231/02 | (2006.01) |
| C07C 233/76 | (2006.01) |
| C07C 235/32 | (2006.01) |
| C07C 237/32 | (2006.01) |
| C07D 213/81 | (2006.01) |

(52) U.S. Cl.
CPC .......... *C07D 295/155* (2013.01); *C07C 231/02* (2013.01); *C07C 233/76* (2013.01); *C07C 235/32* (2013.01); *C07C 237/32* (2013.01); *C07D 213/81* (2013.01)

(58) Field of Classification Search
CPC .................................. C07K 5/06; A61K 38/05
USPC ................................................. 514/1.1, 21.91
See application file for complete search history.

(56) References Cited

U.S. PATENT DOCUMENTS 4,025,644 A * 5/1977 Miki et al. .................... 514/486
7,056,942 B2 * 6/2006 Hildesheim et al. .......... 514/411

FOREIGN PATENT DOCUMENTS

| CN | 1437937 | | 8/2003 |
| GB | 1466498 | A | 3/1977 |
| JP | 7278080 | A | 10/1995 |
| WO | 2004024755 | A2 | 3/2004 |

OTHER PUBLICATIONS

Merrifield RB, "Solid Phase Peptide Synthesis. I. The synthesis of a Tetrapeptide," JACS, 1963, 85: 2149-2154.*

Hepatitis B from http://www.mayoclinic.com/health/hepatitis-b/ds00398/dsection=treatments-and-drugs, pp. 1-4. Accessed Jul. 22, 2009.*
HIV overview from http://www.webmd.com/hiv-aids/default.htm, pp. 1-3. Accessed Jul. 22, 2009.*
Isomer definition from http://www.answers.com/topic/isomer, pp. 1-10. Accessed Jul. 29, 2009.*
Stereoisomer definition from http://www.chemicool.com/definition/stereoisomers.html, pp. 1-3. Accessed Jul. 22, 2009.*
Tautomer definition from http://medical-dictionary.thefreedictionary.com/tautomer, pp. 1-2. Accessed Jul. 22, 209.*
Racemate definition from http://www.chemicool.com/definition/racemate.html, pp. 1-2. Accessed Jul. 23, 2009.*
Hensley S, "Zyrtec Looks in Mirror and Sees Xyzal," from http://blogs.wsj.com/health/2007/05/29/zyrtec-looks-in-mirror-and-sees-xyzal/, pp. 1-3. Accessed Jul. 29, 2009.*
More D, "Xyzal: State of the Art Antihistamine," from http://allergies.about.com/b/2007/10/09/xyzal-state-of-the-art-antihistamine.htm, p. 1. Accessed Jul. 29, 2009.*
Skingenious from http://skingenous.com/faq.html, pp. 1-7. Accessed Jul. 29, 2009.*
Vippagunta SR, Brittain HG, Grant DJW, "Crystalline Solids," Advanced Drug Delivery Reviews, 2001, 48: 3-26.*
Han H-K, "Targeted Prodrug Design to Optimize Drug Delivery," AAPS Pharmsci, 2000, 2(a): 1-11.*
Introduction to Infectious Diseases (Respiratory Viruses) from Merck manual, pp. 1-2. Accessed Oct. 6, 2009.*
Adenovirus infections from Merck manual, pp. 1-2. Accessed Oct. 6, 2009.*
Common cold from Merck manual, pp. 1-2. Accessed Oct. 6, 2009.*
Influenza from Merck manual, pp. 1-5. Accessed Oct. 6, 2009.*
Respiratory Syncytial Virus (RSV) and Human Metapneumovirus Infections from Merck manual, pp. 1-2. Accessed Oct. 6, 2009.*
Severe Acute Respiratory Syndrome (SARS) from Merck manual, pp. 1-2. Accessed Oct. 6, 2009.*

(Continued)

*Primary Examiner* — Julie Ha
(74) *Attorney, Agent, or Firm* — Schwegman Lundberg & Woessner, P.A.

(57) ABSTRACT

Disclosed are a compound of formula I, stereoisomers, pharmaceutically acceptable salts or hydrates thereof, a pharmaceutical composition comprising the same, a process for preparing the same and use thereof. The compound may also be used to prepare a medicament to treat viral infections, especially to prepare a medicament to treat hepatitis B virus and human immunodeficiency virus with little toxic side effects.

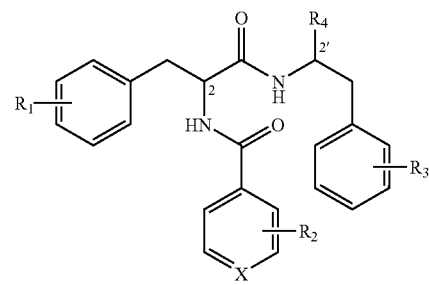

7 Claims, No Drawings

(56) References Cited

OTHER PUBLICATIONS

Introduction to Hepatitis from Merck manual, p. 1. Accessed Oct. 6, 2009.*
Acute Viral Hepatitis from Merck manual, pp. 1-9. Accessed Oct. 6, 2009.*
Introduction to HIV-1 from Merck manual, pp. 1-16. Accessed Oct. 6, 2009.*
Karposi's Sarcoma from Merck manual, pp. 1-3. Accessed Oct. 13, 2009.*
2009 H1N1 Flu ("Swine Flu") and You from CDC, pp. 1-6. Accessed Oct. 13, 2009.*
Peng J, Fan G, Wu Y, "SUpercritical fluid extraction of aurentiamide acetate from *Patrinia villosa* Juss and subsequent isolation by silica gel and high-speed counter-current chromaography," Journal of Chromatography A, 2005, 1083: 52-57.*
Wu, J-B, Chun Y-T, Ebizuka Y, Sankawa U, "Biologically Active Constituents of Centipeda Minima: Isolation of a New Plenolin Ester and the Antiallergy Activity of Sequiterpene Lactones," Chemical & Pharmaceutical Bulletin, 1985, 33(9): 4091-4094.*
Itabashi et al, "Two New Dioxopiperazine Derivatives, Arestrictins A and B, Isolated from *Aspergillus restrictus* and *Asperfillus penicilloides*," Chem. Pharm. Bull., 2006, 54(12): 1639-1641.*
Zhao, W. et al. "Isolation and Structure Determination of Aurantiamide Acetate from *Veratrum nigrum* L. var. ussuriense Nakai." China Journal of Chinese Materia Medica, 1998, vol. 23, Issue 1, pp. 41, 63.

Wang Z., et al. "A Dipeptide Isolated from *Aster tataricus* L.f," Journal of Chinese Pharmaceutical Sciences 1999, 8 (3), pp. 171-172.
He, Z. et al. "Chemical Study on *Porandra scandens*," Nat. Prod. Res. Dev. 2006, 18:238-242 (5 pgs.).
Yin, F. et al. "Study on the Constituents of Rabdosia rubescens Hemsl." Journal of China Pharmaceutical University 2003, 34(4):302-304, English abstract only.
Wang, M. et al. "The Chemical Constituents of the Marine Sponge Sigmadocia cymiformis Esper," Chinese J. of Appl. Chem., Jan. 2002, vol. 19, No. 1, pp. 1-3, English abstract only.
Zou, C. et al. "A Bioactive Amide from Roots of *Aster tartaricus*," Acta Botanica Yunnanica, 1999, vol. 21, No. 1, pp. 121-124, English abstract only.
Xie, H., et al. "Chemical constituents from *Inula cappa*," Chin. J. Nat. Med., May 2007, vol. 5, No. 3, pp. 193-196, English abstract only.
Tang, J. et al. "Aurantiamide Acetate from Stems of *Zanthoxylum Dissitum* Hemsley," Journal of Chinese Pharmaceutical Sciences 2003, vol. 12, No. 4, pp. 231-233.
Ke, P. et al. "Studies on the Chemical Constituents of *Cirsium setosum* (Willd.) MB." Sino-TCM, Apr. 2006, vol. 8, No. 4, pp. 7-9, English abstract only.
Liang, Q., et al. "Studies on the Two Dipepetides from *Elephantopus scaber*," Journal of China Pharmaceutical University, 2002, vol. 33, No. 3, pp. 178-180, English abstract only.
Zou, J., et al. "Study on chemical constituents isolated from Semiaquilegia adoxoides," Chin. Pharm. J., Apr. 2004, vol. 39, No. 4, pp. 256-257, English abstract only.

* cited by examiner

PHENYLALANINE DIPEPTIDE DERIVATIVES, COMPOSITIONS AND USE THEREOF

TECHNICAL FIELD

The present invention relates to phenylalanine dipeptide derivatives and use thereof in preventing and/or treating viral infections, especially in preventing and/or treating viral infections in which the virus is selected from hepatitis B virus and human immunodeficiency virus.

TECHNICAL BACKGROUND

Viral infections have become the major diseases threatening human health, in which infections by human immunodeficiency virus and hepatitis B virus (HBV) significantly affect human health. There are more than 400 millions people infected by chronic hepatitis B virus, of which 75% are in the Asia and Pacific region.

Unfortunately, there is no ideal method to effectively deal with viral infections heretofore.

The present inventors have isolated the compound of N-(N-benzoyl-L-phenylalanyl)-O-acetyl-L-phenylalaninol, which has an activity of anti-hepatitis B virus, from *Dichondra repens* Forst. of the ethnic Miao herbs (Chinese Patent No. 02160306.X). The present inventors synthesized a series of structurally novel phenylalanine dipeptide derivatives by modifying the structure of the compound and reconstructing the design of the compound. It was discovered that these novel compounds are excellent formulations to prevent or treat viral infections while having little toxic side effects.

SUMMARY OF THE INVENTION

In one aspect, the present invention is directed to a phenylalanine dipeptide derivative of formula I,

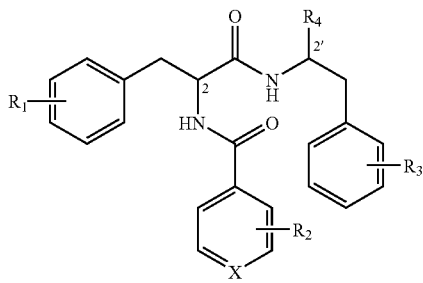

wherein,
each $R_1$, $R_2$ and $R_3$ independently represent a single substituent or multiple substituents at different positions of a ring, wherein,
$R_1$ and $R_3$ are selected from the group consisting of H, $NO_2$, $NH_2$, NRR', NHCOR, $NHCO(CH_2)_nCOOH$, OH, OCOR, OR, $O(CH_2)_nNRR'$, $O(CH_2)_nCOOR$, $O(CH_2)_nCOOH$ and $CH_2NRR'$;
$R_2$ is selected from the group consisting of H, $NO_2$, $NH_2$, NRR', NHCOR, $NHCO(CH_2)_nCOOH$, $NHOC(CH_2)_nNRR'$, OH, OCOR, OR, $O(CH_2)_nNRR'$, $O(CH_2)_nCOOH$, CN, $CH_2NRR'$, COOH, COOR, $C_1$-$C_6$ alkyl, halo,

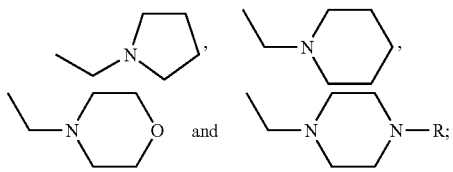

$R_4$ is selected from the group consisting of $CH_2OH$, COOR, $CH_2OCOR$, $CH_2OCO(CH_2)_nCOOH$, COONa and COOH;
each R and R' in the $R_1$ to $R_4$ described above represent identical or different, linear or branched $C_1$-$C_6$ alkyl or $C_3$-$C_7$ cycloalkyl;
said alkyl and cycloalkyl may be further optionally substituted with one or two substituents selected from the group consisting of OH, $NO_2$, CN, $CF_3$ and halo;
X is CH or N; and
n is an integral number of 1 to 4;
with the proviso that the following compounds are excluded where:
X is CH, $R_1$ is $CH_2N(CH_3)_2$, $R_2$ is H, $R_3$ is H, and $R_4$ is $CH_2OH$ or $CH_2OCOMe$;
X is CH, $R_1$ is H, $R_2$ is $NHCH_2CH_2N(CH_3)_2$, $R_3$ is H, and $R_4$ is $CH_2OH$ or $CH_2OCOMe$;
X is CH, $R_1$ is H, $R_2$ is H, $R_3$ is $CH_2N(CH_3)_2$, and $R_4$ is $CH_2OH$ or $CH_2OCOMe$; and
X is CH, each $R_1$, $R_2$ and $R_3$ are H, and $R_4$ is $CH_2ONa$;
a single stereoisomer, a mixture of stereoisomers, a racemic mixture of stereoisomers, or tautomers thereof, or pharmaceutically acceptable salts, prodrugs or solvates thereof.

In another aspect, the present invention is directed to a pharmaceutical composition, comprising a therapeutically effective amount of the compound of the present invention and a pharmaceutically acceptable carrier.

In a further aspect, the present invention is directed to a method of treating viral infections in a subject, wherein the method comprises administering to the subject a therapeutically effective amount of the compound or the pharmaceutical composition of the present invention.

In a still further aspect, the present invention is directed to a process for preparing a phenylalanine dipeptide derivative of formula I,

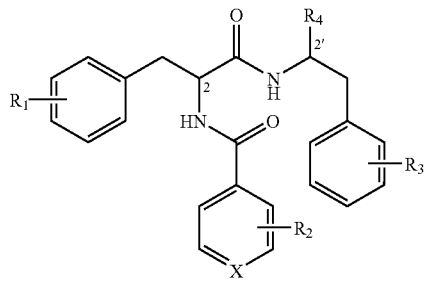

wherein,
each $R_1$, $R_2$ and $R_3$ independently represent a single substituent or multiple substituents at different positions of a ring, wherein,
$R_1$ and $R_3$ are selected from the group consisting of H, $NO_2$, $NH_2$, NRR', NHCOR, $NHCO(CH_2)_nCOOH$, OH, OCOR, OR, $O(CH_2)_nNRR'$, $O(CH_2)_nCOOR$, $O(CH_2)_n$ COOH and $CH_2NRR'$;
$R_2$ is selected from the group consisting of H, $NO_2$, $NH_2$, NRR', NHCOR, $NHCO(CH_2)_nCOOH$, $NHOC(CH_2)_n$ NRR', OH, OCOR, OR, $O(CH_2)_nNRR'$, $O(CH_2)_n$ COOH, CN, CH$_2$NRR', COOH, COOR, C$_1$-C$_6$ alkyl, halo,

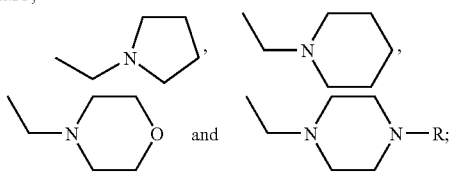

R$_4$ is selected from the group consisting of CH$_2$OH, COOR, CH$_2$OCOR, CH$_2$OCO(CH$_2$)$_n$COOH, COONa and COOH;

each R and R' in the R$_1$ to R$_4$ described above represent identical or different, linear or branched C$_1$-C$_6$ alkyl or C$_3$-C$_7$ cycloalkyl;

said alkyl and cycloalkyl may be further optionally substituted with one or two substituents selected from the group consisting of OH, NO$_2$, CN, CF$_3$ and halo;

X is CH or N; and n is an integral number of 1 to 4;

a single stereoisomer, a mixture of stereoisomers, a racemic mixture of stereoisomers, or tautomers thereof, or pharmaceutically acceptable salts, prodrugs or solvates thereof, wherein the process comprises the following steps:

i) subjecting a compound of formula I-1 to reacting with a compound of formula I-2 to obtain a compound of formula I-3,

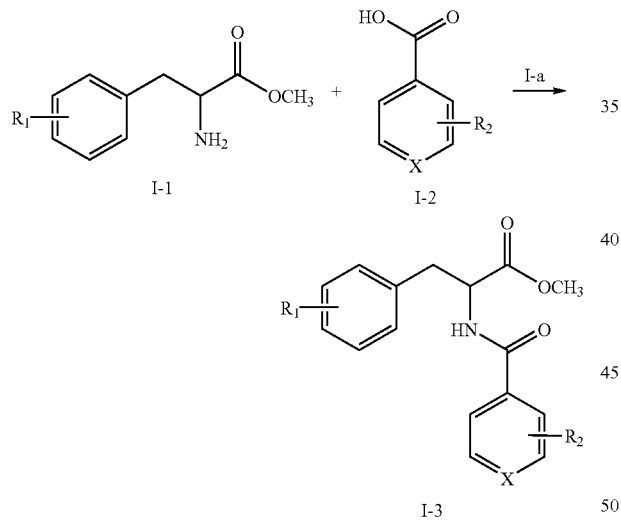

ii) converting the compound of formula I-3 into a compound of formula I-4 under basic conditions,

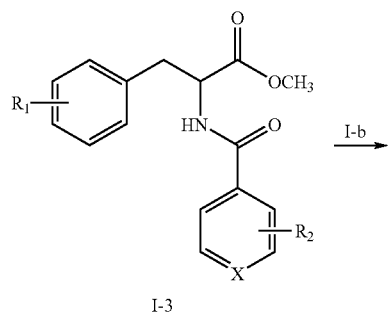

iii) subjecting the compound of formula I-4 to reacting with a compound of formula I-5 to give the target compound, wherein R$_1$, R$_2$, R$_3$ and R$_4$ in formulae I-1, I-2, I-3, I-4 and I-5 are defined as indicated above; or wherein the process comprises the following steps:

i) subjecting a compound of formula II-1 to reacting to obtain a compound of formula II-2,

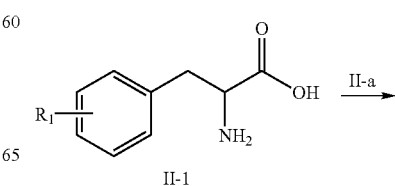

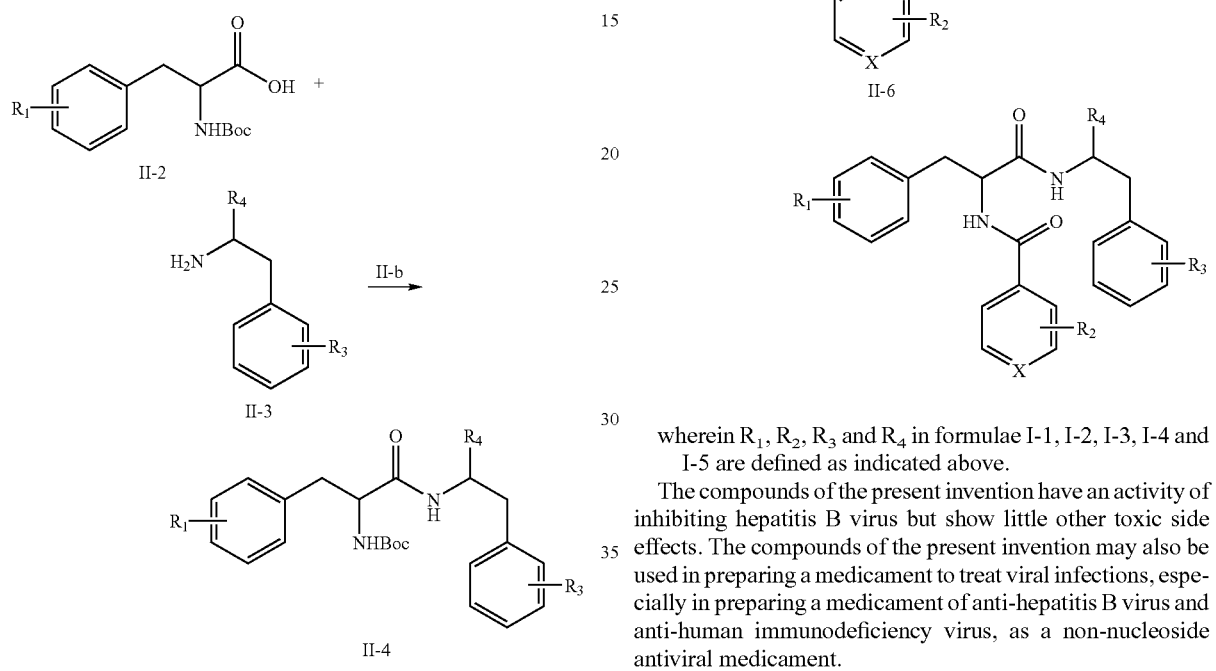

ii) subjecting the compound of formula II-2 to reacting with a compound of formula II-3 to obtain a compound of formula II-4, iii) hydrolyzing the compound of formula II-4 to obtain a compound of formula II-5 under acidic conditions, iv) subjecting the compound of formula II-5 to reacting with a compound of formula II-6 to give the target compound,

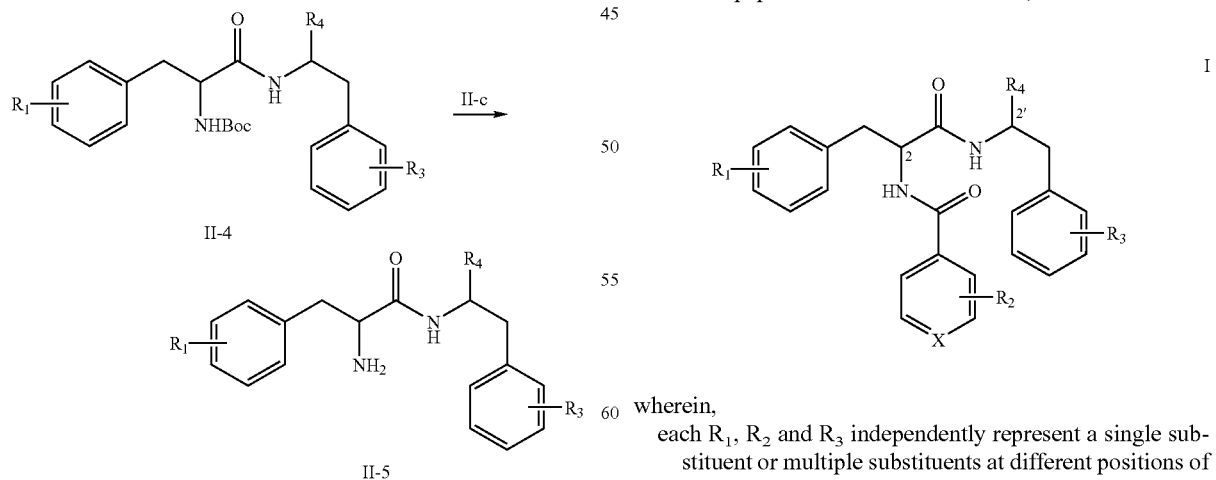

wherein $R_1$, $R_2$, $R_3$ and $R_4$ in formulae I-1, I-2, I-3, I-4 and I-5 are defined as indicated above.

The compounds of the present invention have an activity of inhibiting hepatitis B virus but show little other toxic side effects. The compounds of the present invention may also be used in preparing a medicament to treat viral infections, especially in preparing a medicament of anti-hepatitis B virus and anti-human immunodeficiency virus, as a non-nucleoside antiviral medicament.

DETAILED DESCRIPTION OF THE INVENTION

In one aspect, the present invention is directed to a phenylalanine dipeptide derivative of formula I, wherein,
each $R_1$, $R_2$ and $R_3$ independently represent a single substituent or multiple substituents at different positions of a ring, wherein,
$R_1$ and $R_3$ are selected from the group consisting of H, $NO_2$, $NH_2$, NRR', NHCOR, $NHCO(CH_2)_n COOH$, OH, OCOR, OR, $O(CH_2)_n NRR'$, $O(CH_2)_n COOR$, $O(CH_2)_n COOH$ and $CH_2 NRR'$;

$R_2$ is selected from the group consisting of H, $NO_2$, $NH_2$, NRR', NHCOR, $NHCO(CH_2)_n COOH$, $NHOC(CH_2)_n NRR'$, OH, OCOR, OR, $O(CH_2)_n NRR'$, $O(CH_2)_n COOH$, CN, $CH_2NRR'$, COOH, COOR, $C_1$-$C_6$ alkyl, halo,

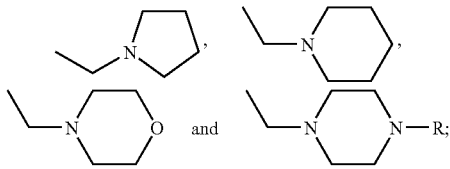

$R_4$ is selected from the group consisting of $CH_2OH$, COOR, $CH_2OCOR$, $CH_2OCO(CH_2)_n COOH$, COONa and COOH;

each R and R' represent identical or different, linear or branched $C_1$-$C_6$ alkyl or $C_3$-$C_7$ cycloalkyl;

said alkyl and cycloalkyl may be further optionally substituted with one or two substituents selected from the group consisting of OH, $NO_2$, CN, $CF_3$ and halo;

X is CH or N; and n is an integral number of 1 to 4;

with the proviso that the following compounds are excluded where:

X is CH, $R_1$ is $CH_2N(CH_3)_2$, $R_2$ is H, $R_3$ is H, and $R_4$ is $CH_2OH$ or $CH_2OCOMe$;

X is CH, $R_1$ is H, $R_2$ is $NHCH_2CH_2N(CH_3)_2$, $R_3$ is H, and $R_4$ is $CH_2OH$ or $CH_2OCOMe$;

X is CH, $R_1$ is H, $R_2$ is H, $R_3$ is $CH_2N(CH_3)_2$, and $R_4$ is $CH_2OH$ or $CH_2OCOMe$; and X is CH, each $R_1$, $R_2$ and $R_3$ are H, and $R_4$ is $CH_2ONa$;

a single stereoisomer, a mixture of stereoisomers, a racemic mixture of stereoisomers, or tautomers thereof, or pharmaceutically acceptable salts, prodrugs or solvates thereof.

In some embodiments, the stereoisomers include (2S, 2'S), (2S, 2'R), (2R, 2'S), (2R, 2'R) isomers of the phenylalanine dipeptide derivatives, a racemic mixture of the isomers and any mixtures of the isomers.

As used herein, the term "the compound(s) of the present invention" includes the phenylalanine dipeptide derivatives, a single stereoisomer thereof, a mixture of stereoisomers, a racemic mixture of stereoisomers, or tautomers thereof, or pharmaceutically acceptable salts, prodrugs or solvates thereof.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

The term "prodrug" is also meant to include any covalently bonded carriers which release the active compounds of the invention in vivo when such a prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein hydroxy, amino or mercapto group is bonded to any group that, when the prodrug of the compound of the invention is administered to a mammalian subject, cleaves to form free hydroxy, free amino or free mercapto group, respectively. Examples of prodrugs include, but are not limited to, ester or amide derivatives, or the like, of alcohol, carbonyl, mercapto, or amino functional groups in the compounds of the invention.

The term "prodrug ester" refers to derivatives of the compounds disclosed herein formed by the addition of any of several ester-forming groups that are hydrolyzed under physiological conditions. Examples of prodrug ester groups include pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of prodrug ester groups can be found in, for example, T. Higuchi and V. Stella, in "*Prodrugs as Novel Delivery Systems*", Vol. 14, A.C.S. Symposium Series, American Chemical Society (1975); and "*Bioreversible Carriers in Drug Design: Theory and Application*", edited by E. B. Roche, Pergamon Press: New York, 14-21 (1987) (providing examples of esters useful as prodrugs for compounds containing carboxyl groups). Each of the above-mentioned references is herein incorporated by reference in their entirety.

The term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

In an embodiment of the present invention, the compounds of the present invention can be used alone, in combination with other compounds described herein, or in combination with one or more other active agents in the therapeutic areas described herein.

The active agents that can be used in the present invention include, but are not limited to, antivirals, immunomodulators, anti-infectives, and the like.

In some embodiments, exemplary antivirals include, but are not limited to, amprenavir, abacavir, acemannan, acyclovir, AD-439, AD-519, adefovir dipivoxil, AL-721, alpha interferon, ansamycin LM427, antibody which neutralizes pH labile alpha aberrant interferon, AR177, beta-fluoro-ddA, BMS-232623 (CGP-73547), BMS-234475 (CGP-61755), cidofovir, curdlan sulfate, cytomegalovirus immune globin, cytovene ganciclovir, delaviridine, dextran sulfate, ddC dideoxycytidine, ddl dideoxyinosine, DMP-450, efavirenz, EL10, famciclovir, FTC, GS 840, HBY097, hypericin, recombinant human interferon beta, interferon alfa-n3 indinavir, ISIS 2922, KNI-272, lamivudine, 3TC, lobucavir, nelfinavir, nevirapine, novapren, peptide T octapeptide sequence, trisodium phosphonoformate, PNU-140690, probucol, RBC-CD4, ritonavir, saquinavir, stavudine, valaciclovir, virazole, ribavirin, VX-478, zalcitabine, zidovudine; AZT, tenofovir disoproxil fumarate salt, Emtriva® (Emtricitabine), Combivir®, abacavir succinate (Ziagen®), Reyataz® (atazanavir), Fuzeon® (T-20), Lexiva® (fosamprenavir calcium), maraviroc (UK 427857), Trizivir®, PA-457, Sch-417690 (vicriviroc), TAK-652, GSK 873140 (ONO-4128), BMS-707035, integrase inhibitor MK-0518, Truvada®, integrase inhibitor GS917/JTK-303, triple drug combination (Viread®, Emtriva®, Sustiva®) and the like.

In some embodiments, exemplary immunomodulators include, but are not limited to, AS-101, bropirimine, acemannan, CL246,738, FP-21399, gamma interferon, granulocyte macrophage colony stimulating factor, HIV core particle immunostimulant, interleukin-2, immune globulin, IMREG-1, IMREG-2, imuthiol diethyl dithio carbamate, alpha-2 interferon, methionine-enkephalin, MTP-PE, granulocyte colony stimulating factor, remune, rCD4, rCD4-IgG interferon alfa 2a, SK&F106528 soluble T4, thymopentin, tumor necrosis factor and the like.

In some embodiments, exemplary anti-infectives include, but are not limited to, clindamycin with primaquine, fluconazole, pastille nystatin, ornidyl eflornithine, pentamidine isethionate (IM & IV), trimethoprim, trimethoprim/sulfa, piritrexim pentamidine isethionate for inhalation, spiramycin, intraconazole-R51211, trimetrexate, daunorubicin, recombinant human erythropoietin, recombinant human growth hormone, megestrol acetate, testosterone, total enteral nutrition and the like.

The term "halo" refers to fluoro, chloro, bromo or iodo, with fluoro and chloro being presently preferred.

The term "alkyl", as used herein, means any unbranched or branched, substituted or unsubstituted, saturated hydrocarbon. The alkyl moiety may be branched, linear, or cyclic. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 5 carbon atoms. The alkyl group may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl.

The alkyl group may be substituted or unsubstituted. When substituted, the substituent group(s) is(are) one or more group(s) individually and independently selected from substituted or unsubstituted cycloalkyl, substituted or unsubstituted cylcloalkenyl, substituted or unsubstituted aryl, substituted or unsubstituted heteroaryl, substituted or unsubstituted heteroaryloxy, heterocyclyl, heterocyclooxy, heteroalicyclyl, hydroxy, substituted or unsubstituted alkoxy, substituted or unsubstituted aryloxy, acyl, thiol, substituted or unsubstituted thioalkoxy, alkylthio, arylthio, cyano, halo, carbonyl, thiocarbonyl, acylalkyl, acylamino, acyloxy, aminoacyl, aminoacyloxy, oxyacylamino, keto, thioketo, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and substituted or unsubstituted amino, including mono- and di-substituted amino groups, and the protected derivatives thereof, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. Wherever a substituent is described as being "optionally substituted" that substitutent may be substituted with one of the above substituents.

In the present context, the term "cycloalkyl" is intended to cover three-, four-, five-, six-, seven-, and eight- or more membered rings comprising carbon atoms only. A cycloalkyl can optionally contain one or more unsaturated bonds situated in such a way, however, that an aromatic pi-electron system does not arise. Some examples of "cycloalkyl" are the carbocycles cyclopropane, cyclobutane, cyclopentane, cyclopentene, cyclopentadiene, cyclohexane, cyclohexene, 1,3-cyclohexadiene, 1,4-cyclohexadiene, cycloheptane, or cycloheptene.

Unless otherwise indicated, when a substituent is deemed to be "optionally substituted", it is meant that the substituent is a group that may be substituted with one or more groups individually and independently selected from morpholinoalkanoate, cycloalkyl, aryl, heteroaryl, heterocyclyl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. The protecting groups that may form the protective derivatives of the above substituents are known to those of skill in the art and may be found in references such as Greene and Wuts, *Protective Groups in Organic Synthesis*, 3$^{rd}$ Ed., John Wiley & Sons, New York, N.Y. 1999.

In some embodiments, $R_1$ and $R_3$ in the compounds of formula I are independently selected from the group consisting of H, $NO_2$, $NH_2$, NRR', NHCOR, NHCO($CH_2)_n$COOH, OH, OCOR, OR and O($CH_2)_n$NRR'.

In some embodiments, $R_2$ in the compounds of formula I is selected from the group consisting of $NO_2$, NHCOR, NHCO($CH_2)_n$COOH, OH, OCOR, O($CH_2)_n$NRR', $CH_2$NRR', $C_1$-$C_6$ alkyl, halo,

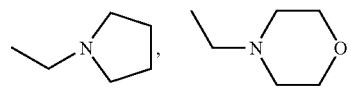

and COOH.

In some embodiments, $R_4$ in the compounds of formula I is selected from the group consisting of $CH_2OH$, COOR, $CH_2$OCOR, $CH_2$OCO($CH_2)_n$COOH, COONa and COOH.

In some preferred embodiments, $R_1$ in the compounds of formula I is selected from the group consisting of H, $NO_2$, $NHCOCH_3$, $NHCOCH_2CH_3$, $N(CH_3)_2$, $NHCO(CH_2)_2$COOH, OH, $OCH_3$, $OCOCH_3$, $O(CH_2)_2N(CH_3)_2$ and $OCH_2$COOH.

In some preferred embodiments, $R_3$ in the compounds of formula I is selected from the group consisting of H, $NO_2$, $NHCOCH_3$, $NHCOCH_2CH_3$, OH, $OCOCH_3$, $OCH_3$, $OCH_2CH_3$ and $O(CH_2)_3CH_3$.

In some preferred embodiments, $R_2$ in the compounds of formula I is selected from the group consisting of H, F, Cl, $NO_2$, $NHCOCH_3$, $NHCOCH_2Cl$, $NHCOCH_2CH_3$, NHCO($CH_2)_2$COOH, $NHCOCH_2N(CH_3)_2$, OH, $OCOCH_2CH_3$, $O(CH_2)_2N(CH_3)_2$, $CH_3$, $CH_2N(CH_3)_2$, COOH, (1-pyrrolidyl)acetamido,

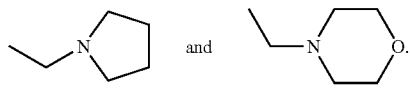

In some preferred embodiments, $R_4$ in the compounds of formula I is selected from the group consisting of $CH_2OH$, $COOCH_3$, $CH_2OCOCH_3$, $CH_2OCOCH_2CH_3$, $CH_2OCOCH_2COOH$, $CH_2OCO(CH_2)_2COOH$, COONa and COOH.

In some more preferred embodiments, the compounds of formula I are selected from the group consisting of:
methyl N-(N-benzoyl-L-phenylalanyl)-L-phenylalaninate;
N-(N-benzoyl-L-phenylalanyl)-L-phenylalaninol;
methyl N-(N-4-fluoro-benzoyl-L-phenylalanyl)-L-phenylalaninate;
methyl N-(N-benzoyl-L-phenylalanyl)-L-tyrosinate;
N-(N-3-methyl-benzoyl-L-phenylalanyl)-L-phenylalaninol;
N-(N-benzoyl-4-nitro-L-phenylalanyl)-L-phenylalaninol;
N-(N-4-chloro-benzoyl-L-phenylalanyl)-L-phenylalaninol;
N-(N-2-chloro-benzoyl-L-phenylalanyl)-L-phenylalaninol;
methyl N-(N-3-methyl-benzoyl-L-phenylalanyl)-L-phenylalaninate;
methyl N-(N-2-chloro-benzoyl-L-phenylalanyl)-L-phenylalaninate;
methyl N-(N-2-chloro-benzoyl-L-phenylalanyl)-L-tyrosinate;
methyl N-(N-benzoyl-4-nitro-L-phenylalanyl)-L-phenylalaninate;
N-(N-4-methyl-benzoyl-L-phenylalanyl)-L-phenylalaninol;
methyl N-(N-benzoyl-4-nitro-L-phenylalanyl)-L-tyrosinate;
methyl N-(N-benzoyl-4-nitro-L-phenylalanyl)-4-nitro-L-phenylalaninate;
N-(N-benzoyl-L-phenylalanyl)-4-nitro-L-phenylalaninol;
methyl N-(N-4-methyl-benzoyl-L-phenylalanyl)-L-tyrosinate;
methyl N-(N-4-methyl-benzoyl-4-nitro-L-phenylalanyl)-L-tyrosinate;
N-(N-4-chloro-benzoyl-L-tyrosyl)-L-phenylalaninol;
methyl N-(N-4-chloro-benzoyl-L-tyrosyl)-L-phenylalaninate;
N-(N-benzoyl-L-tyrosyl)-L-phenylalaninol;
N-(N-2-chloro-benzoyl-L-tyrosyl)-L-phenylalaninol;
methyl N-(N-2-chloro-benzoyl-L-tyrosyl)-L-phenylalaninate;
N-(N-4-fluoro-benzoyl-L-tyrosyl)-L-phenylalaninol;
methyl N-(N-4-fluoro-benzoyl-L-tyrosyl)-L-phenylalaninate;
N-(N-4-methyl-benzoyl-L-tyrosyl)-L-phenylalaninol;
N-(N-4-hydroxyl-benzoyl-L-phenylalanyl)-L-phenylalaninol;
methyl N-(N-4-hydroxyl-benzoyl-L-phenylalanyl)-L-phenylalaninate;
methyl N-(N-benzoyl-3-nitro-L-tyrosyl)-L-phenylalaninate;
methyl N-(N-4-nitro-benzoyl-L-tyrosyl)-L-phenylalaninate;
methyl N-(N-4-methyl-benzoyl-L-tyrosyl)-L-phenylalaninate;
N-(N-3-nitro-benzoyl-L-tyrosyl)-L-phenylalaninol;
methyl N-(N-benzoyl-L-tyrosyl)-L-phenylalaninate;
methyl N-[N-(4-acetamido-benzoyl)-L-phenylalanyl]-L-phenylalaninate;
N-[N-(4-chloroacetamido-benzoyl)-L-phenylalanyl]-L-phenylalaninol;
methyl N-[N-(4-acetamido-benzoyl)-L-phenylalanyl]-L-tyrosinate;
methyl N-[N-(4-propionamido-benzoyl)-L-phenylalanyl]-L-phenylalaninate;
methyl N-[N-(4-propionamido-benzoyl)-L-phenylalanyl]-4-nitro-L-phenylalaninate;
N-[N-(4-acetamido-benzoyl)-L-phenylalanyl]-L-phenylalaninol;
N-[N-(4-acetamido-benzoyl)-L-tyrosyl]-L-phenylalaninol;
methyl N-[N-(4-acetamido-benzoyl)-L-tyrosyl]-L-phenylalaninate;
methyl N-[N-(4-chloroacetamido-benzoyl)-L-phenylalanyl]-L-phenylalaninate;

N-(N-isonicotinyl-L-phenylalanyl)-L-phenylalaninol;
methyl N-(N-isonicotinyl-L-phenylalanyl)-L-phenylalaninate;
methyl N-(N-isonicotinyl-L-phenylalanyl)-4-nitro-L-phenylalaninate;
methyl N-(N-isonicotinyl-L-phenylalanyl)-L-tyrosinate;
N-(N-isonicotinyl-L-tyrosyl)-L-phenylalaninol;
methyl N-(N-isonicotinyl-L-tyrosyl)-L-phenylalaninate;
N-[N-(4-dimethylaminomethyl-benzoyl)-L-phenylalanyl]-L-phenylalaninol;
N-{N-[4-(1-pyrrolidyl)methyl-benzoyl]-L-phenylalanyl}-L-phenylalaninol;
N-{N-[4-(4-morpholinyl)methyl-benzoyl]-L-phenylalanyl}-L-phenylalaninol;
N-[N-(4-ethoxycarbonyl-benzoyl)-L-phenylalanyl]-L-phenylalaninol;
N-[N-(2-carboxyl-benzoyl)-4-acetamido-L-phenylalanyl]-L-phenylalaninol sodium salt;
N-(N-benzoyl-4-acetamido-L-phenylalanyl)-O-acetyl-L-phenylalaninol;
N-(N-benzoyl-L-phenylalanyl)-O-acetyl-L-phenylalaninol;
N-(N-benzoyl-L-phenylalanyl)-O-(3-carboxyl-propionyl)-L-phenylalaninol;
methyl N-(N-benzoyl-acetyl-L-phenylalanyl)-L-phenylalaninate;
methyl N-(N-benzoyl-L-phenylalanyl)-4-amino-L-phenylalaninate hydrochloride;
methyl N-(N-benzoyl-L-phenylalanyl)-4-acetamido-L-phenylalaninate;
methyl N-[N-(4-methyl-benzoyl)-L-phenylalanyl]-4-acetamido-L-phenylalaninate;
N-{N-[4-(3-carboxyl-propionamido)-benzoyl]-L-phenylalanyl}-L-phenylalaninol;
methyl N-{N-[4-(3-carboxyl-propionamido)-benzoyl]-L-phenylalanyl}-L-phenylalaninate;
methyl N-(N-benzoyl-O-acetyl-3-acetamido-L-tyrosyl)-L-phenylalaninate;
methyl N-(N-benzoyl-L-phenylalanyl)-4-propionamido-L-phenylalaninate;
N-[N-(4-dimethylaminomethyl-benzoyl)-L-phenylalanyl]-O-acetyl-L-phenylalaninol;
N-[N-(4-dimethylaminomethyl-benzoyl)-L-phenylalanyl]-O-propionyl-L-phenylalaninol;
N-{N-[4-(4-morpholinyl)methyl-benzoyl]-L-phenylalanyl}-O-propionyl-L-phenylalaninol;
methyl N-[N-(4-methyl-benzoyl)-4-acetamido-L-phenylalanyl]-O-acetyl-L-tyrosinate;
N-(N-benzoyl-L-phenylalanyl)-4-acetyl-L-phenylalaninol;
methyl N-[N-(4-chloro-benzoyl)-4-propionamido-L-phenylalanyl]-L-phenylalaninate;
methyl N-(N-benzoyl-L-phenylalanyl)-O-methyl-L-tyrosinate;
methyl N-(N-benzoyl-L-phenylalanyl)-O-n-butyl-L-tyrosinate;
N-(N-benzoyl-L-phenylalanyl)-O-ethyl-L-tyrosine;
N-(N-benzoyl-L-phenylalanyl)-O-n-butyl-L-tyrosine sodium salt;
N-[N-benzoyl-O-(2-dimethylamino-ethyl)-L-tyrosyl]-L-phenylalaninol hydrochloride;
N-[N-4-(dimethylamino-acetamido)-benzoyl-L-phenylalanyl]-L-phenylalaninol;
N-[N-4-(2-dimethylamino-ethoxyl)-benzoyl-L-phenylalanyl]-L-phenylalaninol;
methyl N-[N-4-(2-dimethylamino-ethoxyl)-benzoyl-L-phenylalanyl]-L-phenylalaninate;
N-(N-benzoyl-L-phenylalanyl)-O-methyl-L-tyrosine sodium salt;
N-[N-benzoyl-O-hydroxymethyl-L-tyrosyl]-L-phenylalaninol sodium salt;
methyl N-[N-4-(dimethylamino-acetamido)-benzoyl-L-phenylalanyl]-L-phenylalaninate;
methyl N-{N-[4-(1-pyrrolidyl)acetamido-benzoyl]-L-phenylalanyl}-L-phenylalaninate;
N-[N-benzoyl-4-(3-carboxyl-propionamido)-L-phenylalanyl]-L-phenylalaninol;
N-(N-benzoyl-4-dimethylamino-L-phenylalanyl)-L-phenylalaninol;
N-(N-benzoyl-L-phenylalanyl)-L-tyrosine and sodium salt thereof;
N-(N-benzoyl-L-phenylalanyl)-L-phenylalanine;
N-(N-benzoyl-4-acetamido-L-phenylalanyl)-L-phenylalanine;
N-(N-benzoyl-4-nitro-L-phenylalanyl)-L-phenylalanine;
N-(N-benzoyl-L-phenylalanyl)-4-acetamido-L-phenylalanine;
N-(N-4-methyl-benzoyl-L-phenylalanyl)-4-acetamido-L-phenylalanine;
N-(N-4-hydroxyl-benzoyl-L-phenylalanyl)-L-phenylalanine sodium salt;
N-[N-4-(3-carboxyl-propionamido)-benzoyl-L-phenylalanyl]-L-phenylalanine sodium salt;
N-(N-benzoyl-L-tyrosyl)-L-phenylalanine;
N-(N-benzoyl-L-phenylalanyl)-4-propionamido-L-phenylalanine;
N-(N-benzoyl-L-tyrosyl)-4-acetamido-L-phenylalanine sodium salt;
N-(N-4-methyl-benzoyl-L-tyrosyl)-4-acetamido-L-phenylalanine;
N-(N-4-chloro-benzoyl-L-phenylalanyl)-L-phenylalanine;
N-(N-4-chloro-benzoyl-L-phenylalanyl)-L-phenylalanine sodium salt;
N-(N-2-chloro-benzoyl-L-phenylalanyl)-L-phenylalanine;
N-(N-4-nitro-benzoyl-L-tyrosyl)-L-phenylalanine;
N-(N-4-acetamido-benzoyl-L-phenylalanyl)-L-phenylalanine;
N-(N-isonicotinyl-L-phenylalanyl)-L-tyrosine;
N-(N-4-acetamido-benzoyl-L-phenylalanyl)-L-tyrosine;
N-(N-4-propionamido-benzoyl-L-phenylalanyl)-L-phenylalanine;
N-(N-4-acetamido-benzoyl-L-tyrosyl)-L-phenylalanine; and
N-(N-isonicotinyl-L-tyrosyl)-4-nitro-L-phenylalanine.

In another aspect, the present invention is directed to a pharmaceutical composition, comprising a therapeutically effective amount of the compound of the present invention and a pharmaceutically acceptable carrier. The pharmaceutical composition of the present invention may also comprise other conventional pharmaceutically acceptable adjuvants, such as excipients and the like.

The compounds of the present invention may also be used in combination with other active components as long as they do not produce disadvantageous effects, such as allergy or the like.

The carriers used in the pharmaceutical compositions of the present invention are those common types available in the pharmaceutical field, including binders, lubricants, disintegrants, solubilizers, diluents, stabilizers, suspending agents, colorants, flavouring agents and the like used in oral formulations; preservatives, solubilizers and stabilizers and the like used in injectable formulations; and substrates, diluents, lubricants and preservatives and the like used in focal formulations.

The pharmaceutical composition of the present invention may be formulated as various dosage forms, such as oral formulations (e.g. tablets, capsules, solutions or suspensions), injectable formulations (e.g. injectable solutions, suspensions or powders) and focal formulations (e.g. ointments or solutions).

The pharmaceutical formulations of the present inventions may be administered orally or parenterally (such as intravenously, subcutaneously, intraperitoneally or focally). Where some medicaments are not stable under the gastral conditions, they may be formulated as enteric tablets.

In a further aspect, the present invention is directed to a method of preventing and/or treating viral infections, especially the hepatitis B virus and human immunodeficiency virus infections in a subject, wherein the method comprises administering to the subject a therapeutically effective amount of the compound or the pharmaceutical composition of the present invention.

"Therapeutically effective amount" refers to that amount of a compound of the invention which, when administered to a mammal, preferably a human, is sufficient to effect treatment, as defined below, of a disease or condition of the hepatitis B virus and human immunodeficiency virus infections in the mammal, preferably a human. The amount of a compound of the invention which constitutes a "therapeutically effective amount" will vary depending on the compound, the condition and its severity, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or disorder of interest, and includes:
(i) preventing the disease or condition from occurring in a mammal, in particular, when such mammal is predisposed to the condition but has not yet been diagnosed as having it;
(ii) inhibiting the disease or condition, i.e., arresting its development; or
(iii) relieving the disease or condition, i.e., causing regression of the disease or condition.

As used herein, the terms "disease" and "condition" may be used interchangeably or may be different in that the particular malady or condition may not have a known pathogenic factor (so that etiology has not yet been worked out) and it is therefore not yet recognized as a disease but only as an undesirable condition or syndrome, wherein a more or less specific set of symptoms have been identified by clinicians.

In a still further aspect, the present invention is directed to a process for preparing a phenylalanine dipeptide derivative of formula I,

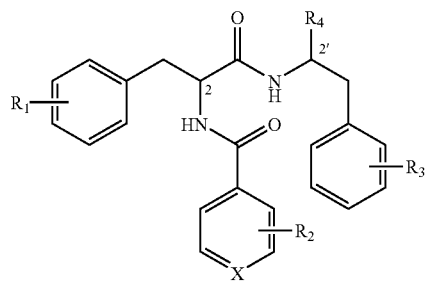

wherein,
each $R_1$, $R_2$ and $R_3$ independently represent a single substituent or multiple substituents at different positions of a ring, wherein,
$R_1$ and $R_3$ are selected from the group consisting of H, $NO_2$, $NH_2$, NRR', —NHCOR, $NHCO(CH_2)_n COOH$, OH, OCOR, OR, $O(CH_2)_n NRR'$, $O(CH_2)_n COOR$, $O(CH_2)_n COOH$ and $CH_2NRR'$;
$R_2$ is selected from the group consisting of H, $NO_2$, $NH_2$, NRR', NHCOR, $NHCO(CH_2)_n COOH$, $NHOC(CH_2)_n NRR'$, OH, OCOR, OR, $O(CH_2)_n NRR'$, $O(CH_2)_n COOH$, CN, $CH_2NRR'$, COOH, COOR, $C_1$-$C_6$ alkyl, halo,

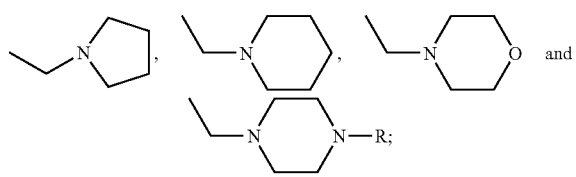

$R_4$ is selected from the group consisting of $CH_2OH$, COOR, $CH_2OCOR$, $CH_2OCO(CH_2)_n COOH$, COONa and COOH;
each R and R' in the $R_1$ to $R_4$ described above represent identical or different, linear or branched $C_1$-$C_6$ alkyl or $C_3$-$C_7$ cycloalkyl;
said alkyl and cycloalkyl may be further optionally substituted with one or two substituents selected from the group consisting of OH, $NO_2$, CN, $CF_3$ and halo;
X is CH or N; and
n is an integral number of 1 to 4;
a single stereoisomer, a mixture of stereoisomers, a racemic mixture of stereoisomers, or tautomers thereof, pharmaceutically acceptable salts thereof, prodrugs thereof or solvates thereof;
wherein the process comprises the following steps (synthesis scheme I):
i) subjecting a compound of formula I-1 to reacting with a compound of formula I-2 to obtain a compound of formula I-3,

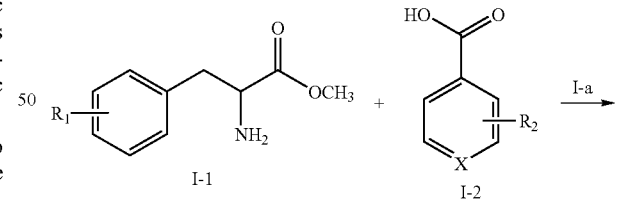

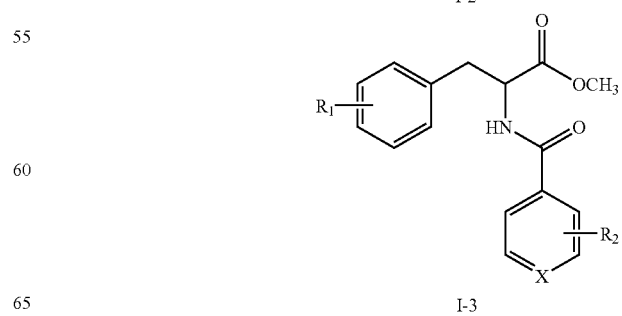

ii) converting the compound of formula I-3 into a compound of formula I-4 under basic conditions,

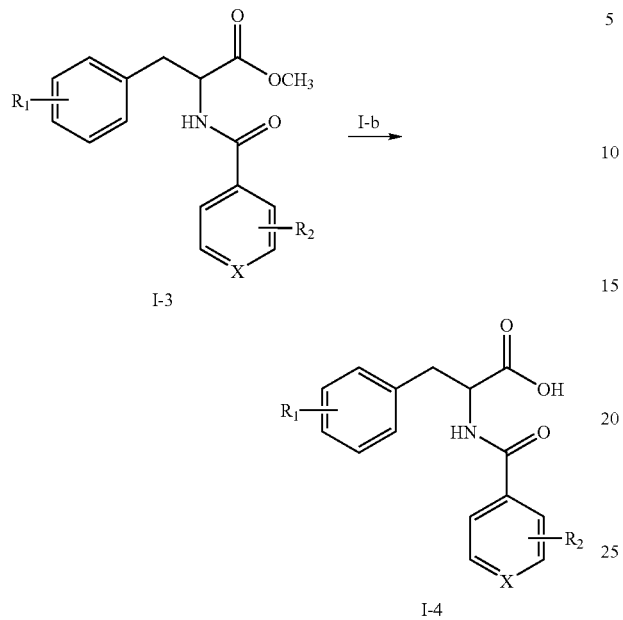

iii) subjecting the compound of formula I-4 to reacting with a compound of formula I-5 to give the target compound,

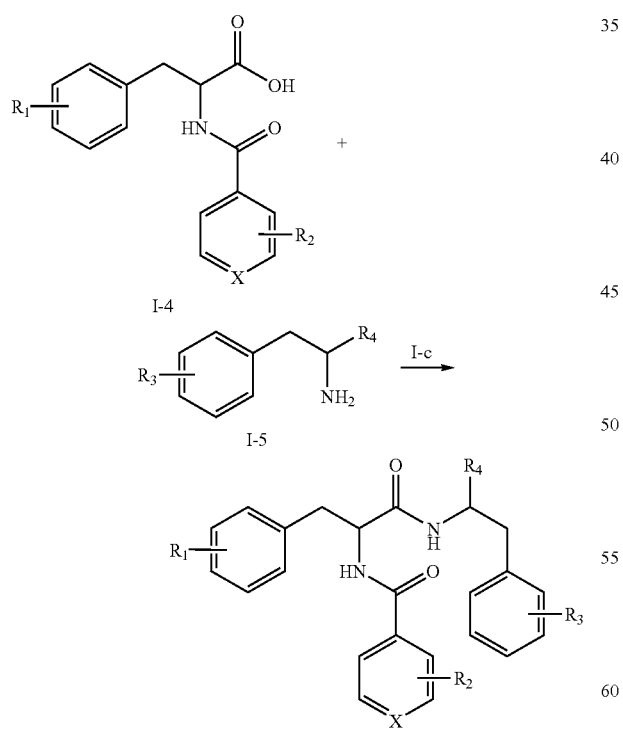

wherein $R_1$, $R_2$, $R_3$ and $R_4$ in formulae I-1, I-2, I-3, I-4 and I-5 are defined as indicated above; or wherein the process comprises the following steps (synthesis scheme II):

i) subjecting a compound of formula II-1 to reacting to obtain a compound of formula II-2,

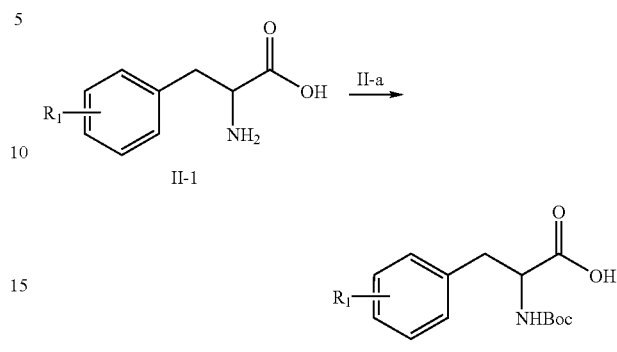

ii) subjecting the compound of formula II-2 to reacting with a compound of formula II-3 to obtain a compound of formula II-4,

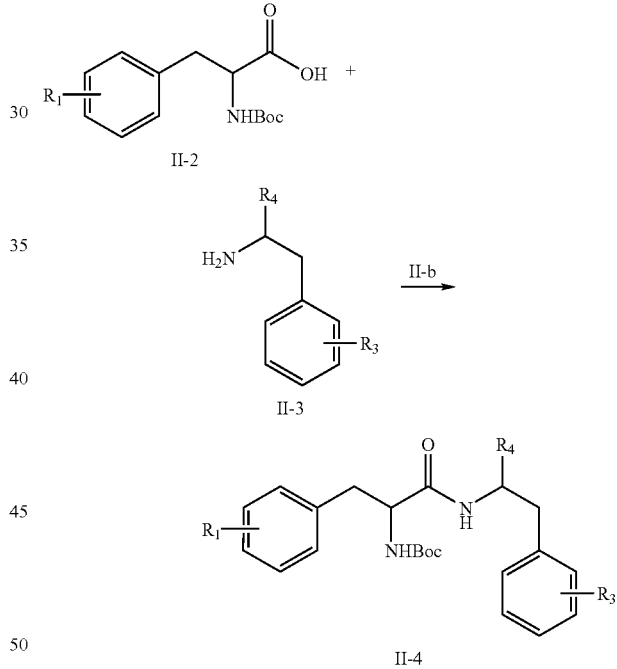

iii) hydrolyzing the compound of formula II-4 to obtain a compound of formula II-5 under acidic conditions,

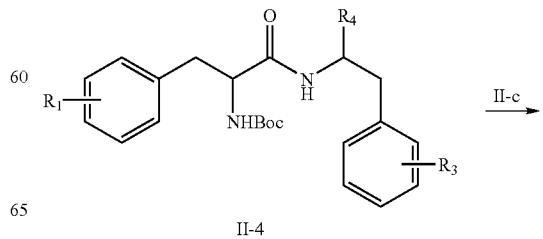

-continued

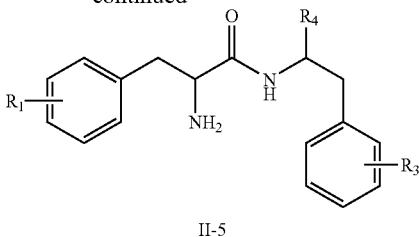

II-5 iv) subjecting the compound of formula II-5 to reacting with a compound of formula II-6 to give the target compound,

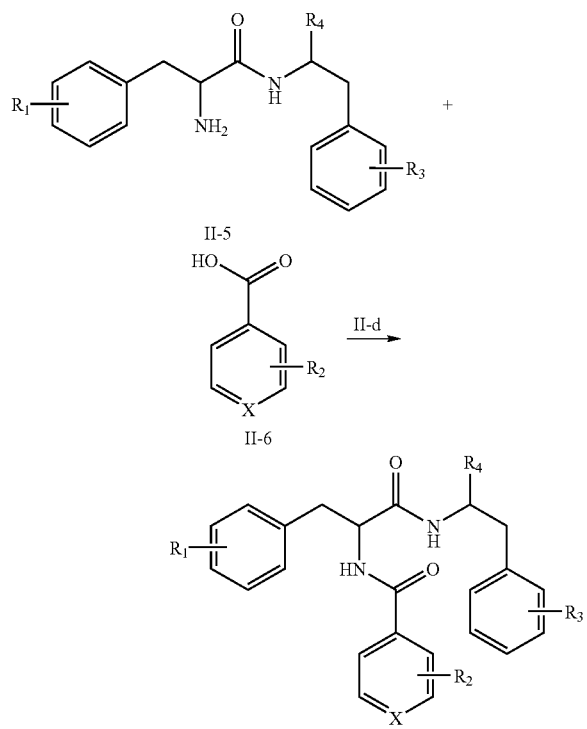

wherein $R_1$, $R_2$, $R_3$ and $R_4$ in formulae I-1, I-2, I-3, I-4 and I-5 are defined as indicated above.

In some preferred embodiments, a compound of formula I-1 reacts with a compound of formula I-2 to obtain a compound of formula I-3 under the presence of DDC, DMAP and $CH_2Cl_2$ at room temperature.

In some preferred embodiments, a compound of formula I-3 is converted into a compound of formula I-4 under a basic condition of 1.0 M NaOH at room temperature.

In some preferred embodiments, a compound of formula I-4 reacts with a compound of formula I-5 under the presence of isobutyl chloroformate (IBCF) and N-methylmorpholine (NMM) at the temperature between −5° C. and 10° C.

In some preferred embodiments, a compound of formula II-1 reacts with (t-BuOCO)$_2$O to obtain a compound of formula II-2 under the presence of 1.0 M NaOH and the catalyst of TBAB.

In some preferred embodiments, a compound of formula II-2 reacts with a compound of formula II-3 to obtain a compound of formula II-45 under the presence of isobutyl chloroformate (IBCF) and N-methylmorpholine (NMM) at the temperature between −5° C. and 10° C.

In some preferred embodiments, a compound of formula II-4 hydrolyzes to obtain a compound of formula II-5 under the presence of TFA and $CH_2Cl_2$ at room temperature over 2 hours.

In some preferred embodiments, a compound of formula II-5 with a compound of formula II-6 under the presence of DDC, DMAP and $CH_2Cl_2$ at room temperature.

In some preferred embodiments, $R_2$ in the compounds in the preparation process is selected from the group consisting of H, $C_1$-$C_6$ alkyl, halo, $NO_2$, NHCOR, $NHCO(CH_2)_n$COOH, OH, OCOR, $O(CH_2)_n$NRR', $CH_2$NRR',

and COOH.

In some preferred embodiments, $R_1$ and $R_3$ in the compounds in the preparation process are selected from the group consisting of H, $NO_2$, $NH_2$, NRR', NHCOR, $NHCO(CH_2)_n$COOH, OH, OCOR, OR and $O(CH_2)_n$NRR'.

In some more preferred embodiments, $R_1$ in the compounds in the preparation process is selected from the group consisting of H, $NO_2$, $NHCOCH_3$, $NHCOCH_2CH_3$, $N(CH_3)_2$, $NHCO(CH_2)_2COOH$, OH, $OCH_3$, $OCOCH_3$, $O(CH_2)_2N(CH_3)_2$ and $OCH_2COOH$.

In some more preferred embodiments, $R_3$ in the compounds in the preparation process is selected from the group consisting of H, $NO_2$, $NHCOCH_3$, $NHCOCH_2CH_3$, OH, $OCOCH_3$, $OCH_3$, $OCH_2CH_3$ and $O(CH_2)_3CH_3$.

In some more preferred embodiments, $R_2$ in the compounds in the preparation process is selected from the group consisting of H, F, Cl, $NO_2$, $NHCOCH_3$, $NHCOCH_2Cl$, $NHCOCH_2CH_3$, $NHCO(CH_2)_2COOH$, $NHCOCH_2N(CH_3)_2$, OH, $OCOCH_2CH_3$, $O(CH_2)_2N(CH_3)_2$, $CH_3$, $CH_2N(CH_3)_2$, COOH, (1-pyrrolidyl)acetamido,

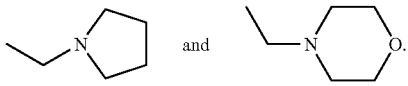

In some more preferred embodiments, $R_4$ in the compounds in the preparation process is selected from the group consisting of $CH_2OH$, $COOCH_3$, $CH_2OCOCH_3$, $CH_2OCOCH_2CH_3$, $CH_2OCOCH_2COOH$, $CH_2OCO(CH_2)_2$COOH, COONa and COOH.

Alternatively, where $R_1$ is H, $R_2$ is selected from the group consisting of H, $C_1$-$C_6$ alkyl, halo and $NO_2$, a compound of formula I-8 where $R_1$ is —H may be prepared in the preparation process of a compound of formula I as follow,

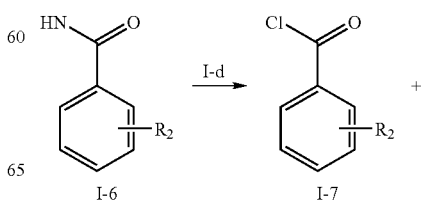

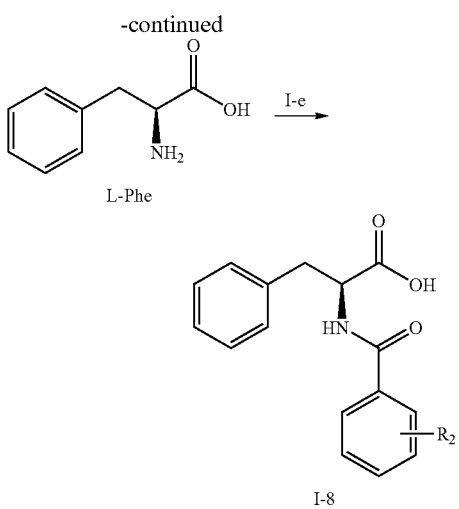

i) subjecting a benzoic acid derivative I-6 to reacting with thionyl chloride to obtain a benzoyl chloride derivative I-7; and ii) subjecting the benzoyl chloride derivative I-7 to reacting with L-phenylalanine in a sodium hydroxide solution to obtain an intermediate I-8.

In some preferred embodiments, the process of preparing a compound of formula I comprises the following steps:

i) mixing a benzoic acid derivative of formula I-2, a derivative of methyl L-tyrosinate or methyl L-phenylalaninate of formula I-1, dicyclohexylcarbodiimide (DCC) and p-dimethylaminopyridine (DMAP), and then adding them into anhydrous $CH_2Cl_2$ to obtain an intermediate I-3;

ii) dissolving the intermediate I-3 with absolute alcohol and then adding sodium hydroxide to hydrolyze the intermediate I-3 at room temperature over 2 hours to obtain an intermediate I-4; and iii) mixing and dissolving the intermediate I-4, a compound of formula I-5 and N-methylmorpholine (NMM) in dry $CH_2Cl_2$, and dropwise adding isobutyl chloroformate (IBCF) to obtain an object product.

In some preferred embodiments, the process of preparing a compound of formula I comprises the following steps:

i) dissolving a derivative of L-phenylalanine of formula II-1 with NaOH solution and then adding di-t-butyl dicarbonate $((t-BuOCO)_2O)$ and tetrabutylammomium bromide (TBAB) to obtain an intermediate II-2;

ii) subjecting the intermediate II-2 to reacting with a compound of formula II-3 to obtain an intermediate II-4 using similar procedures to those in step iii) of synthesis scheme I;

iii) dissolving the intermediate II-4 with trifluoroacetic acid (TFA), stirring at room temperature over 2 hours, adding water, and adjusting pH to basicity (pH 11-12) with sodium carbonate to obtain an intermediate II-5; and iv) mixing the intermediate II-5, a benzoic acid derivative II-6, DDC and DMAP, and then adding them into anhydrous $CH_2Cl_2$ to obtain the object product.

Other N-(N-benzoyl-phenylalanyl)-phenylalanine dipeptide derivatives represented by formula I may be prepared by selecting appropriate reaction substrates, such as L-phenylalanine, D-phenylalanine, L-tyrosine, D-tyrosine, various phenylalanines with different substituents, various phenylalaninols with different substituents and various benzoic acids with different substituents, via synthesis scheme I or synthesis scheme II and converting and substituting groups in the obtained derivatives, such as reduction of nitro groups into amino groups, substitution, acylation and alkylation of amino groups at a benzene ring (through diazotization intermediates), acylation and alkylation or substitution with other electrophilic reagents (e.g. $ClCH_2(CH_2)_nNRR'$, $ClCH_2(CH_2)_nCOOR$) of phenolic hydroxyl groups at a benzene ring.

EXAMPLES

Hereinafter, the present invention will be described in detail with reference to the specific examples. It shall be appreciated that these examples are intended to illustrate but not to limit the scope of the present invention.

In the following examples, the resultant compounds were characterized with $^1H$ and $^{13}C$ spectra obtained on a 400 MHz nuclear magnetic resonance spectrometer (INOVA type, with nanogram probes, Varian Inc.). The molecular weights of the resultant compounds were measured with HP-5973 mass spectrometer of Hewlett-Packard Inc. All used reagents are of analytical grade or of chemical grade.

A. Preparation of Representative Reaction Intermediates 4-nitro-L-phenylalanine (No. M-05)

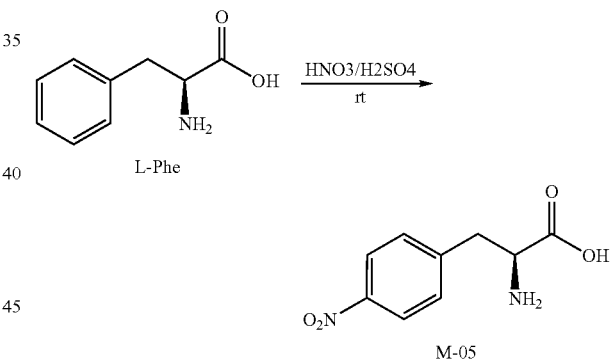

Reagents and Reaction Conditions:

$HNO_3/H_2SO_4$ (1.4:1.1), room temperature (rt.), and 5 hours

Preparation Procedures:

L-phenylalanine (16.5 g, 100 mmol) was dissolved in 85% $H_2SO_4$ (50 ml). To the mixture was dropwise added under stirring a mixed acid of concentrated $HNO_3$ and concentrated $H_2SO_4$ (V/V=1.4/1.1), which was pre-prepared and cooled to room temperature. The reaction mixture was stirred at room temperature over 5 hours. The pH of the reaction solution was adjusted to 2-3 with 40% NaOH. A large amount of precipitate was obtained. The precipitate was filtered, washed with water until the pH is neutral, and dried under reduced pressure to give 4-niro-L-phenylalanine (20 g, 95.2%).

The intermediate 3-niro-L-tyrosine was prepared with L-tyrosine as the starting material and diluted nitric acid (30%) as the nitrating agent instead of the mixed acid.

4-nitro-L-phenylalanol (No. M-12)

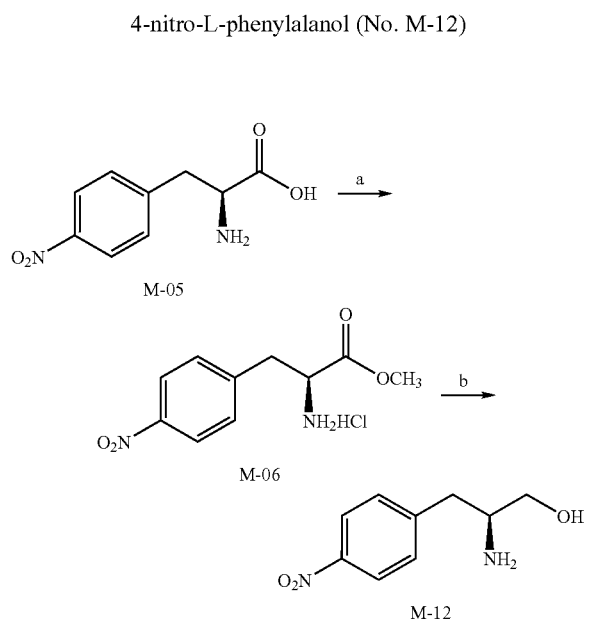

Reagents and Reaction Conditions:
(a) MeOH and SOCl$_2$, room temperature, 2.5 hours, reflux over 30 minutes; and
(b) NaBH$_4$/H$_2$O, reacting overnight Preparation Procedures:
(a) A reaction flask charged with methanol (90 ml) was sufficiently cooled in an ice-salt bath with stirring. To the reaction flask was dropwise added thionyl chloride (SOCl$_2$) (9.5 ml, 132 mmol). After the completion of addition, the reaction was warmed to room temperature. To the reaction flask was added M-05 (100 mmol). The reaction mixture was stirred at room temperature for 2.5 hours and refluxed in a water bath for 30 minutes. The solution was evaporated to dryness under reduced pressure to recover the solvents. The resulting residue was recrystallized from a solvent mixture of methanol and ethyl ether to give 4-nitro-L-phenylalanol hydrochloride (22.1 g, 85.0%) as a light yellow powder (No. M-06).
(b) In water (15 ml) was dissolved NaBH$_4$ (1.13 g, 30 mmol). The solution was cooled in an ice-salt bath. The solution was slowly and dropwise added to an aqueous solution of M-06 (2.4 g, 9.2 mmol). The reaction was allowed to warm to room temperature (over about 2 hours) and kept overnight at room temperature. The reaction solution was extracted with ethyl acetate (3×50 ml) on the morrow. The ethyl acetate layers were combined and washed in turn with saturated aqueous NaHCO$_3$ (20 ml) and saturated aqueous sodium chloride (20 ml) and dried over anhydrous Na$_2$SO$_4$. The solution was evaporated under reduced pressure to recover the solvents, giving a product (1.23 g, 68.2%) as a light yellow powder. The structure of the product was consistent with that of M-12 as characterized by spectra.

With a similar synthesis process, L-phenylalanine and L-tyrosine were selected as a starting material, respectively, to prepare L-phenylalanol hydrochloride, L-tyrosine hydrochloride, L-phenylalaninol and L-tyrosinol as starting materials for further synthesis.

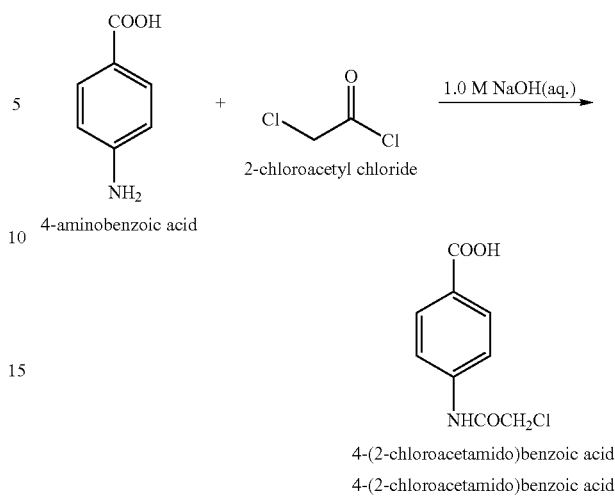

Reagents and Reaction Conditions:
1.0 M NaOH (aq.), −5° C., 2 hours, and stirring overnight at room temperature Preparation Procedures:
In 1.0 M NaOH (220 ml) was dissolved 4-aminobenzoic acid (13.7 g, 100 mmol). The solution was cooled to −5° C. in an ice-salt bath. To the solution was dropwise added 2-chloroacetyl chloride (12 ml, 0.15 mol). After the completion of the addition, the reaction was continued for 2 hours and then warmed to room temperature and stirred overnight. The reaction solution was adjusted with concentrated hydrochloric acid to the pH 1-2. The precipitate was filtered, washed with water until the pH was neutral, and dried to give 4-(2-chloroacetamido) benzoic acid (15.58 g, 73.0%) as a white powder.

2-chloro-N,N-dimethylethanamine hydrochloride

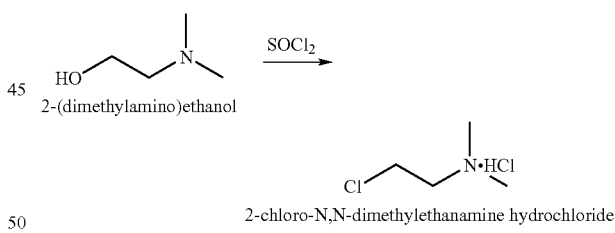

Reagents and Reaction Conditions:
SOCl$_2$, CHCl$_3$, and reflux for 4 hours

Preparation Procedures:
2-(dimethylamino)-ethanol) (5 ml, 0.05 mol) and CHCl$_3$ (20 ml) were mixed and stirred at room temperature. To the mixture was dropwise added SOCl$_2$ (4.3 ml, 0.06 mol). After the completion of the addition (over about 2 hours), the mixture was refluxed in a water bath for 3 hours. The solution was evaporated to dryness to recover the solvents. The residue was dissolved in EtOH (100 ml). The solution was filtered to remove the insoluble impurities and evaporated to dryness. The resulting solid was dispersed in CH$_2$Cl$_2$ (100 ml) with moderate stirring and filtered. The precipitate was washed with suitable amount of CH$_2$Cl$_2$ and dried to give the intermediate 2-chloro-N,N-dimethylethanamine hydrochloride (6.18 g, 85.8%) as a white powder.

4-dimethylaminobenzoic acid hydrochloride (No. M-25)

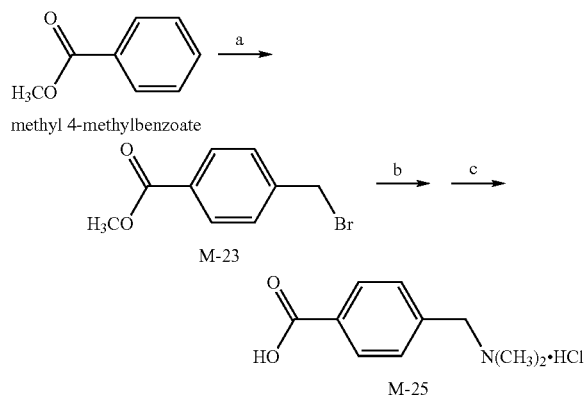

Reagents and Reaction Conditions:
(a) NBS, ABIN, CCl$_4$, reflux for 12 hours;
(b) NH(CH$_3$)$_2$HCl, K$_2$CO$_3$, KI, anhydrous EtOH, rt., reaction overnight; and
(c) 1.0 M HCl (aq.), reflux for 8 hours.

Preparation Procedures:
(a) Methyl p-methyl benzoate (4.5 g, 30 mmol) was dissolved in dry CCl$_4$ (60 ml). To the solution were added NBS (6.6 g, 36.9 mmol) and azobisisobutyronitrile (ABIN, 12 mg). The reaction was refluxed in an oil bath under argon for 12 hours. The solution was filtered to remove the resulted precipitate. The filtrate was evaporated under reduced pressure to dryness to recover the solvents, giving methyl 4-bromomethyl benzoate (8.58 g, cal. 6.87 g) as a milk white oil (No. M-23).
(b) In absolute alcohol (50 ml) were mixed NH(CH$_3$)$_2$HCl (6.11 g, 75 mmol), K$_2$CO$_3$ (17.25 g, 125 mmol) and KI (1.66 g, 10 mmol). To the solution was dropwise added M-23 (50 mmol) under nitrogen. The reaction was stirred overnight. The reaction solution was extracted and purified on the morrow to give 4-dimethylaminobenzoic acid as a colorless oil.
(c) The product obtained in the previous step was dissolved 1.0 M HCl and hydrolyzed over 8 hours with reflux. The solution was evaporated under reduced pressure to recover the solvents. The product was dried to give 4-dimethylaminobenzoic acid hydrochloride as an off-white powder.

Following the synthesis process of M-25, the intermediates having the following structures can be prepared with corresponding starting materials.

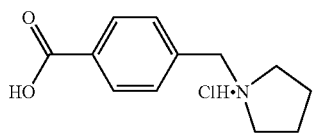

M-71

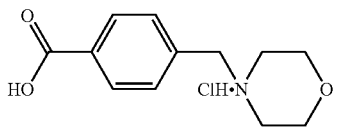

M-74

B. Synthetic Preparation of Object Products

Example 1 methyl N-(N-benzoyl-L-phenylalanyl)-L-phenylalaninate

Reagents and Reaction Conditions:
(a) 2.0 M NaOH (aq.), benzoyl chloride, −5° C. to rt., 3 hours, 93%; and
(b) CH$_2$Cl$_2$, isobutyl chloroformate (IBCF), N-methylmorpholine NMM), −5° C.

Preparation Procedures:
(a) L-phenylalanine (1.65 g, 10.0 mmol) was dissolved in a 2.0 M sodium hydroxide (aq., 11 ml). The mixture was cooled in an ice-salt bath. To the mixture was dropwise added benzoyl chloride (10.0 mmol) with stirring. After completion of the addition, the mixture was warmed to room temperature and allowed to react over 2 hours. The pH of the reactants was adjusted to 5-6 with concentrated hydrochloric acid (1.8 ml, 21.6 mmol). The resultant precipitate was filtered, washed with water until the pH was neutral, and dried to give N-benzoyl-L-phenylalanine (2.50 g, 93.0%) as a white powder (No. M-03).

(b) To a mixture of the intermediates M-03 (1.0 mmol) and M-01 (1.05 mmol) and N-methylmorpholine (NMM, 23.0 mmol) in dry $CH_2Cl_2$ (50 ml) was dropwise added isobutyl chloroformate (IBCF, 1.07 mmol) while cooling in an ice-salt bath (−5° C.). After completion of the addition, the reaction mixture was stirred for further 2 hours (the reaction process was monitored with TLC). The reaction was quenched with a small amount of water. The solution was evaporated under reduced pressure to dryness to recover solvent. The resultant solid was dissolved completely with a suitable amount of EtOAc. The solution was washed in turn with distilled water, diluted hydrochloric acid, distilled water, 5% $NaHCO_3$ and saturated aqueous NaCl, dried over anhydrous sodium sulfate and evaporated under reduced pressure to dryness to recover ethyl acetate. The residue was recrystallized from ethyl acetate to give methyl N-(N-benzoyl-L-phenylalanyl)-L-phenylalaninate crystal (280 mg, 65.0%) as a white needle.

Spectra Data: EI-MS m/z: 430 ($M^+$), 283, 240, 128, 114, 72, 59 (100), 43; $^1$H-NMR ($CDCl_3$, 400 MHz): δ 7.68 (2H, d, J=7.6 Hz, H-3", 7"), 7.51 (1H, m, H-5"), 7.42 (2H, t, H-4", 6"), 7.31-7.13 (8H, m, H-5, 9, 6, 8, 5', 9', 6', 8'), 6.97 (2H, m, H-7, 7'), 6.76 (1H, d, J=7.4 Hz, NHCO), 6.37 (1H, d, J=7.6 Hz, NHCO), 4.85 (1H, m, H-2), 4.77 (1H, m, H-2'), 3.70 (3H, s, OMe), 3.23-2.94 (4H, m, H-3, 3'); $^{13}$C-NMR ($CDCl_3$, 100 MHz): δ 171.3 (C-1), 170.4 (C-1'); 167.0 (C-1"), 136.4 (C-4), 135.5 (C-4'), 133.6 (C-2"), 131.8 (C-5"), 129.4 (C-6, 8), 129.1 (C-6', 8'), 128.7 (C-4", 6"), 128.6 (C-5, 9), 128.5 (C-5', 9'), 127.1 (C-3", 7"), 127.0 (C-7, 7'), 54.5 (C-2), 53.4 (C-2'), 52.3 (C-COMe), 38.0 (C-3), 37.8 (C-3').

Following the similar synthetic process as that in example 1, derivatives of examples 2-18 were prepared, respectively, through selecting appropriate reaction materials and intermediates.

Example 2

N-(N-benzoyl-L-phenylalanyl)-L-phenylalaninol

Spectra Data: $^1$H-NMR ($CDCl_3$, 400 MHz): δ 7.72 (2H, d, J=8.0 Hz, H-3", 7"), 7.53 (1H, , J=7.2 Hz, H-5"), 7.44 (2H, t, H-4", 6"), 7.35-7.07 (10H, m, H-5-9, 5'-9'), 6.80 (1H, d, J=7.6 Hz, NHCO), 5.92 (1H, d, J=7.6 Hz, NHCO), 4.77 (1H, m, H-2), 4.10 (1H, m, H-2'), 3.42 (2H, m, H-1'), 3.27 (1H, dd, J=5.6, 13.6 Hz, H-3a), 3.04 (1H, dd, J=9.2, 13.6 Hz, H-3b), 2.77 (1H, dd, J=7.6, 13.6 Hz, H-3'a), 2.68 (1H, dd, J=6.8, 13.6 Hz, H-3'b); M (EI) m/z: 402 ($M^+$), 384, 311, 252, 224 (100), 92.

Example 3 methyl N-(N-4-fluoro-benzoyl-L-phenylalanyl)-L-phenylalaninate

Spectra Data: $^1$H-NMR ($CDCl_3$, 400 MHz): δ 7.69-7.72 (2H, m, H-3", 7"), 7.07-7.28 (10H, m, H-5-9, 5'-9'), 6.96-6.98 (2H, m, H-4", 6"), 6.80 (1H, d, J=7.6 Hz, NH), 6.34 (1H, d, J=7.6 Hz, NH), 4.76-4.84 (2H, m, H-2, 2'), 3.70 (3H, s, $OCH_3$), 2.98-3.18 (4H, m, H-3, 3'); $^{13}$C-NMR ($CDCl_3$, 100 MHz): δ 171.24 (s), 170.41 (s), 165.97 (2×s), 136.28 (s), 135.44 (s), 129.47 (s), 129.38 (4×d), 129.11 (2×d), 128.69 (2×d), 128.55 (2×d), 127.11 (2×d), 115.74 (d), 115.52 (d), 54.56 (d), 53.44 (d), 52.38 (q), 38.13 (t), 37.82 (t); MS(EI) m/z: 448 ($M^+$), 416, 389, 357, 309, 286, 270, 242, 218, 180, 162, 147, 131, 123 (100), 120, 95, 91, 77, 41, 28, 15.

Example 4 methyl N-(N-benzoyl-L-phenylalanyl)-L-tyrosinate

Spectra Data: mp 184.0-186.0° C.; $^1$H-NMR (DMSO, 400 MHz): δ 9.18 (1H, s, Ar—OH), 8.52 (1H, d, J=8.4 Hz, NHCO), 8.40 (1H, d, J=7.6 Hz, NHCO), 7.77 (2H, d, J=7.6 Hz, H-3", 7"), 7.50 (1H, t, H-5"), 7.42 (2H, t, H-4", 6"), 7.33 (2H, d, J=7.2 Hz, H-5, 9), 7.24 (2H, t, H-6, 8), 7.16 (1H, t, H-7), 6.99 (2H, d, J=8.4 Hz, H-5', 9'), 6.62 (2H, d, J=8.4 Hz, H-6', 8'), 4.74 (1H, m, H-2), 4.45 (1H, m, H-2'), 3.60 (3H, s, OMe), 3.11-2.84 (4H, m, H-3, 3'); $^{13}$C-NMR (DMSO, 100 MHz): δ 171.8 (C-1), 171.5 (C-1'), 166.2 (C-1"), 156.0 (C-7'), 138.2 (C-4), 134.0 (C-2"), 131.1 (C-5"), 129.9 (C-5', 9'), 129.1 (C-6, 8), 128.0 (×2), 127.9 (×2), 127.3 (C-3", 7"), 126.8 (C-7), 126.1 (C-4'), 115.0 (C-6', 8'), 54.4 (C-2), 53.9 (C-2'), 51.7 (C—OMe), 36.9 (C-3), 35.9 (C-3').

Example 5

N-(N-3-methyl-benzoyl-L-phenylalanyl)-L-phenylalaninol

Spectra Data: mp 177.0-178.5° C.; $^1$H-NMR (DMSO, 400 MHz): δ 8.44 (1H, d, J=8.4 Hz, NHCO), 7.89 (1H, d, J=8.4 Hz, NHCO), 7.59-7.56 (2H, m, H-3", 7"), 7.32-7.10 (12H, m, H-5", 6", H-5-9, 5'-9'), 4.83 (1H, t, $CH_2OH$), 4.67 (1H, m, H-2), 3.88 (1H, m, H-2'), 3.33-3.23 (2H, m, H-1), 3.04-2.91 (2H, m, H-3), 2.85 (1H, dd, J=5.6, 13.6 Hz, H-3'a), 2.65 (1H, dd, J=8.0, 13.6 Hz, H-3'b), 2.33 (3H, s, Ar—$CH_3$); $^{13}$C-NMR (DMSO, 100 MHz): δ 171.0 (C-1), 166.2 (C-1"), 139.0 (C-4'), 138.5 (C-4), 137.5 (C-4"), 134.1 (C-2"), 131.9 (C-5"), 129.3 (×3, C-6', 8', 6"), 128.13 (×4, C-5', 9', C-6, 8), 128.07 (×2, C-5, 9), 128.0 (C-3"), 126.2 (C-7"), 126.0 (C-7), 124.6 (C-7"), 62.2 (C-1'), 54.8 (C-2), 52.5 (C-2'), 33.3, 36.5, 21.0 ($ArCH_3$).

Example 6

N-(N-benzoyl-4-nitro-L-phenylalanyl)-L-phenylalaninol

Spectra Data: mp 196.0-199.0° C.; $^1$H-NMR (DMSO, 400 MHZ): δ8.62 (1H, D, J =8.4 Hz, NHCO), 8.12 (2H, d, J=8.8 Hz, H-6, 8), 8.05 (1H, d, J=8.8 Hz, NHCO), 7.78 (2H, d, J =6.4 Hz, H-3", 7"), 7.59 (2H, d, J=8.4 Hz, H-5, 9), 7.51 (1H, t, H-5"), 7.43 (2H, t, H-4", 6"), 7.26-7.12 (5H, m, H-5'-9'), 4.85 (1H, t, OH), 4.76 (1H, m, H-2), 3.89 (1H, m, H-2'), 3.32-3.26 (2H, m, H-1'), 3.19-3.07 (2H, m, H-3), 2.92-2.81 (2H, m, H-3); $^{13}$C-NMR (DMSO, 100 MHz): δ 170.5 (C-1), 166.1 (C-1"), 145.0 (C-7), 146.2 (C-4), 139.0 (C-4'), 133.8 (C-2"), 131.4 (C-5"), 130.5 (C-5, 9), 129.2 (C-6", 8"), 128.2 (C-4", 6"), 128.1 (C-5', 9'), 127.4 (C-3", 7"), 125.9 (C-7"), 123.2 (C-6, 8), 62.2 (C-1'), 54.3 (C-2'), 52.6 (C-2), 37.1 (C-3'), 34.9 (C-3).

Example 7

N-(N-4-chloro-benzoyl-L-phenylalanyl)-L-phenylalaninol

Spectra Data: mp 211.5-214.0° C.; $^1$H-NMR (DMSO, 400 MHz): δ 8.63 (1H, d, J=8.4 Hz, NHCO), 7.93 (1H, d, J=8.0 Hz, NHCO), 7.81 (2H, d, J=8.0 Hz, H-3", 7"), 7.51 (2H, d, J=8.0 Hz, H-4", 6"), 7.12-7.31 (10H, m, H-5-9, 5'-9'), 4.82 (1H, s, OH), 4.68 (H, m, H-2), 3.90 (1H, m, H-2'), 3.29-3.39 (2H, m, H-1'), 2.49-3.01 (4H, m, H-3, 3'); $^{13}$C-NMR (DMSO, 100 MHz): δ 170.9 (C-1), 165.1 (C-1"), 139.0 (C-4), 138.1 (C-4'), 136.2 (C-5"), 132.4 (C-2"), 129.4 (×2), 129.2 (×2), 128.3 (×2), 128.09 (×2), 128.07 (×2), 126.2, 125.9, 62.2 (C-1'), 54.9 (C-2), 52.5 (C-2'), 37.3 (C-3), 36.4 (C-3'). M (EI) m/z: 436 (M$^+$), 406, 345, 327, 303, 286, 258, 190, 139 (100), 120, 111, 104, 91, 73, 57, 43, 28.

Example 8

N-(N-2-chloro-benzoyl-L-phenylalanyl)-L-phenylalaninol

Spectra Data: $^1$H-NMR (CDCl$_3$, 400 MHz): δ 7.15-7.40 (14H, m, H-5-9, 5-9', 4"-7"), 4.59-4.82 (1H, m, H-2), 4.07-4.10 (1H, m, H-2'), 3.41-3.42 (2H, m, 1'), 2.71-3.17 (4H, m, H-3, 3'); $^{13}$C-NMR(CDCl$_3$, 100 MHz): δ 172.81 (s), 169.53 (s), 139.61 (s), 138.42 (s), 137.02 (s), 132.27 (d), 131.96 (s), 130.92 (d), 130.45 (2×d), 130.43 (2×d), 130.01 (d), 129.46 (2×d), 129.42 (2×d), 127.96 (d), 127.80 (d), 127.33 (d), 63.73 (t), 56.55 (d), 54.14 (d), 38.93 (t), 37.87 (t); MS(EI) m/z: 436 (M$^+$), 418, 406, 345, 327, 303, 286, 258, 190, 139 (100), 120, 104, 91, 73, 60, 43, 28, 18.

Example 9 methyl N-(N-3-methyl-benzoyl-L-phenylalanyl)-L-phenylalaninate

Spectra Data: mp 190.0-192.0° C.; $^1$H-NMR (CDCl$_3$, 400 MHz): δ 7.51 (1H, s, H-3"), 7.46 (1H, d, J=4.4 Hz, H-7"), 7.31-7.23 (6H, m, H-5", 6", 6, 8, 6', 8'), 7.16-7.11 (4H, m, H-5, 9, 5', 9'), 6.99-6.95 (2H, m, H-7, 7'), 6.68 (1H, d, J=8.0 Hz, NHCO), 7.89 (1H, d, J=7.4 Hz, NHCO), 4.80 (2H, m, H-2, 2'), 3.70 (3H, s, OCH$_3$), 3.23-2.93 (4H, m, H-3, 3'), 2.39 (3H, s, Ar—CH$_3$); $^{13}$C-NMR (CDCl$_3$, 100 MHz): δ 171.2 (C-1), 170.3 (C-1'), 167.2 (C-1"), 138.4 (C-4"), 136.4 (C-4), 135.5 (C-4'), 133.5 (C-2"), 132.6 (C-5"), 129.4 (×2), 129.1 (×2), 128.7 (×2), 128.5 (×2), 128.4 (C-6"), 127.7 (C-3"), 127.0 (×2, C-7, 7"), 124.0 (C-7"), 54.4 (C-2), 53.4 (C-2'), 52.4 (OCH$_3$), 38.0, 37.8.

Example 10 methyl N-(N-2-chloro-benzoyl-L-phenylalanyl)-L-phenylalaninate

Spectra Data: mp 152.5-153.5° C.; $^1$H-NMR (CDCl$_3$, 400 MHz): δ 7.51 (1H, d, J=8.0 Hz, H-7"), 7.35-7.34 (2H, m, H-4", 5"), 7.30-7.17 (9H, m, H-5, 6, 8, 9, 5', 6', 8', 9', 6"), 6.97-6.95 (2H, m, H-7, 7'), 6.75 (1H, d, J=7.6 Hz, NHCO), 6.30 (1H, d, J=7.6 Hz, NH), 4.85 (1H, m, H-2), 4.78 (1H, m, H-2), 3.67 (3H, s, OCH$_3$), 3.20-3.00 (4H, m, H-3, 3'); $^{13}$C-NMR (CDCl$_3$, 100 MHz): δ 171.2, 169.9, 166.1, 136.2, 135.5, 134.1, 131.6, 130.8, 130.3, 130.2, 129.4 (×2), 129.2 (×2), 128.7 (×2), 128.6 (×2), 127.14, 127.12, 127.0, 54.9, 53.4, 52.3, 37.9, 37.8; M (EI) m/z: 464 (M$^+$), 432, 373, 309, 302, 286, 258, 218, 180, 162, 147, 139 (100), 131, 120, 112, 102, 97, 91, 83, 73, 60, 44, 28.

Example 11 methyl N-(N-2-chloro-benzoyl-L-phenylalanyl)-L-tyrosinate

Spectra Data: mp 164.5-167.0° C.; $^1$H-NMR (DMSO, 400 MHz): δ 9.27 (1H, s, Ar—OH), 8.60 (1H, d, J=8.4 Hz, NHCO), 8.40 (1H, d, J=7.2 Hz, NHCO), 7.42-7.14 (9H, m, H-4"-7", 5-9), 7.03 (2H, d, J=8.4 Hz, H-5', 9'), 6.67 (2H, d, J=8.4 Hz, H-6', 8'), 4.75 (1H, m, H-2), 4.46 (1H, m, H-2'), 3.08-2.79 (4H, m, H-3, 3'); $^{13}$C-NMR (DMSO, 100 MHz): δ 171.9 (C-1), 171.1 (C-1'), 166.0 (C-1"), 156.1 (C-7'), 137.8 (C-4), 136.4 (C-5"), 130.8 (C-3"), 130.1 (C-5', 9'), 130.0 (C-2"), 129.2 (C-4"), 129.2 (C-6, 8), 128.9 (C-7"), 128.0 (C-5, 9), 126.9 (C-6", C-4'), 126.3 (C-7), 115.1 (C-6', 8'), 54.0 (C-2), 51.8 (C-2'), 37.2, 36.0.

Example 12 methyl N-(N-benzoyl-4-nitro-L-phenylalanyl)-L-phenylalaninate

Spectra Data: mp 202.0-204.5° C.; $^1$H-NMR (CDCl$_3$, 400 MHz): δ 8.09 (2H, d, J=8.8 Hz, H-6, 8), 7.71 (2H, d, J=7.6 Hz, H-3", 7"), 7.54 (1H, t, H-5"), 7.43 (2H, t, H-4", 6"), 7.38 (2H, d, J=8.8 Hz, H-5, 9), 7.13 (3H, m, H-6'-8'), 6.99 (2H, m, H-5', 9'), 6.93 (1H, br, NHCO), 6.56 (1H, br, NHCO), 4.94 (1H, m, H-2), 4.80 (1H, m, H-2'), 3.73 (3H, s, OCH$_3$), 3.29 (1H, dd, J=7.2, 13.6 Hz, H-3'a), 3.22 (1H, dd, J=5.6, 14.0 Hz, H-3'b), 3.09 (1H, dd, J=5.6, 14.0 Hz, H-3a), 3.01 (1H, dd, J=6.4, 14.0 Hz, H-3b); $^{13}$C-NMR (CDCl$_3$, 100 MHz): δ 171.3 (C-1), 169.8 (C-1'), 167.1 (C-1"), 147.0 (C-7), 144.1 (C-4), 135.2 (C-4'), 133.1 (C-2"), 132.2 (C-5"), 130.3 (C-5, 9), 129.0 (C-6', 8'), 128.7 (C-5', 9'), 128.6 (C-4", 6"), 127.2 (C-7'), 127.0 (C-3", 7"), 123.7 (C-6, 8), 54.0 (C-2), 53.2 (C-2'), 52.5 (OCH$_3$), 38.0, 37.8.

Example 13

N-(N-4-methyl-benzoyl-L-phenylalanyl)-L-phenylalaninol

Spectra Data: mp 200.0-202.0° C.; $^1$H-NMR (DMSO, 400 MHz): δ 8.39 (1H, d, J=8.8 Hz, NHCO), 7.86 (1H, d, J=8.8 Hz, NHCO), 7.68 (2H, d, J=8.0 Hz, H-3", 7"), 7.29-7.11 (12H, m, H-4", 6", 5'-9', 5-9), 4.81 (1H, t, OH), 4.65 (1H, m, H-2), 3.88 (1H, m, H-2'), 3.33-3.24 (2H, m, H-1'), 3.03-2.90 (2H, m, H-3), 2.84 (1H, dd, J=6.0, 13.6 Hz, H-3'a), 2.65 (1H, dd, J=8.0, 13.6 Hz, H-3'b), 2.33 (3H, s, Ar—CH$_3$); $^{13}$C-NMR (DMSO, 100 MHz): δ 171.0 (C-1), 166.0 (C-1"), 141.2 (C-5"), 139.0 (C-4'), 138.4 (C-4), 131.3 (C-2"), 129.2 (×4, C-6, 8, C-6', 8'), 128.7 (C-4", 6"), 128.1 (C-5', 9'), 128.0 (C-5, 9), 127.5 (C-3", 7"), 126.2 (C-7), 125.9 (C-7'), 62.2 (C-1'), 54.8 (C-2'), 52.5 (C-2), 37.3, 36.4, 21.0 (Ar—CH$_3$).

Example 14 methyl N-(N-benzoyl-4-nitro-L-phenylalanyl)-L-tyrosinate

Spectra Data: mp 200.0-202.0° C.; $^1$H-NMR (DMSO, 400 MHz): δ 9.27 (1H, s, Ar—OH), 8.67 (1H, d, J=8.4 Hz, NHCO), 8.57 (1H, d, J=7.2 Hz, NHCO), 8.13 (2H, d, J=8.4 Hz, H-6, 8), 7.76 (2H, d, J=7.2 Hz, H-3", 7"), 7.62 (2H, d, J=8.4 Hz, H-5, 9), 7.51 (1H, t, H-5"), 7.43 (2H, t, H-4", 6"), 7.00 (2H, d, J=8.0 Hz, H-5', 9'), 6.63 (2H, d, J=8.0 Hz, H-6', 8'), 4.83 (1H, m, H-2), 4.42 (1H, m, H-2'), 3.57 (3H, s, OMe), 3.22-2.84 (4H, m, H-3, 3'); $^{13}$C-NMR (DMSO, 100 MHz): δ 171.9 (C-1), 171.2 (C-1'), 166.3 (C-1"), 156.1 (C-7'), 146.8 (C-7), 146.2 (C-4), 133.8 (C-2"), 131.4 (C-5"), 130.6 (C-5, 9), 130.4 (C-4'), 130.1 (C-5', 9'), 128.3 (C-4", 6"), 127.4 (C-3", 7"), 122.2 (C-6, 8), 115.1 (C-6', 8'), 54.2 (C-2), 50.0 (C-2'), 51.9 (C—OMe), 36.8 (C-3), 35.9 (C-3').

Example 15 methyl N-(N-benzoyl-4-nitro-L-phenylalanyl)-4-nitro-L-phenylalaninate

Spectra Data: mp 220.0-221.5° C; 1H-NMR (DMSO, 400 MHz): δ 8.57 (1H, d, J=8.0 Hz, NHCO), 8.52 (1H, d, J=8.8 Hz, NHCO), 8.04 (2H, d, J=8.4 Hz, H-6', 8'), 7.73 (2H, d, J=7.6 Hz, H-3", 7"), 7.49 (3H, m, H-5", 5', 9'), 7.41 (2H, t, H-4", 6"), 7.31 (2H, d, J=7.2 Hz, H-5, 9), 7.23 (2H, t, H-6, 8), 7.14 (1H, t, H-7), 4.70 (1H, m, H-2), 4.62 (1H, m, H-2'), 3.61 (3H, s, OCH$_3$), 3.25-2.90 (4H, m, H-3, 3'); $^{13}$C-NMR (DMSO, 100 MHz): δ 171.6 (C-1), 171.4 (C-1'), 166.2 (C-1"), 146.3 (C-7'), 145.5 (C-4'), 138.3 (C-4), 133.9 (C-2"), 131.4 (C-5"), 130.6 (C-5', 9'), 129.2 (C-6, 8), 128.2 (×2), 128.1 (×2), 127.4 (C-3", 7"), 126.3 (C-7'), 123.2 (C-6', 8'), 54.5 (C-2), 52.9 (C-2'), 52.1 (OCH$_3$), 36.8, 36.2.

Example 16

N-(N-benzoyl-L-phenylalanyl)-4-nitro-L-phenylalaninol

Spectra Data: mp 192.0-195.0° C.; $^1$H-NMR (DMSO, 400 MHz): δ 8.46 (1H, d, J=8.4 Hz, NHCO), 7.97 (2H, d, J=8.0 Hz, H-6', 8'), 7.92 (1H, d, J=8.8 Hz, NHCO), 7.76 (2H, d, J=8.0 Hz, H-3", 7"), 7.52-7.40 (5H, m, H-4"-6", 5', 9'), 7.29 (2H, d, J=7.2 Hz, H-5, 9), 7.23 (2H, t, H-6, 8), 7.14 (1H, t, H-7), 4.89 (1H, t, OH), 4.63 (1H, m, H-2), 4.97 (1H, m, H-2'), 3.36-3.27 (2H, m, H-1'), 3.05-2.72 (4H, m, H-3, 3'); $^{13}$C-NMR (DMSO, 100 MHz): δ 171.0 (C-1), 166.1 (C-1"), 147.6 (C-7'), 145.8 (C-4'), 138.4 (C-4), 133.9 (C-2"), 131.4 (C-5"), 130.5 (C-5', 9'), 129.2 (C-6, 8), 128.2 (×2), 128.0 (×2), 127.3 (C-3", 7"), 126.2 (C-7'), 123.0 (C-6', 8'), 62.6 (C-1'), 54.8 (C-2), 51.9 (C-2'), 37.0, 36.4.

Example 17 methyl N-(N-$^4$-methyl-benzoyl-L-phenylalanyl)-L-tyrosinate

Spectra Data: mp 207.0-208.5° C.; $^1$H-NMR (DMSO, 400 MHz): δ 9.24 (1H, s, Ar—OH), 8.45 (2H, m, NHCO×2), 7.68 (2H, d, J=8.0 Hz, H-3", 7"), 7.33 (2H, d, J=7.2 Hz, H-5, 9), 7.22 (4H, m, H-4", 6", 6, 8), 7.14 (1H, t, H-7), 7.00 (2H, d, J=8.0 Hz, H-5', 9'), 6.63 (2H, d, J=8.0 Hz, H-6', 8'), 4.73 (1H, m, H-2), 4.42 (1H, m, H-2'), 3.57 (3H, s, OCH$_3$), 3.08-2.87 (4H, m, H-3, 3'), 2.32 (3H, s, Ar—CH$_3$); $^{13}$C-NMR (DMSO, 100 MHz): δ 172.0, 171.7, 166.1 (C-1"), 156.1 (C-7'), 141.2 (C-5"), 138.4 (C-4), 131.2 (C-2"), 130.1 (C-5', 9'), 129.2 (C-6, 8), 128.7 (C-4", 6"), 128.0 (C-5, 9), 127.4 (C-3", 7"), 127.0 (C-4'), 126.2 (C-7), 115.1 (C-6', 8'), 54.5 (C-2), 54.1 (C-2'), 51.8 (OCH$_3$), 36.9 (C-3), 35.9 (C-3'), 21.0 (Ar—CH$_3$).

Example 18 methyl N-(N-4-methyl-benzoyl-4-nitro-L-phenylalanyl)-L-tyrosinate

Spectra Data: mp 213.0-215.0° C.; $^1$H-NMR (DMSO, 400 MHz): δ 9.31 (1H, s, Ar—OH), 8.61-8.57 (2H, m, NHCO×2), 8.12 (2H, d, J=8.8 Hz, H-6, 8), 7.67 (2H, d, J=7.6 Hz, H-3", 7"), 7.60 (2H, d, J=8.8 Hz, H-5, 9), 7.23 (2H, d, J=8.0 Hz, H-4", 6"), 7.00 (2H, d, J=8.4 Hz, H-5', 9'), 6.63 (2H, d, J=8.0 Hz, H-6', 8'), 4.81 (1H, m, H-2), 4.41 (1H, m, H-2'), 3.56 (3H, s, OCH$_3$), 3.21-3.06 (2H, m, H-3'), 2.94-2.84 (2H, m, H-3), 2.32 (3H, s, Ar—CH$_3$); $^{13}$C-NMR (DMSO, 100 MHz): δ 172.0 (C-1), 171.3 (C-1'), 166.2 (C-1"), 156.1 (C-7'), 146.9 (C-7), 146.2 (C-4), 141.3 (C-5"), 131.0 (C-2"), 130.6 (C-5, 9), 130.1 (C-5', 9'), 128.8 (C-4", 6"), 127.4 (C-3", 7"), 126.9 (C-4'), 123.2 (C-6, 8), 115.1 (C-6', 8'), 54.2, 53.9, 51.9 (OCH$_3$), 36.8, 35.9, 21.0 (Ar—CH$_3$).

Example 19

N-(N-4-chloro-benzoyl-L-tyrosyl)-L-phenylalaninol

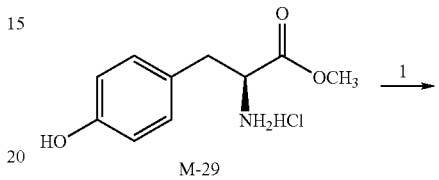

M-29

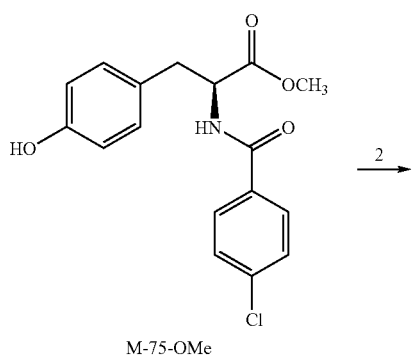

M-75-OMe

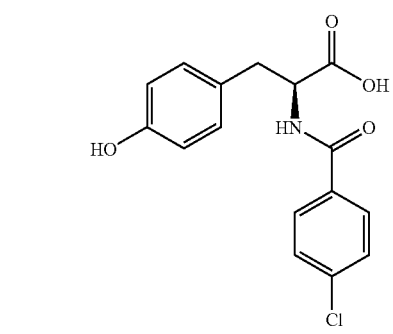

M-75

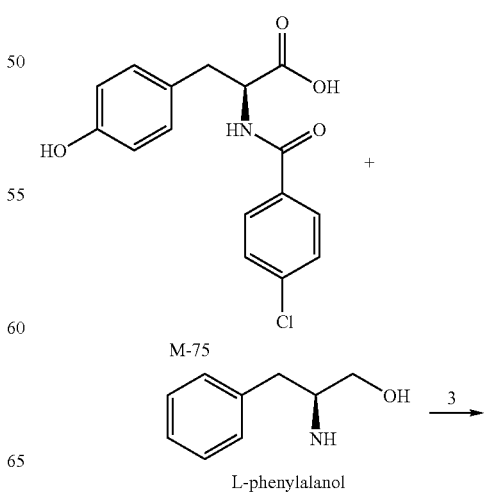

M-75

L-phenylalanol

-continued

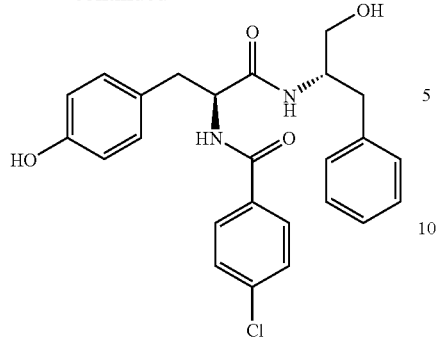

Reagents and Reaction Conditions:
(1) DCC, DMAP, 4-chlorobenzoic acid, CH$_2$Cl$_2$, rt., overnight;
(2) 1.0 M NaOH, rt., 2 hours; and
(3) CH$_2$Cl$_2$, isobutyl chloroformate (IBCF), N-methylmorpholine (NMM), −5° C.

Preparation Procedures:
(1) In a reaction flask were mixed an intermediate M-29 (2.31 g, 10 mmol), 4-chlorobenzoic acid (1.57 g, 10 mmol), DCC (2.47 g, 12 mmol) and DMAP (200 mg, as a catalyst). To the mixture was added anhydrous CH$_2$Cl$_2$ (150 ml). The reaction mixture was stirred overnight under nitrogen at room temperature. The resulting precipitate dicyclohexylurea (DCU) was removed by filtering on the morrow. The filtrate was evaporated to dryness to recover the solvents. The resulting solid was dissolved with ethyl acetate (100 ml). The solution was washed in turn with distilled water, diluted hydrochloric acid (40 ml), distilled water, 5% NaHCO$_3$ (40 ml) and saturated aqueous NaCl (40 ml) and dried over anhydrous sodium sulfate. The solution was evaporated under reduced pressure to dryness to recover ethyl acetate, giving an intermediate M-75-Ome (3.18 g, 95.3%) as a white foam.
(2) The product M-75-OMe synthesized in the previous step (3.10 g, 9.29 mmol) was dissolved in CHCl$_3$ (100 ml). The solution was extracted with 1.0 M NaOH (2×20 ml). The water layers were combined and stirred at room temperature for 2 hours followed by adjusting the pH to 2-3 with concentrated hydrochloric acid. The resulting solution was extracted with EtOAc (2×30 ml). The ethyl acetate layers were combined and dried over anhydrous Na$_2$SO$_4$. The solution was evaporated under reduced pressure to dryness to recover the solvents, giving an intermediate M-75 (2.82 g, 95.1%) as a light yellow foam.
(3) Following the similar procedure as that in synthesis step (b) of Example 1, the object product was prepared as a white powder.

Spectra Data: mp 217.0-219.0° C.; $^1$H-NMR (DMSO, 400 MHz): δ 9.15 (1H, s, Ar—OH), 8.54 (1H, d, J=8.4 Hz, NHCO), 7.87 (1H, d, J=8.4 Hz, NHCO), 7.81 (2H, d, J=8.4 Hz, H-3", 7"), 7.53 (2H, d, J=8.4 Hz, H-4", 6"), 7.25-7.12 (5H, m, H-5'-9'), 7.07 (2H, d, J=8.0 Hz, H-5, 9), 6.60 (2H, d, J=8.0 Hz, H-6, 8), 4.80 (1H, s, OH), 4.57 (1H, m, H-2'), 3.88 (1H, m, H-2'), 3.35-3.24 (2H, m, H-1'), 2.95-2.60 (4H, m, H-3, 3'); $^{13}$C-NMR (DMSO, 100 MHz): δ 170.9 (C-1), 164.9 (C-1"), 155.7 (C-7), 139.0 (C-5"), 136.1 (C-4'), 132.9 (C-4), 130.1 (C-5, 9), 129.4 (×2), 129.2 (×2), 128.33, 128.28 (×2), 128.1 (×2), 125.9 (C-7'), 114.8 (C-6, 8), 62.2 (C-1'), 55.2 (C-2), 52.5 (C-2'), 36.5, 36.4.

Following the similar synthetic process as that in example 19, derivatives of examples 20-48 were prepared, respectively, through selecting appropriate reaction materials and intermediates Example 20 methyl N-(N-4-chloro-benzoyl-L-tyrosyl)-L-phenylalaninate

Spectra Data: mp 203.5-205.0° C.; $^1$H-NMR (DMSO, 400 MHz): δ 9.16 (1H, s, Ar—OH), 8.61 (1H, d, J=8.4 Hz, NHCO), 8.53 (1H, d, J=8.8 Hz, NHCO), 7.79 (2H, d J=8.4 Hz, H-3", 7"), 7.52 (2H, d, J=8.4, H-4", 6"), 7.26-7.18 (5H, m, H-5'-9'), 7.10 (2H, d, J=8.4 Hz, H-5, 9), 6.61 (2H, d, J=8.4 Hz, H-6, 8), 4.64 (1H, m, H-2), 4.49 (1H, m, H-2'), 3.58 (3H, s, OCH$_3$), 3.03-2.80 (4H, m, H-3, 3'); $^{13}$C-NMR (DMSO, 100 MHz): δ 171.8, 171.7, 165.1 (C-1"), 155.7 (C-7), 137.0 (C-4'), 136.1 (C-5"), 132.8 (C-2"), 130.1 (C-5, 9), 129.4 (×2), 129.1 (×2, C-4), 128.3 (×4), 126.6 (C-7'), 114.8 (C-6, 8), 54.9 (C-2), 53.7 (C-2'), 51.9 (C—OMe), 36.5 (×2).

Example 21

N-(N-benzoyl-L-tyrosyl)-L-phenylalaninol

Spectra Data: mp 216.0-217.5° C.; $^1$H-NMR (DMSO, 400 MHz): δ 9.18 (1H, s, Ar—OH), 8.42 (1H, d, J=8.4 Hz, NHCO), 7.86 (1H, d, J=8.4 Hz, NHCO), 7.77 (2H, d, J=6.8 Hz, H-3", 7"), 7.49 (1H, t, H-5"), 7.43 (2H, t, H-4", 6"), 7.21-7.11 (5H, m, H-5'-9'), 7.07 (2H, d, J=8.4 Hz, H-5, 9), 6.59 (2H, d, J=8.4 Hz, H-6, 8), 4.84 (1H, t, OH), 4.56 (1H, m, H-2), 3.87 (1H, m, H-2'), 3.34-3.22 (2H, m, H-1'), 2.91-2.61 (4H, m, H-3, 3'); $^{13}$C-NMR (DMSO, 100 MHz): δ 171.2 (C-1), 166.1 (C-1"), 155.7 (C-7), 139.1 (C-4'), 134.2 (C-2"), 131.4 (C-5"), 130.2 (C-5, 9), 129.3 (C-6', 8'), 128.4 (C-4), 128.2 (C-4", 6"), 128.1 (C-5', 9'), 127.5 (C-3", 7"), 126.0 (C-7'), 114.9 (C-6, 8), 62.3 (C-1'), 55.3 (C-2), 52.6 (C-2'), 36.6, 36.5.

Example 22

N-(N-2-chloro-benzoyl-L-tyrosyl)-L-phenylalaninol

Spectra Data: mp 168.0-169.0° C.; $^1$H-NMR (DMSO, 400 MHz): δ 9.19 (1H, s, Ar—OH), 8.50 (1H, d, J=8.4 Hz, NHCO), 7.78 (1H, d, J=8.8 Hz, NHCO), 7.46-7.16 (9H, m, H-4"-7", 5'-9'), 7.04 (2H, d, J=8.4 Hz, H-5, 9), 6.65 (2H, d, J=8.4 Hz, H-6, 8), 4.83 (1H, t, OH), 4.56 (1H, m, H-2), 3.91 (1H, m, H-2'), 3.34-3.24 (2H, m, H-1'), 2.91-2.85 (2H, m, H-3), 2.74-2.63 (2H, m, H-3'); $^{13}$C-NMR (DMSO, 100 MHz): δ 170.5 (C-1), 165.8 (C-1"), 155.7 (C-7), 139.0 (C-4'), 136.5 (C-5"), 130.8 (C-4), 130.2 (C-5, 9), 130.0 (C-2"), 129.6 (C-3"), 129.2 (C-6', 8'), 128.9 (C-4"), 128.1 (C-5', 9'), 127.9 (C-7"), 126.9 (C-6"), 125.9 (C-7'), 114.5 (C-6, 8), 62.1 (C-1'), 54.8 (C-2), 52.3 (C-2'), 36.8, 36.4.

Example 23 methyl N-(N-2-chloro-benzoyl-L-tyrosyl)-L-phenylalaninate

Spectra Data: mp 175.5-177.5° C.; $^1$H-NMR (DMSO, 400 MHz): δ 9.20 (1H, s, Ar—OH), 8.52 (1H, d, J=8.8 Hz, NHCO), 8.43 (1H, d, J=8.0 Hz, NHCO), 7.46-7.16 (9H, m, H-4"-7", 5'-9'), 7.07 (2H, d, J=8.4 Hz, H-5, 9), 6.66 (2H, d, J=8.4 Hz, H-6, 8), 4.64 (1H, m, H-2), 4.53 (1H, m, H-2'), 3.59

(3H, s, OCH3), 3.07-2.67 (4H, m, H-3, 3'); ¹³C-NMR (DMSO, 100 MHz): δ 171.8 (C-1), 171.2 (C-1'), 165.9 (C-1"), 155.8 (C-7), 137.0 (C-4'), 136.4 (C-5"), 130.8 (C-4), 130.2 (C-5, 9), 130.0 (C-2"), 129.6 (C-3"), 129.2 (C-6, 8), 128.9 (C-4"), 128.3 (C-5', 9'), 127.8 (C-7"), 126.9 (C-6"), 126.6 (C-7'), 114.8 (C-6', 8'), 54.4 (C-2), 53.8 (C-2'), 51.9 (OCH₃), 36.7, 36.5.

Example 24

N-(N-4-fluoro-benzoyl-L-tyrosyl)-L-phenylalaninol

Spectra Data: mp 194.5-195.5° C.; ¹H-NMR (DMSO, 400 MHz): δ 9.18 (1H, s, Ar—OH), 8.51 (1H, d, J=8.4 Hz, NHCO), 7.90-7.87 (3H, m, NHCO, H-3", 7"), 7.31-7.00 (6H, m, H-4", 6", 5', 9', 5, 9), 6.63 (2H, d, J=8.4 Hz, H-6, 8), 4.83 (1H, t, OH), 4.60 (1H, m, H-2), 3.90 (1H, m, H-2'), 3.38-3.23 (2H, m, H-1'), 2.95-2.56 (4H, m, H-3, 3'); ¹³C-NMR (DMSO, 100 MHz): δ 171.3, 171.1, 165.0 (C-1"), 162.7 (C-5"), 155.7 (C-7), 139.1 (C-4'), 130.1 (C-4), 130.0 (C-5, 9), 129.2 (C-6', 8'), 128.4 (C-2"), 128.1 (C-5', 9'), 125.9 (C-7'), 115.2 (×2), 115.0 (×2), 114.8 (C-6, 8), 69.8 (C-1'), 55.2 (C-2), 52.5 (C-2'), 36.5, 36.4.

Example 25 methyl N-(N-4-fluoro-benzoyl-L-tyrosyl)-L-phenylalaninate

Spectra Data: mp 186.5-189.0° C.; ¹H-NMR (DMSO, 400 MHz): δ 9.20 (1H, s, Ar—OH), 8.55 (2H, m, NHCO×2), 7.86 (2H, m, H-3", 7"), 7.30-7.13 (7H, m, H-4", 6", 5'-9'), 7.04 (2H, d, J=8.4, H-5, 9), 7.02 (2H, d, J=8.4, H-6, 8), 4.64 (1H, m, H-2), 4.50 (1H, m, H-2'), 3.59 (3H, s, OCH₃), 3.09-2.79 (4H, m, H-3, 3'); ¹³C-NMR (DMSO, 100 MHz): δ 171.84, 171.79, 165.1 (C-1"), 162.7 (C-5"), 155.7 (C-7), 137.1 (C-4'), 130.55s, 130.52s, 130.13 (C-4), 130.09 (C-5, 9), 130.04d, 129.1 (C-6', 8'), 128.3 (C-5', 9'), 126.6 (C-7'), 115.2d, 115.0d, 114.8 (C-6, 8), 54.9 (C-2), 53.7 (C-2'), 51.9 (OMe), 36.6, 36.2.

Example 26

N-(N-4-methyl-benzoyl-L-tyrosyl)-L-phenylalaninol

Spectra Data: mp 193.0-195.0° C.; ¹H-NMR (DMSO, 400 MHz): δ 9.17 (1H, s, ArNHCO), 8.36 (1H, d, J=8.4 Hz, NHCO), 7.88 (1H, d, J=8.4 Hz, NHCO), 7.72 (2H, d, J=8.0 Hz, H-3", 7"), 7.26-7.00 (9H, m, H-4", 6", 5, 9, 5'-9'), 6.61 (2H, d, J=8.4 Hz, H-6, 8), 4.83 (1H, t, OH), 4.58 (1H, m, H-2), 3.88 (1H, m, H-2'), 3.36-3.25 (2H, m, H-1'), 2.93-2.62 (4H, m, H-3, 3'), 2.34 (3H, s, Ar—CH₃); ¹³C-NMR (DMSO, 100 MHz): δ 171.2 (C-1), 165.9 (C-1"), 155.7 (C-7), 141.1 (5"), 139.1 (C-4'), 131.4 (C-2"), 130.1 (C-5, 9), 129.2 (C-6', 8'), 128.7 (C-4", 6"), 128.4 (C-4), 128.1 (C-5', 9'), 127.5 (C-3", 7"), 125.9 (C-7'), 114.8 (C-6, 8), 62.2 (C-1'), 55.2 (C-2), 52.5 (C-2'), 36.5, 36.4, 21.0 (Ar—CH₃).

Example 27

N-(N-4-hydroxyl-benzoyl-L-phenylalanyl)-L-phenylalaninol

Spectra Data: mp 223.0-225.0° C.; ¹H-NMR (DMSO, 400 MHz): δ 9.98 (1H, s, Ar—OH), 8.22 (1H, d, J=8.8 Hz, NHCO), 7.83 (1H, d, J=8.4 Hz, NHCO), 7.66 (2H, d, J=8.8 Hz, H-3", 7"), 7.29-7.09 (10H, m, H-5-9, 5'-9'), 6.76 (2H, d, J=8.4 Hz, H-4", 6"), 4.80 (1H, t, J=5.2 Hz, OH), 4.62 (1H, m, H-2), 3.87 (1H, m, H-2'), 3.34-3.22 (2H, m, H-1'), 3.02-2.92 (2H, m, H-3), 2.84 (1H, dd, J=5.6, 13.6 Hz, H-3'a), 2.64 (1H, dd, J=8.0, 13.6, Hz, H-3'b); ¹³C-NMR (DMSO, 100 MHz): δ 171.2 (C-1), 165.8 (C-1"), 160.2 (C-5"), 139.0 (C-4'), 138.5 (C-4), 129.4 (C-3", 7"), 129.23 (C-6', 8'), 129.21 (C-6, 8), 128.09 (C-5', 9'), 128.03 (C-5, 9), 126.2 (C-7), 125.9 (C-7'), 124.7 (C-2"), 114.7 (C-4", 6"), 62.2 (C-1'), 54.7 (C-2), 52.5 (C-2'), 37.2 (C-3'), 36.5 (C-3).

Example 28 methyl N-(N-4-hydroxyl-benzoyl-L-phenylalanyl)-L-phenylalaninate

Spectra Data: mp 151.0-153.0° C.; ¹H-NMR (DMSO, 400 MHz): δ 9.96 (1H, s, Ar—OH), 8.44 (1H, d, J=7.2 Hz, NHCO), 8.24 (1H, d, J=8.0 Hz, NHCO), 7.64 (2H, d, J=8.4 Hz, H-3", 7"), 7.31-7.12 (10H, m, H-5-9, 5'-9'), 6.75 (2H, d, J=8.8 Hz, H-4", 6"), 4.69 (1H, m, H-2), 3.49 (1H, m, H-2'), 3.57 (3H, s, OCH₃), 3.06-2.88 (4H, m, H-3, 3'); ¹³C-NMR (DMSO, 100 MHz): δ 171.8 (C-1, 1'), 165.9 (C-1"), 160.2 (C-5"), 139.4 (C-4), 137.0 (C-4'), 129.4 (C-3", 7"), 129.17 (×2), 129.13 (×2), 128.3 (C-5', 9'), 128.0 (C-5, 9), 126.6 (C-7'), 126.2 (C-7), 124.7 (C-2"), 114.7 (C-4", 6"), 54.4 (C-2), 53.7 (C-2'), 51.8 (OCH₃), 36.9, 36.6.

Example 29 methyl N-(N-benzoyl-3-nitro-L-tyrosyl)-L-phenylalaninate

Spectra Data: mp 201.0-202.5° C.; ¹H-NMR (DMSO, 400 MHz); δ 8.61-8.56 (2H, m, NHCO×2), 7.91 (1H, s, H-5), 7.76 (2H, d, J=8.4 Hz, H-3", 7"), 7.51-7.41 (5H, m, H-9, 4"-6", ArOH), 7.26-7.18 (5H, m, H-5'-9'), 7.03 (1H, d, J=8.4 Hz, H-8), 4.70 (1H, m, H-2), 4.50 (1H, m, H-2'), 3.57 (3H, S, OCH₃), 3.07-2.87 (4H, m, H-3, 3'); ¹³C-NMR (DMSO, 100 MHz): δ 171.8, 171.3, 166.3 (C-1"), 150.8 (C-7), 137.0 (C-4'), 136.4 (C-9), 136.1 (C-6), 133.9 (C-2"), 131.4 (C-5"), 129.5 (C-4), 129.1 (C-6', 8'), 128.3 (C-5', 9'), 128.2 (C-4", 6"), 127.4 (C-3", 7"), 126.6 (C-7'), 125.4 (C-5), 118.8 (C-8), 54.4 (C-2), 53.8 (C-2'), 51.9 (OCH₃), 36.6, 35.6.

Example 30 methyl N-(N-4-nitro-benzoyl-L-tyrosyl)-L-phenylalaninate

Spectra Data: mp 212.0-214.0° C.; ¹H-NMR (DMSO, 400 MHz): δ 9.17 (1H, s, Ar—OH), 8.89 (1H, d, J=8.4 Hz, NHCO), 8.60 (1H, d, J=7.2 Hz, NHCO), 8.29 (2H, d, J=8.4 Hz, H-4", 6"), 7.99 (2H, d, J=8.8 Hz, H-3", 7"), 7.26-7.18 (5H, m, H-5'-9'), 7.11 (2H, d, J=8.0 Hz, H-5, 9), 6.61 (2H, d, J=8.4 Hz, H-6, 8), 4.68 (1H, m, H-2), 4.49 (1H, m, H-2'), 3.57 (3H, s, OCH₃), 3.08-2.78 (4H, m, H-3, 3'); ¹³C-NMR (DMSO, 100 MHz): δ 171.9, 171.5, 164.5 (C-1"), 155.8 (C-7), 149.1 (C-5"), 139.7 (C-2"), 137.1 (C-4'), 130.1 (C-5, 9), 129.1 (C-6', 8'), 128.9 (C-3", 7"), 128.3 (C-5', 9'), 128.1 (C-4), 126.6 (C-7'), 123.5 (C-4", 6"), 114.9 (C-6, 8), 55.1 (C-2), 53.8 (C-2'), 51.9 (OCH₃), 36.5, 36.3.

Example 31 methyl N-(N-4-methyl-benzoyl-L-tyrosyl)-L-phenylalaninate

Spectra Data: mp 190.0-192.5° C.; ¹H-NMR (DMSO, 400 MHz): δ 9.14 (1H, s, Ar—OH), 8.46 (1H, d, J=7.2 Hz, NHCO), 8.36 (1H, d, J=8.4 Hz, NHCO), 7.67 (2H, d, J=8.8 Hz, H-3", 7"), 7.27-7.14 (7H, m, H-5'-9', 4", 6"), 7.09 (2H, d, J=8.4 Hz, H-5, 9), 6.60 (2H, d, J=8.4 Hz, H-6, 8), 4.63 (1H, m, H-2), 4.48 (1H, m, H-2'), 3.57 (3H, s, OCH₃), 3.06-2.78 (4H, m, H-3, 3'), 2.33 (3H, s, Ar—CH₃); ¹³C-NMR (DMSO, 100 MHz): δ 171.9 (s×2, C-1, 1'), 166.0 (C-1"), 155.7 (C-7), 141.2 (C-5"), 137.0 (C-4'), 131.3 (C-2"), 130.1 (C-5, 9), 129.1 (C-6', 8'), 128.7 (C-4", 6"), 128.33 (C-4), 128.28 (C-5', 9'), 127.4 (C-3", 7"), 126.6 (C-7'), 114.8 (C-6, 8), 54.8 (C-2), 53.7 (C-2'), 51.9 (OCH₃), 36.6, 36.2, 21.0 (Ar—CH₃).

Example 32

N-(N-3-nitro-benzoyl-L-tyrosyl)-L-phenylalaninol

Spectra Data: mp 225.5-227.0° C.; ¹H-NMR (DMSO, 400 MHz): δ 9.15 (1H, s, Ar—OH), 8.92 (1H, d, J=8.0 Hz, NHCO), 8.62 (1H, s, H-3"), 8.37 (1H, d, J=8.0 Hz, H-5"), 8.22 (1H, d, J=7.6 Hz, H-7"), 7.94 (1H, d, J=8.0 Hz, NHCO), 7.76 (1H, t, H-6"), 7.21-7.08 (7H, m, H-5'-9', 5, 9), 6.61 (2H, d, J=8.0 Hz, H-6, 8), 4.80 (1H, t, OH), 4.64 (1H, m, H-2), 3.89 (1H, m, H-2'), 3.33-3.25 (2H, m, H-1'), 2.96-2.62 (4H, m, H-3, 3'); ¹³C-NMR (DMSO, 100 MHz): δ 170.7 (C-1), 163.9 (C-1"), 155.7 (C-7), 147.6 (C-4"), 139.0 (C-4'), 135.6 (C-2"), 133.9 (C-7"), 130.1 (C-5, 9), 130.0 (C-6"), 129.1 (C-6', 8'), 128.2 (C-4), 128.0 (C-5', 9'), 125.8 (C-7', C-5"), 122.2 (C-3"), 114.8 (C-6, 8), 62.2 (C-1'), 55.3 (C-2), 52.5 (C-2'), 36.5, 36.4.

Example 33 methyl N-(N-benzoyl-L-tyrosyl)-L-phenylalaninate

Spectra Data: mp 200.0-202.0° C.; ¹H-NMR (DMSO, 400 MHz): δ 9.19 (1H, s, Ar—OH), 8.52-8.47 (2H, m, NHCO×2), 7.76 (2H, d, J=6.8 Hz, H-3", 7"), 7.50 (1H, t, H-5"), 7.43 (2H, t, H-4", 6"), 7.25-7.18 (5H, m, H-5'-9'), 7.10 (2H, d, J=8.4 Hz, H-5, 9), 6.61 (2H, d, J=8.4 z, H-6, 8), 4.63 (1H, m, H-2), 3.78 (1H, m, H-2'), 3.57 (3H, s, OCH₃), 3.07-2.78 (4H, m, H-3,3'); ¹³C-NMR (DMSO, 100 MHz): δ 171.93, 171.89, 166.2 (C-1"), 155.7 (C-7), 137.1 (C-4'), 134.1 (C-2"), 131.4 (C-5"), 130.2 (C-5, 9), 129.2 (C-6', 8'), 128.4 (×3, C-4", 6", C-4), 128.3 (C-5', 9'), 127.5 (C-3", 7"), 126.7 (C-7'), 114.9 (C-6, 8), 54.9 (C-2), 53.8 (C-2'), 52.0 (OCH₃), 36.6, 36.2.

Example 34 methyl N-[N-(4-acetamido-benzoyl)-L-phenylalanyl]-L-phenylalaninate

Spectra Data: mp 208.0-209.5° C.; ¹H-NMR (DMSO, 400 MHz): δ 10.16 (1H, s, ArNHCO), 8.51 (1H, d, J=7.2 Hz, NHCO), 8.40 (1H, d, J=8.4 Hz, NHCO), 7.73 (2H, d, J=8.8 Hz, H-3", 7"), 7.61 (2H, d, J=8.8 Hz, H-4", 6"), 7.33-7.14 (10H, m, H-5-9, 5'-9'), 4.72 (1H, m, H-2), 4.50 (1H, m, H-2'), 3.57 (3H, s, OCH₃), 3.07-2.90 (4H, m, H-3, 3'), 2.05 (3H, CH₃CO); ¹³C-NMR (DMSO, 100 MHz): δ 171.9, 171.8, 168.7 (ArNHCO), 165.6 (C-1"), 142.0 (C-5"), 138.4 (C-4'), 137.0 (C-4'), 129.2 (×2), 129.1 (×2), 128.3 (×4), 128.2 (C-2"), 128.1 (×2), 126.6 (C-7'), 126.2 (C-7), 118.0 (C-4", 6"), 54.4 (C-2), 53.7 (C-2'), 51.9 (OCH₃), 37.0 (C-3), 36.6 (C-3'), 24.1 (CH₃CO).

Example 35

N-[N-(4-chloroacetamido-benzoyl)-L-phenylalanyl]-L-phenylalaninol

Spectra Data: ¹H-NMR (DMSO, 400 MHz): δ 10.55 (1H, s, ArNHCO), 8.42 (1H, d, J=8.4 Hz, NHCO), 7.90 (1H, d, J=8.0 Hz, NHCO), 7.81 (2H, d, J=8.8 Hz, H-3", 7"), 7.66 (2H, d, J=8.8 Hz, H-4", 6"), 7.33-7.12 (10H, m, H-5-9, 5'-9'), 4.83 (1H, t, OH), 4.68 (1H, m, H-2), 4.31 (2H, COCH₂Cl), 3.91 (1H, m, H-2'), 3.36-3.26 (2H, m, H-2'), 3.06-2.93 (2H, m, H-3), 2.88 (1H, dd, J=6.0, 13.6 Hz, H-3'a), 2.68 (1H, dd, J=7.6, 13.6 Hz, H-3'b); ¹³C-NMR (DMSO, 100 MHz): δ 171.0 (C-1), 165.4 (C-1"), 165.0 (ArNHCO), 141.1 (C-5"), 139.0 (C-4'), 138.4 (C-4), 129.2 (×4, C-6, 8, 6', 8'), 129.1 (C-2"), 128.4 (C-3", 7"), 128.1 (×2), 128.0 (×2), 126.2 (C-7), 125.9 (C-7'), 118.4 (C-4", 6"), 62.2 (C-1'), 54.8 (C-2), 52.5 (C-2'), 37.3 (C-3), 36.4 (C-3').

Example 36 methyl N-[N-(4-acetamido-benzoyl)-L-phenylalanyl]-L-tyrosinate

Spectra Data: mp 215.5-217.0° C.; ¹H-NMR (DMSO, 400 MHz): δ 10.23 (1H, s, ArNHCO), 9.26 (1H, s, ArOH), 8.47-8.43 (2H, m, NHCO×2), 7.73 (2H, d, J=8.4 Hz, H-3", 7"), 7.62 (2H, d, J=8.4 Hz, H-4", 6"), 7.32 (2H, d, J=7.2 Hz, H-5, 9), 7.23 (2H, t, H-6, 8), 7.14 (1H, t, H-7), 6.99 (2H, d, J=8.4 Hz, H-5', 9'), 6.62 (2H, d, J=8.0 Hz, H-6', 8'), 4.71 (1H, m, H-2), 4.40 (1H, m, H-2'), 3.56 (3H, S, OCH₃), 3.07-2.86 (4H, m, H-3, 3'), 2.05 (3H, CH₃CO); ³C-NMR (DMSO, 100 MHz): δ 172.0, 171.7, 168.7 (ArNHCO), 165.7 (C-1"), 156.1 (C-7'), 142.0 (C-5"), 138.4 (C-4), 130.1 (C-5', 9'), 129.2 (C-6, 8), 128.3 (C-3", 7"), 128.2 (C-2"), 128.0 (C-5, 9), 127.0 (C-2"), 126.2 (C-7), 117.9 (C-4', 6"), 115.1 (C-6', 8'), 54.5 (C-2), 54.1 (C-2'), 51.8 (OCH₃), 36.9 (C-3), 35.9 (C-3'), 24.1 (CH₃CO).

Example 37 methyl N-[N-(4-propionamido-benzoyl)-L-phenylalanyl]-L-phenylalaninate

Spectra Data: mp 225.0-227.0° C.; ¹H-NMR (DMSO, 400 MHz): δ 10.09 (1H, s, ArNHCO), 8.52 (1H, d, J=7.6 Hz, NHCO), 8.40 (1H, d, J=8.4 Hz, NHCO), 7.74 (2H, d, J=8.4 Hz, H-3", 7"), 7.64 (2H, d, J=8.8 Hz, H-4", 6"), 7.34-7.13 (10H, m, H-5-9, 5'-9'), 4.73 (1H, m, H-2), 4.52 (1H, m, H-2'), 3.59 (3H, s, OCH₃), 3.08-2.91 (4H, m, H-3, 3'), 2.35 (2H, q, J=7.2 Hz, COCH₂CH₃), 1.08 (3H, t, J=7.6 Hz, COCH₂CH₃); ¹³C-NMR (DMSO, 100 MHz): δ 172.4, 171.82, 171.78, 165.7 (C-1"), 142.1 (C-5"), 138.4 (C-4), 137.0 (C-4'), 129.2 (×2), 129.1 (×2), 128.3 (×4, C-3", 7", 5', 9'), 128.1 (C-2"), 128.0 (C-5, 9), 126.6 (C-7), 126.2 (C-7'), 118.0 (C-4", 6"), 54.4 (C-2), 53.7 (C-2'), 51.9 (OCH₃), 36.9 (C-3), 36.6 (C-3'), 29.6 (COCH₂CH₃), 9.5 (COCH₂CH₃).

Example 38 methyl N-[N-(4-propionamido-benzoyl)-L-phenylalanyl]-4-nitro-L-phenylalaninate

Spectra Data: mp 221.0-223.0° C.; ¹H-NMR (DMSO, 400 MHz): δ 10.14 (1H, s, ArNHCO), 8.61 (1H, d, J=7.2 Hz, NHCO), 8.42 (1H, d, J=8.4 Hz, NHCO), 9.05 (2H, d, J=8.0 Hz, H-6', 8'), 7.72 (2H, d, J=7.6 Hz, H-3", 7"), 7.63 (2H, d, J=8.4 Hz, H-5', 9'), 7.51 (2H, d, J=8.0 Hz, H-4", 6"), 7.31 (2H, d, J=7.2 Hz, H-5, 9), 7.23 (2H, t, H-6, 8), 7.14 (1H, t J=7.2 Hz, H-7), 4.68-4.59 (2H, m, H-2, 2'), 3.61 (3H, s, OCH₃), 3.25-2.90 (4H, m, H-3, 3'), 2.34 (2H, q, J=7.6 Hz, COCH₂CH₃), 1.07 (3H, t, J=7.6 Hz, COCH₂CH₃); ¹³C-NMR (DMSO, 100 MHz): δ 172.4 (ArNHCO), 171.8 (C-1), 171.4 (C-1'), 165.7 (C-1"), 146.3 (C-7'), 145.5 (C-4'), 142.2 (C-5"), 138.3 (C-4), 130.6 (C-5', 9'), 129.2 (C-6, 8), 128.3 (C-3", 7"), 128.1 (C-5, 9), 128.0 (C-2"), 126.3 (C-7), 123.2 (C-6', 8'), 117.9 (C-4", 6"), 54.5 (C-2), 52.9 (C-2'), 52.1 (OCH$_3$), 36.8 (C-3), 36.2 (C-3'), 29.6 (COCH$_2$CH$_3$), 9.6 (COCH$_2$$_{CH3}$).

Example 39

N-[N-(4-acetamido-benzoyl)-L-phenylalanyl]-L-phenylalaninol

Spectra Data: mp 193.0-195.0° C.; $^1$H-NMR (DMSO, 400 MHz): δ 10.16 (1H, s, ArNHCO), 8.39 (1H, d, J=8.4 Hz, NHCO), 8.26 (1H, d, J=8.4 Hz, NHCO), 7.76 (2H, d, J=8.4 Hz, H-3", 7"), 7.62 (2H, d, J=8.8 Hz, H-4", 6"), 7.32-7.13 (10H, m, H-5-9, 5'-9'), 4.70 (1H, m, H-2), 4.17 (1H, m, H-2'), 3.64 (1H, dd, J=4.8, 11.2 Hz, H-1'a), 3.52 (1H, dd, J=7.0, 11.2 Hz, H-1'b), 3.05-2.78 (4H, m, H-3, 3'), 2.06 (3H, CH$_3$CO); $^{13}$C-NMR (DMSO, 100 MHz): δ 171.4 (C-1), 168.7 (ArNHCO), 165.6 (C-1"), 142.0 (C-5"), 138.3 (C-4), 137.8 (C-4'), 129.2 (×4), 128.3 (×4), 128.2 (C-2"), 128.0 (C-3", 7"), 126.4 (C-7), 126.2 (C-7'), 118.0 (C-4", 6"), 54.7 (C-2), 51.5 (C-1'), 46.8 (C-2'), 37.3 (C-3), 37.0 (C-3'), 24.1 (CH$_3$CO).

Example 40

N-[N-(4-acetamido-benzoyl)-L-tyrosyl]-L-phenylalaninol;

Spectra Data: mp 220.5-223.0° C.; $^1$H-NMR (DMSO, 400 MHz): δ 10.17 (1H, s, ArNHCO), 9.14 (1H, s, ArOH), 8.28 (1H, d, J=8.0 Hz, NHCO), 7.83 (1N, d, J=8.4 Hz, NHCO), 7.76 (2H, d, J=8.8 Hz, H-3", 7"), 7.63 (2H, d, J=8.4 Hz, H-4", 6"), 7.22-7.07 (7H, m, H-5, 9, 5'-9'), 6.61 (2H, d, J=8.0 Hz, H-6, 8), 4.81 (1H, t, OH), 4.57 (1H, m, H-2), 3.88 (1H, m, H-2'), 3.34-3.25 (2H, m, H-1'), 2.91-2.50 (4H, m, H-3, 3'), 2.07 (3H, CH$_3$CO); $^{13}$C-NMR (DMSO, 100 MHz): δ 171.2 (C-1), 168.7 (ArNHCO), 165.5 (C-1"), 155.7 (C-7), 142.0 (C-5"), 139.0 (C-4'), 130.1 (C-5, 9), 129.2 (6', 8'), 128.4 (C-4, 2"), 128.3 (C-5', 9'), 128.1 (C-3", 7"), 125.9 (C-7'), 117.9 (C-4", 6"), 114.8 (C-6, 8), 62.2 (C-1'), 55.1 (C-2), 52.4 (C-2'), 36.5, 36.4, 24.2 (CH$_3$CO).

Example 41 methyl N-[N-(4-acetamido-benzoyl)-L-tyrosyl]-L-phenylalaninate

Spectra Data: mp 225.0-226.0° C.; $^1$H-NMR (DMSO, 400 MHz): δ 10.18 (1H, s, ArNHCO), 9.16 (1H, s, ArOH), 8.48 (1H, d, J=7.2 Hz, NHCO), 8.34 (1H, d, J=8.4 Hz, NHCO), 7.75 (2H, d, J=8.8 Hz, H-3", 7"), 7.63 (2H, d, J=8.8 Hz, H-4", 6"), 7.26-7.17 (5H, m, H-5'-9'), 7.11 (2H, d, J=8.4 Hz, H-5, 9), 6.63 (2H, d, J=8.4 Hz, H-6, 8), 4.64 (1H, m, H-2), 4.50 (1H, m, H-2'), 3.58 (3H, s, OCH$_3$), 3.08-2.79 (4H, m, H-3, 3'), 2.07 (3H, CH$_3$CO); $^{13}$C-NMR (DMSO, 100 MHz): δ 171.9, 171.8, 168.7 (ArNHCO), 165.5 (C-1"), 155.7 (C-7), 142.0 (C-5"), 137.0 (C-4'), 130.1 (C-5, 9), 129.1 (C-6', 8'), 128.4 (C-4, 2"), 128.3 (×4, C-5', 9', 3", 7"), 126.6 (C-7'), 117.9 (C-4", 6"), 114.8 (C-6, 8), 54.8 (C-2), 53.7 (C-2'), 51.9 (OCH$_3$), 36.6, 36.2, 24.1 (CH$_3$CO).

Example 42 methyl N-[N-(4-chloroacetamido-benzoyl)-L-phenylalanyl]-L-phenylalaninate

Spectra Data: mp 222.5-224.5° C.; $^1$H-NMR (DMSO, 400 MHz): δ 10.64 (1H, s, ArNHCO), 8.57 (1H, d, J=7.6 Hz, NHCO), 8.50 (1H, d, J=8.4 Hz, NHCO), 7.78 (2H, d, J=8.4 Hz, H-3", 7"), 7.65 (2H, d, J=8.8 Hz, H-4", 6"), 7.34-7.14 (10H, m, H-5-9, 5'-9'), 4.74 (1H, m, H-2), 4.51 (1H, m, H-2'), 4.31 (2H, s, NHCOCH$_2$Cl), 3.59 (3H, s, OCH$_3$), 3.09-2.92 (4H, m, H-3, 3'); $^{13}$C-NMR (DMSO, 100 MHz): δ 171.9, 171.8, 165.6 (C-1"), 165.0 (ArNHCO), 141.2 (C-5"), 138.4 (C-4), 137.1 (C-4'), 129.2 (C-6, 8), 129.1 (C-6', 8'), 129.0 (C-2"), 128.4 (C-3", 7"), 128.3 (C-5', 9'), 128.1 (C-5, 9), 126.6 (C-7'), 126.2 (C-7), 118.4 (C-4", 6"), 54.5 (C-2), 53.8 (C-2'), 51.9 (OCH$_3$), 43.6 (COCH$_2$Cl), 37.0 (C-3), 36.6 (C-3').

Example 43

N-(N-isonicotinyl-L-phenylalanyl)-L-phenylalaninol

Spectra Data: N-(N-4-pyridinyl-formyl-L-phenylalanyl)-L-phenylalanol, mp 199.0-201.0° C.; $^1$H-NMR (DMSO, 400 MHz): δ 8.83 (1H, d, J=8.8 Hz, NHCO), 8.69 (2H, d, J=6.4 Hz, H-4", 6"), 7.96 (1H, d, J=8.0 Hz, NHCO), 7.66 (2H, d, J=6.0 Hz, H-3", 7"), 7.31-7.11 (10H, m, H-5-9, 5'-9'), 4.81 (1H, t, J=5.2 Hz, OH), 4.68 (1H, m, H-2), 3.89 (1H, m, H-2'), 3.35-3.25 (2H, m, H-1'), 3.04 (1H, dd, J=4.4, 14.0 Hz, H-3a), 2.95-2.83 (2H, m, H-3b, 3'a), 2.65 (1H, dd, J=7.6, 13.2 Hz, H-3'b); $^{13}$C-NMR (DMSO, 100 MHz): δ 170.5 (C-1), 164.5 (C-1"), 150.1 (C-4", 6"), 141.0 (C-2"), 139.0 (C-4'), 138.2 (C-4), 129.2 (×4, C-6, 8, 6', 8'), 128.1 (×4, C-5, 9, 5', 9'), 126.3 (C-7), 125.9 (C-7'), 121.4 (C-3", 7"), 62.2 (C-1'), 54.8 (C-2), 52.5 (C-2'), 37.3 (C-3), 36.4 (C-3').

Example 44 methyl N-(N-isonicotinyl-L-phenylalanyl)-L-phenylalaninate

Spectra Data: mp 174.0-175.0° C.; $^1$H-NMR (CDCl$_3$, 400 MHz): δ 8.71 (2H, d, J=6.0 Hz, H-4", 6"), 7.52 (2H, d, J=5.6 Hz, H-3", 7"), 7.31-7.17 (8H, m, H-5, 6, 8, 9, 5', 6', 8', 9'), 7.07 (1H, br, NHCO), 6.99-6.97 (2H, m, H-7, 7'), 6.30 (1H, br, NHCO), 4.86-4.75 (2H, m, H-2, 2'), 3.72 (3H, s, OCH$_3$), 3.20 (1H, dd, J=6.0, 14.0 Hz, H-3a), 3.14-3.08 (2H, m, H-3b, 3'a), 2.97 (1H, dd, J=7.6, 13.6 Hz, H-3'b); $^{13}$C-NMR (CDCl$_3$, 100 MHz): δ 171.2 (C-1), 170.0 (C-1'), 165.0 (C-1"), 150.6 (C-4", 6"), 140.7 (C-2"), 136.0, 135.3, 129.3 (C-6', 8'), 129.0 (C-6, 8), 128.7 (C-5', 9'), 128.6 (C-5, 9), 127.24, 127.19, 120.8 (C-3", 7"), 54.6 (C-2), 53.5 (C-2'), 52.4 (OCH$_3$), 38.2 (C-3), 37.8 (C-3').

Example 45 methyl N-(N-isonicotinyl-L-phenylalanyl)-4-nitro-L-phenylalaninate

Spectra Data: mp 224.5-225.5° C.; $^1$H-NMR (CDCl$_3$, 400 MHz): δ 8.77 (2H, s, H-4", 6"), 8.06 (2H, d, J=8.0 Hz, H-6', 8'), 7.54 (2H, s, H-3", 7"), 7.29-7.19 (7H, m, H-5-9, 5', 9'), 6.86 (1H, br, NHCO), 6.29 (1H, br, NHCO), 4.79 (2H, m, H-2, 2'), 3.72 (3H, s, OCH$_3$), 3.21-3.08 (4H, m, H-3, 3'); $^{13}$C-NMR (DMSO, 100 MHz): δ 170.5 (C-1), 170.1 (C-1'), 165.2 (C-1"), 150.7 (C-4", 6"), 147.1 (C-7'), 143.2 (C-4'), 140.4 (C-2"), 135.7 (C-4), 130.1 (C-5', 9'), 129.2 (C-6, 8), 128.9 (C-5, 9), 124.4 (C-7), 123.7 (C-6', 8'), 120.7 (C-3", 7"), 54.8 (C-2'), 53.0 (C-2), 52.7 (OCH$_3$), 38.1 (C-3'), 37.1 (C-3).

Example 46 methyl N-(N-isonicotinyl-L-phenylalanyl)-L-tyrosinate

Spectra Data: mp 216.0-217.0° C.; $^1$H-NMR (DMSO, 400 MHz): δ 9.26 (1H, s, Ar—OH), 8.91 (1H, d, J=8.8 Hz, NHCO), 8.70 (2H, d, J=5.2 Hz, H-4", 6"), 8.57 (1H, d, J=7.6 Hz, NHCO), 7.66 (2H, d, J=5.2 Hz, H-3", 7"), 7.35 (2H, d, J=7.6 Hz, H-5, 9), 7.25 (2H, t, H-6, 8), 7.16 (1H, t, H-7), 7.02 (2H, d, J=8.0 Hz, H-5', 9'), 6.64 (2H, d, J=8.0 Hz, H-6', 8'), 4.78 (1H, m, H-2), 4.44 (1H, m, H-2'), 3.59 (3H, S, OCH$_3$), 3.12-2.85 (4H, m, H-3, 3'); $^{13}$C-NMR (DMSO, 100 MHz): δ 172.0 (C-1), 171.3 (C-1'), 164.7 (C-1"), 156.1 (C-7'), 150.2 (C-4", 6"), 140.9 (C-2"), 138.1 (C-4), 130.1 (C-5', 9'), 129.2 (C-6, 8), 128.1 (C-5, 9), 127.0 (C-4'), 126.3 (C-7), 121.4 (C-3", 7"), 115.1 (C-6', 8'), 54.5 (C-2), 54.2 (C-2'), 51.9 (OCH$_3$), 37.0 (C-3), 35.8 (C-3').

Example 47

N-(N-isonicotinyl-L-tyrosyl)-L-phenylalaninol

Spectra Data: mp 210.0-212.0° C.; $^1$H-NMR (DMSO, 400 MHz): δ 9.17 (1H, s, ArOH), 8.79 (1H, d, J=8.4 Hz, NHCO), 8.71 (2H, d, J=5.6 Hz, H-4", 6"), 7.95 (1H, d, J=8.0 Hz, NHCO), 7.69 (2H, d, J=5.6 Hz, H-3", 7"), 7.23-7.09 (7H, m, H-5, 9, 5'-9'), 6.63 (2H, d, J=8.4 Hz, H-6, 8), 4.82 (1H, t, OH), 4.62 (1H, m, H-2), 3.90 (1H, m, H-2'), 3.37-3.27 (2H, m, H-1'), 2.96-2.79 (3H, m, H-3, 3'a), 2.66 (1H, dd, J=8.0, 13.6 Hz, H-3'b); $^{13}$C-NMR (DMSO, 100 MHz): δ 171.7 (C-1), 164.5 (C-1"), 155.7 (C-7), 150.2 (C-4", 6"), 141.1 (C-2"), 139.0 (C-4'), 130.1 (C-5, 9), 129.2 (C-6', 8'), 128.2 (C-4), 128.1 (C-5', 9'), 125.9 (C-7'), 121.4 (C-3", 7"), 114.9 (C-6, 8), 62.3 (C-1'), 55.3 (C-2), 52.5 (C-2'), 36.6, 36.4.

Example 48 methyl N-(N-isonicotinyl-L-tyrosyl)-L-phenylalaninate

Spectra Data: mp 206.5-209.0° C.; $^1$H-NMR (DMSO, 400 MHz): δ 9.17 (1H, s, ArOH), 8.82 (1H, d, J=8.8 Hz, NHCO), 8.70 (2H, d, J=5.6 Hz, H-4", 6"), 8.59 (1H, d, J=7.6 Hz, NHCO), 7.67 (2H, d, J=5.6 Hz, H-3", 7"), 7.27-7.18 (5H, m, H-5'-9'), 7.12 (2H, d, J=8.4 Hz, H-5, 9), 6.63 (2H, d, J=8.4 Hz, H-6, 8), 4.68 (1H, m, H-2), 4.50 (1H, m, H-2'), 3.59 (3H, s, OCH$_3$), 3.09-2.77 (4H, m, H-3, 3); $^{13}$C-NMR (DMSO, 100 MHz): δ 171.8 (C-1), 171.4 (C-1'), 164.6 (C-1"), 155.7 (C-7), 150.2 (C-4", 6"), 141.0 (C-2"), 137.1 (C-4'), 130.1 (C-5, 9), 129.1 C-6', 8'), 128.3 (C-5', 9'), 128.1 (C-4), 126.6 (C-7'), 121.4 (C-3", 7"), 114.9 (C-6, 8), 54.9 (C-2), 53.8 (C-2'), 51.9 (OCH$_3$), 38.9, 36.5.

Example 49

N-[N-(4-dimethylaminomethyl-benzoyl)-L-phenylalanyl]-L-phenylalaninol

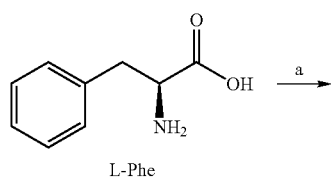

L-Phe

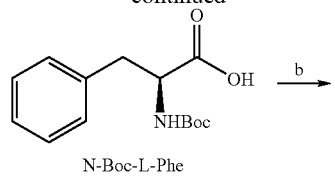

N-Boc-L-Phe

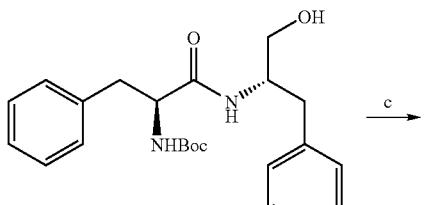

M-32

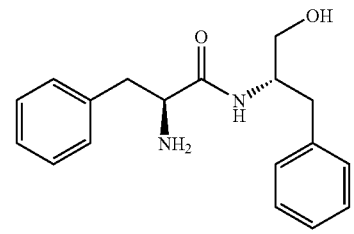

M-33

Reagents and Reaction Conditions:
(a) (t-BuOCO)$_2$O, 1.0 M NaOH, TBAB;
(b) CH$_2$Cl$_2$, isobutyl chloroformate (IBCF), N-methylmorpholine (NMM), −5° C.; and
(c) TFA, CH$_2$Cl$_2$, rt., 2 hours.

Preparation Procedures:
(a) L-phenylalanine (1.65 g, 10.0 mmol) was dissolved in 1.0 M NaOH (20 ml). To the solution were added di-t-butyl dicarbonate (2.289 g, 10.05 mmol) and tetrabutylammonium bromide (1.0 g). The resulting solution was stirred at room temperature overnight and was adjusted with concentrated hydrochloric acid to pH 2-3 on the morrow. The solution was extracted with ethyl acetate (60 ml) and washed with saturated aqueous sodium chloride (2×20 ml) and dried over anhydrous sodium sulfate. The solution was evaporated under reduced pressure to dryness to recover the solvents, giving N-BOC-L-phenylalanine (N-BOC-L-Phe) (2.63 g, 99%) as a colorless oil.
(b) Following the similar preparation process as that in synthesis step (b) of Example 1, an intermediate M-32 was prepared (88%) as a white powder.
(c) M-32 prepared in the previous step was dissolved in trifluoroacetic acid (TFA). The solution was stirred at room temperature over 2 hours. To the reaction flask was added suitable amount of water. The pH of the solution was adjusted with sodium carbonate to basicity (pH 11-12). The resulting solution was extracted with ethyl acetate. The organic phase was dried over anhydrous sodium sulfate. The solution was evaporated under reduced pressure to dryness to recover the solvents, giving a solid product M-33 as a white wax (65.8%).

N-[N-(4-dimethylaminomethyl-benzoyl)-L-phenylalanyl]-L-phenylaninol

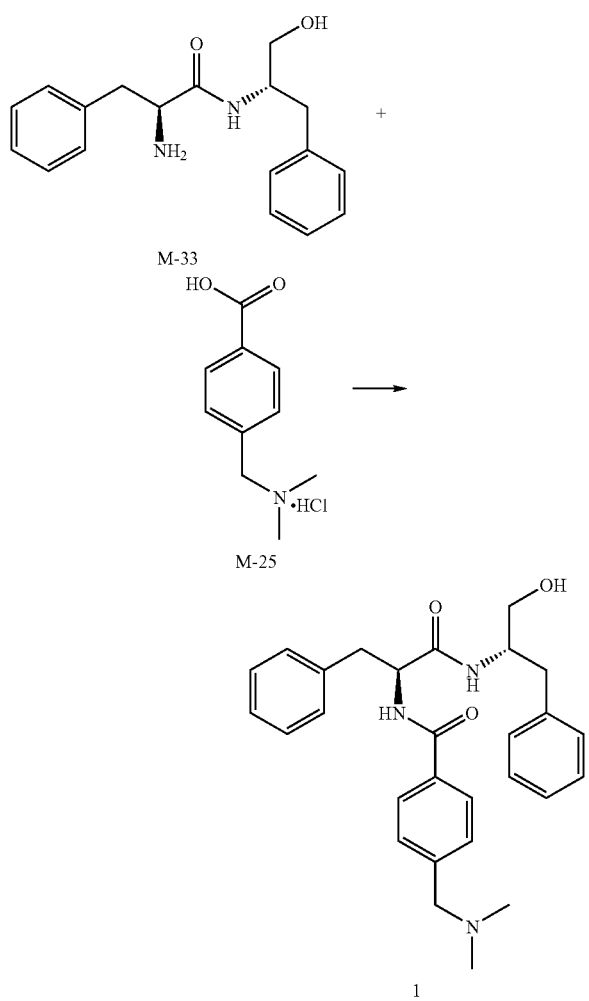

Reagents and Reaction Conditions:
$CH_2Cl_2$, DCC, DMAP, rt.

Preparation Procedures:
In a reaction flask were added the intermediates M-25 (10 mmol) and M-33 (10 mmol), DCC (2.47 g□12 mmol) and DMAP (200 mg, as catalyst). To the reaction flask was added anhydrous $CH_2Cl_2$ (200 ml). The reaction was stirred at room temperature overnight under nitrogen. The product was purified with extraction and recrystallization to give a solid product 1 (89%) as a white wax.

Spectra Data: mp 196.5-198.0° C.; $^1$H-NMR (DMSO, 400 MHz): δ 8.46 (1H, d, J=8.8 Hz, NHCO), 7.87 (1H, d, J=8.4 Hz, NHCO), 7.75 (2H, d, J=8.0 Hz, H-3", 7"), 7.34 (2H, d, J=8.0 Hz, H-4", 6"), 7.30-7.10 (10H, m, H-5'-9', 5-9), 4.81 (1H, t, OH), 4.67 (1H, m, H-2), 3.87 (1H, m, H-2'), 3.43 (2H, s, ArCH$_2$N(CH$_3$)$_2$), 3.34-3.25 (2H, m, H-1'), 3.02-2.93 (2H, m, H-3), 2.84 (1H, dd, J=5.6, 13.6 Hz, H-3'a), 2.65 (1H, dd, J=8.4, 13.6 Hz, H-3'b), 1.14 (6H, s, ArCH$_2$N(CH$_3$)$_2$); $^{13}$C-NMR (DMSO, 100 MHz): δ 171.0 (C-1), 165.9 (C-1"), 143.0 (C-5"), 139.0 (C-4'), 138.4 (C-4), 132.8 (C-2"), 129.2 (×4, C-6, 8, 6', 8'), 128.5 (C-4", 6"), 128.1 (C-5', 9'), 128.0 (C-5, 9), 127.4 (C-3", 7"), 126.2 (C-7), 125.9 (C-7'), 62.8 (ArCH$_2$N (CH$_3$)$_2$), 62.2 (C-1'), 54.8 (C-2), 52.5 (C-2'), 44.9 (ArCH$_2$N (CH$_3$)$_2$), 37.2, 36.4.

Following the similar synthetic process as that in example 49, derivatives of examples 50-53 were prepared, respectively, through selecting appropriate reaction materials and intermediates.

Example 50

N-{N-[4-(1-pyrrolidyl)methyl-benzoyl]-L-phenylalanyl}-L-phenylalaninol

Spectra Data: mp 164.0-165.0° C.; $^1$H-NMR (DMSO, 400 MHz): δ 8.44 (1H, d, J=8.0 Hz, NHCO), 7.87 (1H, d, J=8.4 Hz, NHCO), 7.74 (2H, d, J=8.4 Hz, H-3", 7"), 7.35 (2H, d, J=8.0 Hz, H-4", 6"), 7.31-7.09 (10H, m, H-5'-9', 5-9), 4.81 (1H, t, OH), 4.67 (1H, m, H-2), 3.88 (1H, m, H-2'), 3.58 (2H, s, ArCH$_2$N<), 3.34-3.24 (2H, m, H-1'), 3.04-2.91 (2H, m, H-3), 2.85 (1H, dd, J=5.6, 13.6 Hz, H-3'a), 2.65 (1H, dd, J=8.0, 13.6 Hz, H-3'b), 2.40 (4H, s, ArCH$_2$N(CH$_2$)$_2$), 1.67 (4H, s, >NCH$_2$CH$_2$CH$_2$CH$_2$N<); $^{13}$C-NMR (DMSO, 100 MHz): δ 171.0 (C-1), 165.9 (C-1"), 143.0 (C-5"), 139.0 (C-4'), 138.4 (C-4), 132.6 (C-2"), 129.2 (×4, C-6, 8, 6', 8'), 128.14 (C-4", 6"), 128.08 (C-5', 9'), 128.04 (C-5, 9), 127.4 (C-3", 7"), 126.2 (C-7), 125.9 (C-7'), 62.2 (C-1'), 59.2 (ArCH$_2$N<), 54.8 (C-2), 53.5 (ArCH$_2$N(CH$_2$)$_2$), 52.5 (C-2'), 37.2, 36.4, 23.1 (>NCH$_2$CH$_2$CH$_2$CH$_2$N<).

Example 51

N-{N-[4-(4-morpholinyl)methyl-benzoyl]-L-phenylalanyl}-L-phenylalaninol

Spectra Data: mp 183.0-184.5° C.; $^1$H-NMR (DMSO, 400 MHz): δ 8.45 (1H, d, J=8.4 Hz, NHCO), 7.87 (1H, d, J=8.0 Hz, NHCO), 7.76 (2H, d, J=7.6 Hz, H-3", 7"), 7.37 (2H, d, J=7.6 Hz, H-4", 6"), 7.31-7.10 (10H, m, H-5'-9', 5-9), 4.81 (1H, t, OH), 4.69 (1H, m, H-2), 3.89 (1H, m, H-2'), 3.57 (4H, s,-CH$_2$OCH$_2$—), 3.48 (2H, s, ArCH$_2$N<), 3.34-3.25 (2H, m, H-1'), 3.05-2.92 (2H, m, H-3), 2.86 (1H, dd, J=5.2, 13.6 Hz, H-3'a), 2.66 (1H, dd, J=8.0, 13.6 Hz, H-3'b), 2.34 (4H, s, ArCH$_2$N(CH$_2$)$_2$); $^{13}$C-NMR (DMSO, 100 MHz): δ 170.9 (C-1), 165.9 (C-1"), 141.4 (C-5"), 139.0 (C-4'), 138.4 (C-4), 132.8 (C-2"), 129.19 (×2), 129.17 (×2), 128.6 (C-4", 6"), 128.06 (×2), 128.01 (×2), 127.4 (C-3", 7"), 126.2 (C-7), 125.9 (C-7'), 66.2 (—CH$_2$OCH$_2$—), 62.2 (C-1'), 61.96 (ArCH$_2$N<), 54.7 (C-2), 53.2 (ArCH$_2$N(CH$_2$)$_2$), 52.5 (C-2'), 37.2, 36.4.

Example 52

N-[N-(4-ethoxycarbonyl-benzoyl)-L-phenylalanyl]-L-phenylalaninol

Spectra Data: mp 188.0-189.5° C.; $^1$H-NMR (DMSO, 400 MHz): δ 8.74 (1H, d, J=8.4 Hz, NHCO), 8.02 (2H, d, J=8.0 Hz, H-4", 6"), 7.97 (1H, d, J=8.4 Hz, NHCO), 7.91 (2H, d, J=8.4 Hz, H-3", 7"), 7.33-7.11 (10H, m, H-5-9, 5'-9'), 4.82 (1H, t, OH), 4.71 (1H, m, H-2), 4.34 (2H, q, J=7.2 Hz, OCH$_2$CH$_3$), 3.90 (1H, m, H-2'), 3.35-3.26 (2H, m, H-1'), 3.07-2.92 (2H, m, H-3), 2.87 (1H, dd, J=5.6, 13.6 Hz, H-3'a), 2.67 (1H, dd, J=8.0, 13.6 Hz, H-3'b), 1.34 (3H, t, OCH$_2$CH$_3$); $^{13}$C-NMR (DMSO, 100 MHz): δ 171.8 (C-1), 165.2 (×2, C-1", ArCOOCH$_2$CH$_3$), 139.0 (C-4'), 138.3 (C-4), 138.1

(C-2"), 132.1 (C-5"), 129.2 (×4, C-6, 8, 6', 8'), 129.0 (C-4", 6"), 128.08 (×2), 128.05 (×2), 127.8 (C-3", 7"), 126.2 (C-7), 125.9 (C-7'), 62.2 (C-1'), 61.0 (OCH$_2$CH$_3$), 54.9 (C-2), 52.5 (C-2'), 37.3 (C-3), 36.4 (C-3'), 14.2 (OCH$_2$CH$_3$).

Example 53

N-[N-(2-carboxyl-benzoyl)-4-acetamido-L-phenylalanyl]-L-phenylalaninol sodium salt Spectra Data: $^1$H-NMR (DMSO, 400 MHz): δ 9.20 (1H, d, J=7.2 Hz, H-4"), 8.50 (1H, d, J=8.8 Hz, H-7"), 7.76 (1H, m, H-6"), 7.33-7.19 (12H, m, H-5-9, 5'-9', NHCO×2), 6.65 (1H, m, H-5"), 4.48-4.39 (2H, m, H-2, 2'), 3.80 (1H, br, OH), 3.45-3.27 (2H, m, H-1'), 2.86-2.70 (4H, m, H-3, 3'); $^{13}$C-NMR (DMSO, 100 MHz): δ 170.98, 170.94, 168.6 (C-1"), 139.6, 139.5, 138.4, 138.2, 129.3 (×2, C-4", 7"), 129.3 (C-6, 8), 129.0 (C-6', 8'), 128.2 (C-5, 9), 128.0 (C-5', 9'), 127.7 (C-5"), 126.0, 125.92, 125.87, 61.0 (C-1'), 54.7, 54.0, 36.6, 36.2.

Example 54

N-(N-benzoyl-4-acetamido-L-phenylalanyl)-O-acetyl-L-phenylalaninol

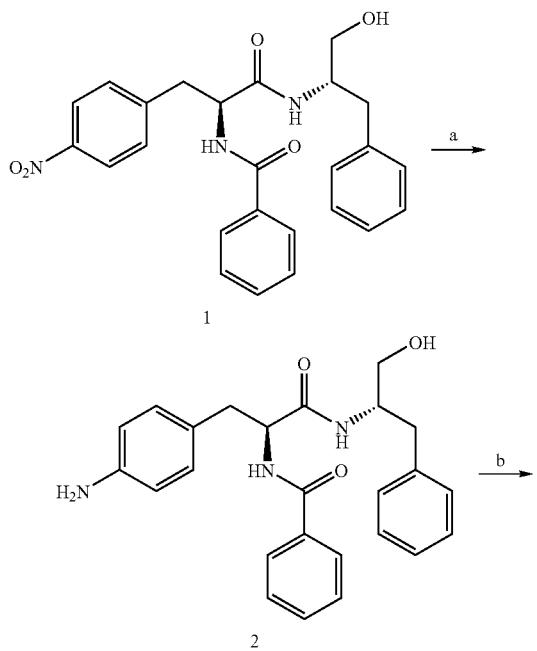

Reagents and Reaction Conditions:
(a) MeOH, H$_2$, Pd/C (20%), rt., 3 hours; and
(b) Ac$_2$O, pyridine (pyr.), rt., 5 hours.

Preparation Procedures:
(a) The previously prepared compound 1 (Example 5) (1.788 g, 4 mmol) was dissolved in MeOH (100 ml). The solution was degassed followed by adding 20% Pd/C (21 mg). After replacing the air in the reaction system with hydrogen, the reaction system was sealed with a hydrogen balloon and was stirred overnight at room temperature. The catalyst Pd/C was removed by filtering on the morrow. The filtrate was evaporated to dryness to recover the solvents, giving a crude compound 2 (1.876 g) as a white powder. The product was used in the next reaction step without further purification.

(b) The crude compound 2 (469 mg, <1.0 mmol) prepared in the previous step was fully dissolved in pyridine (5 ml). The solution was stirred at room temperature. To the solution was added slowly and dropwise acetic anhydride (Ac$_2$O) (2 ml). The reaction was kept at room temperature for 5 hours. To the reaction mixture was added absolute alcohol (5 ml) to decompose the excess acetic anhydride. The solution was evaporated to dryness to recover the solvents. The resulting solid was fully dissolved with a suitable amount of EtOAc. The solution was washed in turn with distilled water, 5% saturated aqueous NaHCO$_3$ and NaCl solution, and dried over anhydrous sodium sulfate. The solution was evaporated under reduced pressure to recover ethyl acetate. The resulting residue was recrystallized from ethyl acetate, giving a product (300 mg, 60.0%) as a white powder.

Spectra Data: mp 236.0-237.5° C.; $^1$H-NMR (DMSO, 400 MHz): δ 9.84 (1H, s, ArNHCO), 8.49 (1H, d, J=8.4 Hz, NHCO), 8.15 (1H, d, J=8.4 Hz, NHCO), 7.80 (2H, d, J=7.6 Hz, H-3", 7"), 7.52 (1H, t, H-5"), 7.47-7.43 (4H, m, H-4", 6", 6, 8), 7.24-7.15 (7H, m, H-5'-9', 5, 9), 4.63 (1H, m, H-2), 4.18 (1H, m, H-2'), 4.02 (1H, dd, J=4.8, 11.2 Hz, H-1'a), 3.87 (1H, dd, J=7.2, 11.2 Hz, H-1'b), 2.96-2.77 (4H, m, H-3, 3'), 1.99 (3H, CH$_3$CO), 1.98 (3H, CH$_3$CO); $^{13}$C-NMR (DMSO, 100 MHz): δ 171.2 (C-1), 170.3 (OCOCH$_3$), 168.1 (ArNH-COCH$_3$), 166.1 (C-1"), 138.0 (C-7), 137.6 (C-4'), 134.1 (C-2"), 132.8 (C-4), 131.3 (C-5"), 129.3 (C-5, 9), 129.2 (C-6', 8'), 128.23 (×2), 128.18 (×2), 127.4 (C-3", 7"), 126.2 (C-7'), 118.6 (C-6, 8), 64.6 (C-1'), 55.0 (C-2), 49.1 (C-2'), 36.7 (C-3'), 36.6 (C-3), 24.0 (NHCOCH$_3$), 20.6 (OCOCH$_3$).

Following the similar synthetic process as that in example 49, derivatives of examples 55-70 were prepared, respectively, through selecting appropriate reaction materials and intermediates.

Example 55

N-(N-benzoyl-L-phenylalanyl)-O-acetyl-L-phenylalaninol

Spectra Data: mp 186-187° C.; [α]$_D^{20}$ −35.71 (0.028, CHCl$_3$); IR (KBr) cm$^{-1}$: 3314, 1725, 1661, 1631, 1533, 746, 698; EI-MS m/z: 444, 384, 353, 311, 269, 252, 224, 172, 131, 105 (100), 91, 77, 60; $^1$H-NMR (CDCl$_3$, 400 MHz): δ 7.69 (2H, d, J=8.0 Hz, H-3", 7"), 7.50 (1H, t, H-5"), 7.42 (2H, t, H-4", 6"), 7.30-7.06 (10H, m, H-5-9, 5'-9'), 6.76 (1H, d, J=7.6 Hz, NHCO), 5.97 (1H, d, J=8.4 Hz, NHCO), 4.77 (1H, m, H-2), 4.34 (1H, m, H-2'), 3.93 (1H, dd, J=5.2, 11.6 Hz, H-1'a), 3.81 (1H, dd, J=4.0, 11.2 Hz, H-1'b), 3.22 (1H, dd, J=5.6, 13.6 Hz, H-3a), 3.06 (1H, dd, J=8.4, 13.6 Hz, H-3b), 2.75 (2H, m, H-3'), 2.03 (3H, s, CH$_3$CO); $^{13}$C-NMR (CDCl$_3$, 400 MHz): δ 170.6 (C-1), 170.2 (COCH$_3$), 167.1 (C-1"), 136.7 (C-4), 136.6 (C-4'), 133.6 (C-2"), 131.9 (C-5"), 129.3 (C-6, 8), 129.1 (C-6', 8'), 128.7 (C-4", 6"), 128.6 (C-5', 9'), 127.1

(C-3", 7"), 127.0 (C-7'), 126.7 (C-7), 64.5 (C-1'), 54.9 (C-2), 49.4 (C-2'), 38.4 (C-3), 37.4 (C-3'), 20.77 (COCH$_3$).

Example 56

N-(N-benzoyl-L-phenylalanyl)-O-(3-carboxyl-propionyl)-L-phenylaninol

Spectra Data: $^1$H-NMR (CDCl$_3$, 400 MHz): δ 8.61 (1 H, d, J=7.6 Hz, NHCO) 7.71 (2H, d, H-3", 7"), 7.50 (1H, t, H-5"), 7.40 (2, t, H-4", 6"), 7.31-7.08 (10H, m, H-5-9, 5'-9'), 6.47 (1H, d, J=8.0 Hz, NHCO), 5.12 (1H, m, H-2), 4.32 (1H, m, H-2'), 4.15-3.94 (2H, dd×2, H-3'), 3.05-3.01 (2H, m, H-3), 2.70-2.58 (4H, m,-OCOCH$_2$CH$_2$CO—).

Example 57 methyl N-(N-benzoyl-acetyl-L-phenylalanyl)-L-phenylalaninate

Spectra Data: mp 221.0-222.0° C.; $^1$H-NMR (DMSO, 400 MHz): δ 9.84 (1H, s, ArNHCO), 8.52 (2H, m, NHCO×2), 7.76 (2H, d, J=7.6 Hz, H-3", 7"), 7.51 (1H, t, H-5"), 7.46-7.42 (4H, m, H-4", 6", 6, 8), 7.26-7.17 (7H, m, H-5'-9', 5, 9), 4.71 (1H, m, H-2), 4.51 (1H, m, H-2'), 3.59 (3H, s, OCH$_3$), 3.09-2.85 (4H, m, 14-3, 3'), 1.99 (3H, CH$_3$CO); $^{13}$C-NMR (DMSO, 100 MHz): δ 171.9, 171.7, 168.1 (ArNHCOCH$_3$), 166.2 (C-1"), 137.6 (C-7'), 137.1 (C-4'), 134.0 (C-2"), 132.8 (C-4), 131.3 (C-5"), 129.4 (C-5, 9), 129.1 (C-6', 8'), 128.3 (C-4", 6"), 128.2 (C-5', 9'), 127.4 (C-3", 7"), 126.6 (C-7'), 118.6 (C-6, 8), 54.6 (C-2), 53.8 (C-2'), 51.9 (OCH$_3$), 36.6, 36.4, 24.0 (COCH$_3$).

Example 58 methyl N-(N-benzoyl-L-phenylalanyl)-4-amino-L-phenylalaninate hydrochloride

Spectra Data: mp 173.0-175.0° C.; $^1$H-NMR (DMSO, 400 MHz): δ 10.25 (br, ArNH$_2$.HCl), 8.69 (1H, d, J=7.6 Hz, NHCO), 8.62 (1H, d, J=8.8 Hz, NHCO), 7.77 (2H, d, J=6.8 Hz, H-3", 7"), 7.51-7.14 (12H, m, H-4"-6", 5-9, 5', 9', 6', 8'), 4.71 (1H, m, H-2), 4.50 (1H, m, H-2'), 3.58 (3H, s, OCH$_3$), 3.11-2.82 (4H, m, H-3, 3'); $^{13}$C-NMR (DMSO, 100 MHz): δ 171.9, 171.7, 166.3 (C-1"), 138.4 (C-4), 137.2 (C-7'), 134.0 (C-2"), 131.4 (C-5"), 130.6 (C-4'), 130.6 (C-5', 9'), 129.3 (C-6, 8), 128.3 (×2), 128.1 (×2), 127.5 (C-3", 7"), 126.3 (C-7'), 123.1 (C-6', 8'), 54.8 (C-2), 53.7 (C-2'), 52.1 (OCH$_3$), 37.0, 35.9.

Example 59 methyl N-(N-benzoyl-L-phenylalanyl)-4-acetamido-L-phenylalaninate

Spectra Data: mp 228.0-229.5° C.; $^1$H-NMR (DMSO, 400 MHz): δ 9.95 (1H, s, ArNHCO), 8.60 (1H, d, J=8.8 Hz, NHCO), 8.57 (1H, d, J=7.6 Hz, NHCO), 7.77 (2H, d, J=6.8 Hz, H-3", 7"), 7.53-7.14 (12H, m, H-4"-6", 5-9, 5', 9', 6', 8'), 4.74 (1H, m, H-2), 4.47 (1H, m, H-2'), 3.59 (3H, s, OCH$_3$), 3.09-2.91 (4H, m, H-3, 3'), 2.02 (3H, s, COCH$_3$); $^{13}$C-NMR (DMSO, 100 MHz): δ 171.9, 171.7, 168.2 (ArNHCOCH$_3$), 166.2 (C-1"), 138.4 (C-4), 138.0 (C-7'), 134.0 (C-2"), 131.4 (C-4'), 131.3 (C-5"), 129.4 (C-5', 9'), 129.2 (C-6, 8), 128.2 (C-4", 6"), 128.1 (C-5, 9), 127.4 (C-3", 7"), 126.2 (C-7'), 118.8 (C-6', 8'), 54.6 (C-2), 53.9 (OCH$_3$), 37.0, 36.1, 24.0 (COCH$_3$).

Example 60 methyl N-[N-(4-methyl-benzoyl)-L-phenylalanyl]-4-acetamido-L-phenylalaninate

Spectra Data: mp 221.5-222.0° C.; $^1$H-NMR (DMSO, 400 MHz): δ 9.91 (1H, s, ArNHCO), 8.53 (1H, d, J=7.6 Hz, NHCO), 8.48 (1H, d, J=8.8 Hz, NHCO), 7.68 (2H, d, J=8.8 Hz, H-3", 7"), 7.48 (2H, d, J=8.8 Hz, H-6', 8'), 7.34 (2H, d, J=7.6 Hz, H-5, 9), 7.24 (4H, m, H-4", 6", 6, 8), 7.16 (3H, m, H-5', 9', 7), 4.74 (1H, m, H-2), 4.48 (1H, m, H-2'), 3.59 (3H, s, OCH$_3$), 3.09-2.91 (4H, m, H-3, 3'), 2.33 (3H, s, Ar—CH$_3$), 2.02 (3H, s, COCH$_3$); $^{13}$C-NMR (DMSO, 100 MHz): δ 171.9, 171.8, 168.1 (ArNHCO), 166.1 (C-1"), 141.2 (C-5"), 138.4 (C-4), 138.0 (C-7'), 131.4 (C-2"), 131.2 (C-4'), 129.4 (C-5', 9'), 129.2 (C-6, 8), 128.7 (C-4", 6"), 128.0 (C-5, 9), 127.5 (C-3", 7"), 126.2 (C-7), 118.9 (C-6', 8'), 54.5 (C-2), 53.9 (C-2'), 37.0, 36.1, 24.0 (NHCOCH$_3$), 21.0 (Ar—CH$_3$).

Example 61

N-{N-[4-(3-carboxyl-propionamido)-benzoyl]-L-phenylalanyl}-L-phenylaninol

Spectra Data: $^1$H-NMR (DMSO, 400 MHz): δ 12.18 (1H, COOH), 10.21 (1H, s, ArNHCO), 8.38 (1H, d, J=8.4 Hz, NHCO), 7.88 (1H, d, J=8.4 Hz, NHCO), 7.77 (2H, d, J=8.8 Hz, H-3", 7"), 7.64 (2H, d, J=8.4 Hz, H-4", 6"), 7.31-7.11 (10H, m, H-5-9, 5'-9'), 4.82 (1H, t, OH), 4.67 (1H, m, H-2), 3.90 (1H, m, H-2'), 3.35-3.24 (2H, m, H-1'), 3.05-2.91 (2H, m, H-3), 2.86(1H, dd, J=5.6, 13.6 Hz, H-3'a), 2.66(1H, dd, J=8.0, 13.6, Hz, H-3'b), 2.61-2.50 (4H, m, ArNHCOCH$_2$CH$_2$COOH); $^{13}$C-NMR (DMSO, 100 MHz): δ 173.9 (COOH), 171.1 (ArNHCO), 170.6 (C-1), 165.6 (C-1"), 142.0 (C-5"), 139.0 (C-4'), 138.5 (C-4), 129.23 (×2), 129.21 (×2), 128.4 (C-3", 7"), 128.2 (C-2"), 128.1 (×2), 128.0 (×2), 126.2 (C-7), 125.9 (C-7'), 117.9 (C-4", 6"), 62.2 (C-1'), 54.8 (C-2), 52.5 (C-2'), 37.2 (C-3'), 36.5 (C-3), 31.1 (ArNHCOCH$_2$CH$_2$COOH), 28.7 (ArNHCOCH$_2$CH$_2$COOH).

Example 62 methyl N-{N-[4-(3-carboxyl-propionamido)-benzoyl]-L-phenylalanyl}-L-phenylalaninate Spectra Data: $^1$H-NMR (DMSO, 400 MHz): δ 12.21 (1H, br, COOH), 10.22 (1H, s, ArNHCO), 8.55 (1H, d, J=7.6 Hz, NHCO), 8.43 (1H, d, J=8.8 Hz, NHCO), 7.74 (2H, d, J=8.8 Hz, H-3", 7"), 7.63 (2H, d, J=8.4 Hz, H-4", 6"), 7.34-7.13 (10H, m, H-5-9, 5'-9'), 4.73 (1H, m, H-2), 4.51 (1H, m, H-2'), 3.59 (3H, s, OCH$_3$), 3.07-2.91 (4H, m, H-3, 3'), 2.59-2.50 (4H, m, ArNHCOCH$_2$CH$_2$COOH); $^{13}$C-NMR (DMSO, 100 MHz): δ 173.9 (COOH), 171.9, 171.8, 170.6, 165.7 (C-1"), 142.0 (C-5"), 138.4 (C-4), 137.4 (C-4'), 129.2 (C-6, 8), 129.2 (C-6', 8'), 128.4 (C-3", 7"), 128.3 (C-5', 9'), 128.12 (C-2"), 128.07 (C-5, 9), 126.6 (C-7'), 126.2 (C-7), 117.9 (C-4", 6"), 54.4 (C-2), 53.8 (C-2'), 51.9 (OCH$_3$), 36.9 (C-3'), 36.6 (C-3), 31.1 (ArNHCOCH$_2$CH$_2$COOH), 28.7 (ArNHCOCH$_2$CH$_2$COOH).

Example 63 methyl N-(N-benzoyl-O-acetyl-3-acetamido-L-tyrosyl)-L-phenylalaninate

Spectra Data; $^1$H-NMR (DMSO, 400 MHz): δ 9.34 (1H, s, ArNHCO), 8.58-8.53 (2H, m, NHCO×2), 7.85 (1H, s, H-5), 7.77 (2H, d, J=8.8 Hz, H-3", 7"), 7.51 (1H, t, H-5"), 7.43 (2H, t, H-4", 6"), 7.25-7.19 (5H, m, H-5'-9'), 7.09 (1H, d, J=8.0 Hz, H-8), 7.99 (1H, d, J=8.0 Hz, H-9), 4.70 (1H, m, H-2), 4.51 (1H, m, H-2'), 3.59 (3H, s, OCH$_3$), 3.08-2.89 (4H, m, H-3, 3'), 2.24 (3H, s, OCOCH$_3$), 2.05 (3H, s, NHCOCH$_3$); $^{13}$C-NMR (DMSO, 100 MHz): δ 171.8, 171.7, 169.0, 166.4 (C-1"), 140.1 (C-7), 137.0 (C-4'), 135.8 (C-6), 134.2 (C-2"), 131.3 (C-5"), 130.1 (C-4), 129.1 (C-6', 8'), 128.3 (C-5', 9'), 128.2 (C-4", 6"), 127.5 (C-3", 7"), 126.6 (C-7'), 125.3, 124.7, 122.4 (C-5), 54.5 (C-2), 53.8 (C-2'), 51.9 (OCH$_3$), 36.6, 36.5, 23.6 (NHCOCH$_3$), 21.1 (OCOCH$_3$).

Example 64 methyl N-(N-benzoyl-L-phenylalanyl)-4-propionamido-L-phenylalaninate

Spectra Data: mp 244.5-246.0° C.; $^1$H-NMR (DMSO, 400 MHz) δ 9.89 (1H, s, ArNHCO), 8.60-8.57 (2H, m, NHCO×2), 7.76 (2H, d, J=7.6 Hz, H-3", 7"), 7.51-7.47 (3H, m, H-5", 6', 8'), 7.41 (2H, t, H-4", 6"), 7.32 (2H, d, J=7.6 Hz, H-5, 9), 7.33 (2H, t, H-6, 8), 7.15-7.13 (3H, m, H-7, 5', 9'), 4.73 (1H, m, H-2), 4.46 (1H, m, H-2'), 3.57 (3H, s, OCH$_3$), 3.08-2.92 (4H, m, H-3, 3'), 2.28 (2H, q, J=7.6, Hz, NHCOCH$_2$CH$_3$), 1.05 (3H, t, J=7.6 Hz, NHCOCH$_2$CH$_3$); $^{13}$C-NMR (DMSO, 100 MHz): δ 171.96, 171.93, 171.8, 166.3 (C-1"), 138.4 (C-4), 138.1 (C-7'), 134.1 (C-2"), 131.4 (C-5", 4'), 129.4 (C-5', 9'), 129.2 (C-6, 8), 128.2 (C-4", 6"), 128.1 (C-5, 9), 127.5 (C-3", 7"), 126.3 (C-7), 118.9 (C-6', 8'), 54.7 (C-2), 54.0 (C-2'), 51.9 (OCH$_3$), 37.0, 36.1, 29.6 (NHCOCH$_2$CH$_3$), 9.8 (NHCOCH$_2$CH$_3$).

Example 65

N-[N-(4-dimethylaminomethyl-benzoyl)-L-phenylalanyl]-O-acetyl-L-phenylalaninol

Spectra Data: $^1$H-NMR (CDCl$_3$, 400 MHz): δ 7.68 (2H, d, J=8.4 Hz, H-3", 7"), 7.40 (2H, d, J=8.0 Hz, H-4", 6"), 7.30-7.06 (10H, m, H-5'-9', 5-9) 6.76 (1H, br, NHCO), 6.07 (1H, br, NHCO), 4.78 (1H, m, H-2), 4.35 (1H, m, H-2'), 3.92 (1H, dd, J=4.8, 11.6 Hz, H-1'a), 3.81 (1H, dd, J=4.0, 11.6 Hz, H-1'b), 3.49 (2H, s, ArCH$_2$N(CH$_3$)$_2$), 3.22 (1H, dd, J=5.6, 13.6 Hz, H-3a), 3.06 (1H, dd, J=8.4, 13.2 Hz, H-3b), 2.76-2.73 (2H, m, H-3'), 2.26 (6H, s, ArCH$_2$N(CH$_3$)$_2$), 2.03 (3H, s, COCH$_3$); $^{13}$C-NMR (CDCl$_3$, 100 MHz): δ 170.8 (C-1), 170.2 (OCOCH$_3$), 166.9 (C-1"), 143.0 (C-5"), 136.7, 136.6, 132.5 (C-2"), 129.3 (×4, C-6, 8, 6', 8'), 129.1 (C-4", 6"), 128.7 (C-5', 9'), 128.5 (C-5, 9), 127.1 (C-3", 7"), 126.7 (C-7, 7'), 64.5 (C-1'), 63.8 (ArCH$_2$N(CH$_3$)$_2$), 54.9 (C-2), 49.3 (C-2'), 45.3 (ArCH$_2$N(CH$_3$)$_2$), 38.4, 37.4, 20.8 (OCOCH$_3$).

Example 66

N-[N-(4-dimethylaminomethyl-benzoyl)-L-phenylalanyl]-O-propionyl-L-phenylalaninol Spectra Data: $^1$H-NMR (CDCl$_3$, 400 MHz): δ 7.70 (2H, d, J=8.0 Hz, H-3", 7"), 7.44 (2H, d, J=7.6 Hz, H-4", 6"), 7.30-7.06 (10H, m, H-5'-9', 5-9), 6.83 (1H, br, NHCO), 6.13 (1H, br, NHCO), 4.78 (1H, m, H-2), 4.34 (1H, m, H-2'), 3.93 (1H, dd, J=5.2, 11.6 Hz, H-1'a), 3.85-3.81 (1H, m, H-1'b), 3.59 (2H, s, ArCH$_2$N(CH$_3$)$_2$), 3.22 (1H, dd, J=7.0, 13.6 Hz, H-3a), 3.06 (1H, dd, J=8.4, 13.6 Hz, H-3b), 2.80-2.70 (2H, m, H-3'), 2.33 (6H, s, ArCH$_2$N(H$_3$)$_2$), 2.29 (2H, q, J=7.6, COCH$_2$CH$_3$), 1.13 (3H, t, J=7.6, COCH$_3$); $^{13}$C-NMR (CDCl$_3$, 100 MHz): δ 173.9 (OCOCH$_2$CH$_3$), 169.9 (C-1), 166.5 (C-1"), 143.0 (C-5"), 136.4, 136.2, 132.6 (C-2"), 129.2 (C-6, 8), 128.9 (C-6', 8'), 128.8 (C-4", 6"), 128.4 (C-5', 9'), 128.2 (C-5, 9), 126.9 (C-3", 7"), 126.7 (C-7), 126.4 (C-7'), 64.0 (C-1'), 63.4 (ArCH$_2$N(CH$_3$)$_2$), 54.6 (C-2), 49.1 (C-2'), 44.6 (ArCH$_2$N (CH$_3$)$_2$), 38.1, 37.1, 27.0 (OCOCH$_2$CH$_3$), 8.7 (OCOCH$_2$CH$_3$).

Example 67

N-{N-[4-(4-morpholinyl)methyl-benzoyl]-L-phenylalanyl}-O-propionyl-L-phenylalaninol Spectra Data: $^1$H-NMR (DMSO, 400 MHz): δ 8.68 (1H, d, J=8.0 Hz, NHCO), 8.30 (1H, d, J=7.6 Hz, NHCO), 7.78 (2H, d, J=8.4 Hz, H-3", 7"), 7.36 (2H, d, J=8.0 Hz, H-4", 6"), 7.31-7.13 (10H, m, H-5'-9', 5-9), 4.65 (1H, m, H-2), 4.18 (1H, m, H-2'), 4.03 (1H, dd, J=4.8, 11.2 Hz, H-1'a), 3.87 (1H, dd, J=6.8, 11.2 Hz, H-1'b), 3.57 (4H, t, J=4.4 Hz,—CH$_2$OCH$_2$—), 3.49 (2H, s, ArCH$_2$N<), 2.96 (2H, d, J=7.2 Hz, H-3), 2.79 (2H, d, J=6.8 Hz, H-3'), 2.34 (4H, s, ArCH$_2$N(CH$_2$)$_2$), 2.26 (2H, q, J=7.6 Hz, COCH$_2$CH$_3$), 0.98 (3H, t, J=7.6 Hz, COCH$_2$CH$_3$); $^{13}$C-NMR (DMSO, 100 MHz): δ 173.5 (COEt), 171.3 (C-1), 165.9 (C-1"), 142.3 (C-5"), 138.4 (C-4), 138.1 (C-4'), 132.8 (C-2"), 129.2 (×2), 129.1 (×2), 128.5 (C-4", 6"), 128.2 (C-5, 9), 128.0 (C-5', 9'), 127.4 (C-3", 7"), 126.2 (C-7, 7'), 66.2 (—CH$_2$OCH$_2$—), 64.5 (C-1') 62.0 (ArCH$_2$N<), 55.1 (C-2), 53.2 (ArCH$_2$N(CH$_2$)$_2$), 49.2 (C-2'), 37.2, 36.6, 26.7 (COCH$_2$CH$_3$), 8.9 (COCH$_2$CH$_3$).

Example 68 methyl N-[N-(4-methyl-benzoyl)-4-acetamido-L-phenylalanyl]-O-acetyl-L-tyrosinate Spectra Data: mp 222.0-223.0° C.; $^1$H-NMR (DMSO, 400 MHz): δ 9.84 (1H, s, ArNHCO), 8.55 (1H, d, J=7.2 Hz, NHCO), 8.42 (1H, d, J=8.4 Hz, NHCO), 7.69 (2H, d, J=8.0 Hz, H-3", 7"), 7.44 (2H, d, J=8.4 Hz, H-6, 8), 7.27-7.23 (6H, m, H-5, 9, 5', 9', 4", 6"), 6.98 (2H, d, J=8.4 Hz, H-6', 8'), 4.71 (1H, m, H-2), 4.52 (1H, m, H-2'), 3.59 (3H, OCH$_3$), 3.07-2.86 (2H, m, H-3, 3'), 2.34 (3H, s, Ar—CH$_3$), 2.24 (3H, s, OCOCH$_3$), 1.99 (3H, s, NHCOCH$_3$); $^{13}$C-NMR (DMSO, 100 MHz): δ 171.4 (×2, C-1, 1'), 169.2 (ArOCO), 168.1 (ArNHCO), 166.0 (C-1"), 149.2 (C-7'), 141.2 (C-5"), 137.6 (C-7), 134.5 (C-4'), 132.8 (C-4), 131.2 (C-2"), 130.1 (C-5', 9'), 129.4 (C-5, 9), 128.7 (C-4", 6"), 127.4 (C-3", 7"), 121.6 (C-6', 8'), 118.7 (C-6, 8), 54.5 (C-2), 53.7 (C-2'), 51.9 (OCH$_3$), 36.5, 35.9, 24.0 (OCOCH$_3$), 21.0 (ArCH$_3$), 20.9 (NHCOCH$_3$).

Example 69

N-(N-benzoyl-L-phenylalanyl)-4-acetyl-L-phenylalaninol

Spectra Data: mp 235.5-238.0° C.; $^1$H-NMR (DMSO, 400 MHz): δ 9.85 (1H, s, ArNHCO), 8.54 (1H, d, J=8.0 Hz, NHCO), 7.95 (1H, d, J=8.4 Hz, NHCO), 7.77 (2H, d, J=7.6 Hz, H-3", 7"), 7.50 (1H, t, H-5"), 7.44-7.40 (4H, m, H-4"-6", 6', 8'), 7.31 (2H, d, J=7.6 Hz, H-5, 9), 7.23 (1H, t, H-6, 8), 7.15-7.12 (3H, m, H-7, 5', 9'), 4.84 (1H, t, OH), 4.67 (1H, m, H-2), 3.86 (1H, m, H-2'), 3.34-3.27 (2H, m, H-1'), 3.05-2.92 (2H, m, H-3), 2.79 (1H, dd, J=6.0, 13.2 Hz, H-3'a), 2.61 (1H, dd, J=7.6, 13.2 Hz, H-3'b), 2.00 (3H, s, COCH$_3$); $^{13}$C-NMR (DMSO, 100 MHz): δ 171.0 (C-1), 168.1 (ArNHCO), 166.2 (C-1"), 138.5 (C-4), 137.4 (C-7'), 134.1 (C-2"), 133.5 (C-4'), 131.3 (C-5"), 129.4 (C-5', 9'), 129.2 (C-6, 8), 128.2 (C-4", 6"), 128.1 (C-5, 9), 127.4 (C-3", 7"), 126.2 (C-7'), 118.8 (C-6', 8'), 62.1 (C-1'), 55.0 (C-2), 52.6 (C-2'), 37.4 (C-3), 35.8 (C-3'), 24.0 (COCH$_3$).

Example 70 methyl N-[N-(4-chloro-benzoyl)-4-propionamido-L-phenylalanyl]-L-phenylalaninate

Spectra Data: $^1$H-NMR (DMSO, 400 MHz): δ 9.75 (1H, s, ArNHCO), 8.52 (2H, m, NHCO×2), 7.78 (2H, m, H-3", 7"), 7.53-7.42 (4H, m, H-4", 6", 6, 8), 7.24-7.19 (7H, m, H-5, 9, 5'-9'), 4.70 (1H, m, H-2), 4.51 (1H, m, H-2'), 3.59 (3H, S, OCH$_3$), 3.09-2.87 (4H, m, H-3, 3'), 2.26 (2H, q, J=7.6 Hz, COCH$_2$CH$_3$), 1.05 (3H, t, J=7.6 Hz, COCH$_2$CH$_3$); $^{13}$C-NMR (DMSO, 100 MHz): δ 171.83, 171.77, 166.1 (ArNHCO), 165.1 (C-1"), 137.6 (C-7), 137.0 (C-4'), 136.1 (C-5"), 134.0 (C-4), 132.7 (C-2"), 129.4 (C-3", 7"), 129.1 (C-6', 8'), 128.3 (C-4", 6"), 128.2 (C-5, 9), 127.4 (C-5', 9'), 126.6 (C-7'), 118.7 (C-6, 8), 54.6, 53.7, 51.9 (OCH$_3$), 36.6, 36.4, 29.5 (COCH$_2$CH$_3$), 9.73 (COCH$_2$CH$_3$).

Example 71 methyl N-(N-benzoyl-L-phenylalanyl)-O-methyl-L-tyrosinate

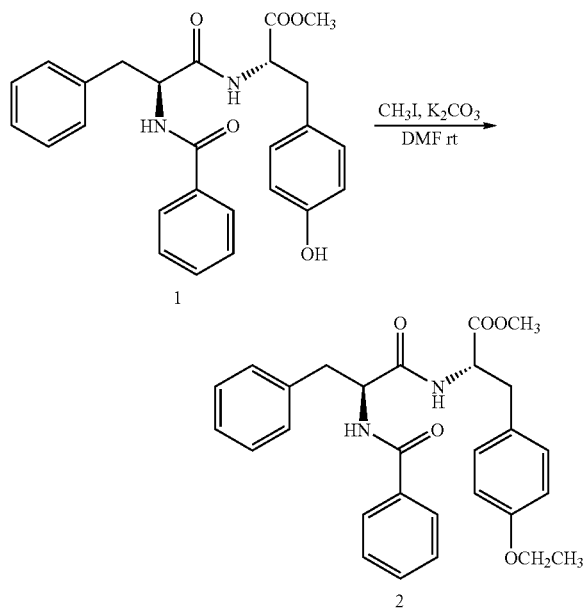

Reagents and Reaction Conditions:
CH$_3$I, K$_2$CO$_3$, DMF, rt., and reaction overnight
Preparation Procedures:
The compound I previously prepared (Example 3) (446 mg, 1.0 mmol) was dissolved in anhydrous DMF (5 ml). To the solution was added anhydrous K$_2$CO$_3$ (276 mg, 2.0 mmol). To the reaction flask was added ethyl iodide (CH$_3$CH$_2$I, 160 μl, 2.0 mmol) under argon. The reaction mixture was stirred overnight at room temperature, and was dispersed in an aqueous system of EtOAc (70 ml) and 10% Na$_2$CO$_3$ (30 ml) on the morrow. The solution was extracted. The organic layer was washed with saturated aqueous sodium chloride (2×20 ml) and dried over anhydrous Na$_2$SO$_4$. The solution was filtered. The filtrate was evaporated under reduced pressure to recover the solvents, giving a product (468 mg, 98.7%) as a white powder. The structure of the product was consistent with that of the designed compound 2 as confirmed by spectra characterization.

Spectra Data: mp 170.0-172.0° C.; $^1$H-NMR (CDCl$_3$, 400 MHz): δ 7.69 (2H, d, J=7.6 Hz, H-3", 7"), 7.51 (1H, t, H-5"), 7.42 (2H, t, H-4", 6"), 7.31-7.20 (5H, m, H-5-9), 6.86 (2H, d, J=8.4 Hz, H-5', 9'), 6.76 (1H, br, NHCO), 6.66 (2H, d, J=8.4 Hz, H-6', 8'), 6.29 (1H, br, NHCO), 4.84 (1H, m, H-2), 4.72 (1H, m, H-2'), 3.90 (2H, m, ArOCH$_2$CH$_3$), 3.70 (3H, s, OMe), 3.21 (1H, dd, J=6.0, 14.0 Hz, H-3'a), 3.12 (1H, dd, J=7.6, 14.0 Hz, H-3'b), 3.02 (1H, dd, J=5.6, 13.6 Hz, H-3a), 2.90 (1H, dd, J=6.4, 13.6 Hz, H-3b), 1.36 (3H, t, ArOCH$_2$CH$_3$); $^{13}$C-NMR (CDCl$_3$, 100 MHz): δ 171.7 (C-1), 170.6 (C-1'), 167.3 (C-1"), 158.3 (C-7'), 136.7 (C-4), 133.9 (C-2"), 132.2 (C-5"), 130.4 (C-5', 9'), 129.8 (C-6, 8), 129.0 (×2), 128.9 (×2), 127.5 (C-4'), 127.4 (C-7), 127.3 (C-3", 7"), 114.8 (C-6', 8'), 63.5 (ArOCH$_2$CH$_3$), 54.8 (C-2), 53.8 (C-2'), 52.7 (C-OMe), 38.4 (C-3), 37.3 (C-3'), 15.1 (ArOCH$_2$CH$_3$).

Following the similar synthetic process as that in example 71, derivatives of examples 72-84 were prepared, respectively, through selecting appropriate alkyl iodide and an intermediate 2-chloro-N,N-dimethyl ethylamine hydrochloride as starting materials to carry out an electrophilic substitution of a hydroxyl and amino group in the phenyl ring of the compounds in the examples mentioned above; or selecting dimethylamine, diethylamine, pyrrolidine, morpholine and the like as a nucleophilic reagent to carry out a substitution of a chlorine atom in a compound containing a chloro group (RNHCOCH$_2$Cl).

Example 72 methyl N-(N-benzoyl-L-phenylalanyl)-O-n-butyl-L-tyrosinate

Spectra Data: mp 177.0-178.0° C.; $^1$H-NMR (CDCl$_3$, 400 MHz): δ 7.69 (2H, d, J=7.6 Hz, H-3", 7"), 7.51 (1H, t, H-5"), 7.42 (2H, t, H-4", 6"), 7.31-7.23 (5H, m. H-5-9), 6.85 (2H, d, J=8.4 Hz, H-5', 9'), 6.76 (1H, br, NHCO), 6.66 (2H, d, J=8.4 Hz, H-6', 8'), 6.31 (1H, br, NHCO), 4.83 (1H, m, H-2), 4.72 (1H, m, H-2'), 3.82 (2H, m, ArOCH$_2$CH$_2$CH$_2$CH$_3$), 3.70 (3H, s, OMe), 3.21 (1H, dd, J=5.6, 14.0 Hz, H-3'a), 3.12 (1H, dd, J=7.2, 13.6 Hz, H-3'b), 3.01 (1H, dd, J=5.6, 14.0 Hz, H-3a), 2.90 (1H, dd, J=6.8, 14.0 Hz, H-3b), 1.70 (2H, m, ArOCH$_2$CH$_2$CH$_2$CH$_3$), 1.45 (2H, m, ArOCH$_2$CH$_2$CH$_2$CH$_3$), 0.96 (2H, t, J=7.6 Hz, ArOCH$_2$CH$_2$CH$_2$CH$_3$); $^{13}$C-NMR (CDCl$_3$, 100 MHz): δ 171.4 (C-1), 170.3 (C-1'), 167.0 (C-1"), 158.2 (C-7'), 136.4 (C-4), 133.6 (C-2"), 131.8 (C-5"), 130.1 (C-5', 9'), 129.4 (C-6, 8), 128.7 (C-5, 9), 128.6 (C-4", 6"), 127.04 (C-4', C-7), 127.01 (C-3", 7"), 114.5 (C-6', 8'), 63.5 (ArOCH$_2$CH$_2$CH$_2$CH$_3$), 54.5 (C-2), 53.5 (C-2'), 52.3 (OMe), 38.1 (C-3), 36.9 (C-3'), 31.3 (ArOCH$_2$CH$_2$CH$_2$CH$_3$), 19.2 (ArOCH$_2$CH$_2$CH$_2$CH$_3$), 13.8 (ArOCH$_2$CH$_2$CH$_2$CH$_3$).

Example 73

N-(N-benzoyl-L-phenylalanyl)-O-ethyl-L-tyrosine

Spectra Data: $^1$H-NMR (MSO, 400 MHz): δ 12.85 (1H, br, COOH), 8.55 (1H, d, J=8.4 Hz, NHCO), 8.24 (1H, d, J=8.0 Hz, NHCO), 7.76 (2H, d, J=7.6 Hz, H-3", 7"), 7.52 (1H, t, H-5"), 7.43 (2H, t, H-4", 6"), 7.33 (2H, d, J=7.6 Hz, H-5, 9), 7.23 (2H, t, J=7.6 Hz, H-6, 8), 7.15-7.10 (3H, m, J=8.4 Hz, H-7, 5', 9'), 6.70 (2H, d, J=8.4 Hz, H-6', 8'), 4.73 (1H, m, H-2), 4.41 (1H, m, H-2'), 3.87 (2H, m, ArOCH$_2$CH$_3$), 3.10-2.84 (4H, m, H-3', 3), 1.26 (3H, t, ArOCH$_2$CH$_3$); $^{13}$C-NMR (DMSO, 100 MHz): δ 172.9 (C-1'), 171.4 (C-1), 166.2 (C-1"), 157.2 (C-7'), 138.4 (C-4), 134.0 (C-2"), 131.4 (C-5"), 130.2 (C-5', 9'), 129.2 (C-6, 8), 129.0 (C-4'), 128.2 (C-4", 6"), 128.1 (C-5, 9), 127.4 (C-3", 7"), 126.2 (C-7), 114.1 (C-6, 8'), 62.8 (ArOCH$_2$CH$_3$), 54.5 (C-2'), 53.8 (C-2), 36.8 (C-3), 35.9 (C-3'), 14.7 (ArOCH$_2$CH$_3$).

Example 74

N-(N-benzoyl-L-phenylalanyl)-O-n-butyl-L-tyrosine sodium salt

Spectra Data: $^1$H-NMR (DMSO, 400 MHz): δ 8.82 (1H, d, J=8.4 Hz, NHCO), 7.78 (2H, d, J=7.2 Hz, H-3", 7"), 7.51-7.47 (2H, m, H-5", NHCO), 7.41 (2H, t, H-4", 6"), 7.30 (2H, d, J=7.6 Hz, H-5, 9), 7.22 (2H, t, H-6, 8), 7.12 (1H, t, H-7), 6.99 (2H, J=8.4 Hz, H-5', 9'), 6.55 (2H, d, J=8.0 Hz, H-6', 8'), 4.57 (1H, m, H-2), 3.94 (1H, m, H-2'), 3.75 (2H, t, J=6.4 Hz, ArOCH$_2$CH$_2$CH$_2$CH$_3$), 3.12-2.85 (4H, m, H-3, 3'), 1.61 (2H, m, ArOCH$_2$CH$_2$CH$_2$CH$_3$), 1.37 (2H, m, ArOCH$_2$CH$_2$CH$_2$CH$_3$), 0.89 (2H, t, J=7.6 Hz, ArOCH$_2$CH$_2$CH$_2$C$_3$); $^{13}$C-NMR (DMSO, 100 MHz): δ 172.5 (C-1'), 169.6 (C-1), 166.0 (C-1"), 156.6 (C-7'), 138.7 (C-4), 134.1 (C-2"), 131.0 (C-5"), 130.9 (C-4'), 130.5 (C-5', 9'), 128.9 (C-6, 8), 127.93, 127.87, 127.3 (C-3", 7"), 125.9 (C-7), 113.4 (C-6', 8'), 66.8 (ArOCH$_2$CH$_2$CH$_2$CH$_3$), 55.4, 55.3, 36.6, 36.3, 30.7 (ArOCH$_2$CH$_2$CH$_2$CH$_3$), 18.6 (ArOCH$_2$CH$_2$CH$_2$CH$_3$), 13.5 (ArOCH$_2$CH$_2$CH$_2$CH$_3$).

Example 75

N-[N-berizoyl-O-(2-dimethylamino-ethyl)-L-tyrosyl]-L-phenylalaninol hydrochloride Spectra Data: mp 158.5-161.0° C.; $^1$H-NMR (DMSO, 400 MHz): δ 10.57 (1H, br, CH$_2$CH$_2$N$^+$H (CH$_3$)$_2$.Cl$^-$), 8.57 (1H, d, J=8.4 Hz, NHCO), 8.03 (1H, br, NHCO), 7.83 (2H, d, J=7.6 Hz, H-3", 7"), 7.52 (1H, t, H-5"), 7.45 (2H, t, H-4", 6"), 7.28-7.11 (7H, m, H-5'-9', 5, 9) 6.88 (2H, d, J=8.8 Hz, H-6, 8), 4.88 (1H, br, OH), 4.63 (1H, m, H-2), 4.28 (2H, t, J=4.8 Hz, ArOCH$_2$CH$_2$N(CH$_3$)$_2$.HCl), 3.89 (1H, m, H-2'), 3.44 (2H, t, J=4.8 Hz, ArOCH$_2$CH$_2$N(CH$_3$)$_2$.HCl), 3.34-3.27 (2H, m, H-1'), 3.00-2.85 (3H, m, H-3, 3'a), 2.79 (6H, s, N(CH$_3$)$_2$), 2.71-2.66 (1H, dd, J=8.0, 13.6 Hz, 3'b); $^{13}$C-NMR (DMSO, 100 MHz): δ 171.0 (C-1), 166.0 (C-1"), 156.0 (C-7), 139.1 (C-4'), 134.0 (C-2"), 131.3 (C-5", 4), 130.3 (C-5, 9), 129.2 (C-6', 8'), 128.2 (C-4", 6"), 128.1 (C-5', 9'), 127.5 (C-3", 7"), 125.9 (C-7') 114.2 (C-6, 8), 62.2, 62.1, 55.2 (×2), 52.6 (C-2'), 42.7(×2), 36.4 (×2).

Example 76

N-[N-4-(dimethylaino-acetamido)-benzoyl-L-phenylalanyl]-L-phenylalaninol

Spectra Data: mp 162.5-164.0° C.; $^1$H-NMR (DMSO, 400 MHz): δ 9.94 (1H, s, ArNHCO), 8.39 (1H, d, J=8.8 Hz, NHCO), 7.89 (1H, d, J=8.4 Hz, NHCO), 7.77 (2H, d, J=8.8 Hz, H-3", 7"), 7.73 (2H, d, J=8.8 Hz, H-4", 6"), 7.31-7.11 (10H, m, H-5-9, 5'-9'), 4.82 (1H, t, OH), 4.67 (1H, m, H-2), 3.89 (1H, m, H-2'), 3.35-3.24 (2H, m, H-1'), 3.09 (2H, COCH$_2$N<), 3.07-2.91 (1H, m, H-3), 2.86 (1H, dd, J=5.6, 13.6 Hz, H-3'a), 2.66 (1H, dd, J=7.6, 13.6 Hz, H-3'b), 2.28 (6H, s,—N(CH$_3$)$_2$); $^{13}$C-NMR (DMSO, 100 MHz): δ 171.0 (C-1), 169.1 (ArNHCO), 165.5 (C-1"), 141.4 (C-5"), 139.0 (C-4'), 138.5 (C-4), 129.2 (×4, C-6, 8, 6', 8'), 128.6 (C-2"), 128.2 (C-3", 7"), 128.1 (×2), 128.0 (×2), 126.2 (C-7), 125.9 (C-7'), 118.5 (C-4", 6"), 63.3 (COCH$_2$N<), 62.2 (C-1'), 54.8 (C-2), 52.5 (C-2'), 45.4 (×2, —N(CH$_3$)$_2$), 37.3 (C-3), 36.4 (C-3').

Example 77

N-[N-4-(2-dimethylamino-ethoxyl)-benzoyl-L-phenylalanyl]-L-phenylalaninol

Spectra Data: $^1$H-NMR (CDCl$_3$, 400 MHz): δ 7.67 (2H, d, J=8.8 Hz, H-3", 7"), 7.31-7.07 (10H, m, H-5-9, 5'-9'), 6.92 (2H, d, J=8.8 Hz, H-4", 6"), 6.78 (1H, d, J=7.6 Hz, NHCO), 6.28 (1H, d, J=8.0 Hz, NHCO), 4.80 (1H, m, H-2), 4.11-4.07 (3H, m, ArOC$_2$, H-2'), 3.42 (2H, m, H-1'), 3.23 (1H, dd, J=6.4, 13.6 Hz, H-3a), 3.06 (1H, dd, J=8.4, 13.6 Hz, H-3b), 2.80-2.66 (4H, m, H-3', CH$_2$N(CH$_3$)$_2$), 2.34 (6H, s, —N(CH$_3$)$_2$); $^{13}$C-NMR (CDCl$_3$, 100 MHz): δ 171.0 (C-1), 166.8 (C-1"), 161.8 (C-5"), 137.4 (C-4), 136.8 (C-4'), 129.3 (C-3", 7"), 129.1 (C-6, 8), 128.9 (C-6', 8'), 128.8 (C-5', 9'), 128.5 (C-5, 9), 127.1 (C-7), 126.5 (C-7'), 125.8 (C-2"), 114.4 (C-4", 6"), 66.2 (ArOCH$_2$), 63.4 (C-1'), 58.1 (CH$_2$N(CH$_3$)$_2$), 55.1 (C-2), 52.9 (C-2'), 45.9 (—N(CH$_3$)$_2$), 38.6 (C-3'), 36.8 (C-3).

Example 78 methyl N-[N-4-(2-dimethylamino-ethoxyl)-benzoyl-L-phenylalanyl]-L-phenylalaninate Spectra Data: $^1$H-NMR (CDCl$_3$, 400 MHz): δ 7.64 (2H, d, J=8.8 Hz, H-3", 7"), 7.30-6.95 (10H, m, H-5-9, 5'-9'), 6.92 (2H, d, J=8.8 Hz, H-4", 6"), 6.58 (1H, d, J=7.6 Hz, NHCO), 6.35 (1H, d, J=7.2 Hz, NHCO), 4.83-4.76 (2H, m, H-2, 2'), 4.10 (2H, t, J=6.0 Hz, ArOCH$_2$), 3.70 (3H, s, OCH$_3$), 3.21-2.93 (4H, m, H-3, 3'), 2.75 (2H, t, J=6.0 Hz, CH$_2$N(CH$_3$)$_2$), 2.35 (6H, s, —N(CH$_3$)$_2$); $^{13}$C-NMR (CDCl$_3$, 100 MHz): δ 171.3 (C-1), 170.5 (C-1'), 166.6 (C-1"), 161.7 (C-5"), 136.4 (C-4), 135.5 (C-4'), 129.4 (C-3", 7"), 129.1 (C-6, 8), 128.8 (C-6', 8'), 128.7 (C-5', 9'), 128.5 (C-5, 9), 127.0 (C-7, 7'), 125.9 (C-2"), 114.3 (C-4", 6"), 66.1 (ArOCH$_2$), 58.1 (CH$_2$N(CH$_3$)2), 54.4 (C-2), 53.4 (C-2'), 52.3 (OCH$_3$), 45.9 (—N(CH$_3$)$_2$), 38.0, 37.8.

Example 79

N-(N-benzoyl-L-phenylalanyl)-O-methyl-L-tyrosine sodium salt

Spectra Data; $^1$H-NMR (DMSO, 400 MHz): δ 8.81 (1H, d, J=8.4 Hz, NHCO), 7.78 (2H, d, J=7.2 Hz, H-3", 7"), 7.48 (2H, m, H-5", NHCO), 7.42 (2H, t, H-4", 6"), 7.30 (2H, d, J=8.4 Hz, H-5, 9), 7.22 (2H, t, H-6, 8), 7.13 (1H, t, H-7), 7.01 (2H, d, J=8.4 Hz, H-5', 9'), 6.57 (2H, d, J=8.4 Hz, H-6', 8'), 4.57 (1H, m, H-2), 3.95 (1H, m, H-2'), 3.59 (3H, s, ArOCH$_3$), 3.13-2.86 (4H, m, H-3, 3'); $^{13}$C-NMR (DMSO, 100 MHz): δ 172.7 (C-1'), 169.9 (C-1), 166.2 (C-1"), 157.3 (C-7'), 138.9 (C-4), 134.1 (C-2"), 131.3 (C-5), 131.0 (C-4'), 130.7 (C-5', 9'), 129.1 (C-6, 8), 128.2 (C-4", 6"), 128.1 (C-5, 9), 127.4 (C-3", 7"), 126.1 (C-7), 112.9 (C-6+, 8'), 55.6 (×2), 54.7 (ArOCH$_3$), 36.7, 36.3.

Example 80

N-[N-benzoyl-O-hydroxymethyl-L-tyrosyl]-L-phenylalaninol sodium salt

Spectra Data: $^1$H-NMR (DMSO, 400 MHz): δ 8.65 (1H, br, NHCO), 8.30 (1H, br, NHCO), 7.82 (2H, d, J=8.0 Hz, H-3", 7"), 7.50 (1H, t, H-5"), 7.43 (2H, t, H-4", 6"), 7.23-7.17 (5H, m, H-5'-9'), 7.12 (2H, d, J=8.0 Hz, H-5, 9), 6.69 (2H, d, J=8.4 Hz, H-6, 8), 5.17 (1H, br, OH), 4.59 (1H, m, H-2), 4.08 (2H, s, ArOCH$_2$COONa), 3.87 (1H, m, H-2'), 3.33-3.27 (2H, m, H-1'), 2.93-2.66 (4H, m, H-3, 3'); $^{13}$C-NMR (DMSO, 100 MHz): δ 171.2 (C-1, COONa), 166.0 (C-1"), 157.4 (C-7), 139.2 (C-4'), 134.2 (C-2"), 131.2 (C-5"), 129.7 (C-5, 9), 129.4 (C-4), 129.2 (C-6', 8'), 128.1 (C-4", 6"), 128.0 (C-5', 9'), 127.4 (C-3", 7"), 125.8 (C-7'), 114.0 (C-6, 8), 67.8 (ArOCH$_2$COONa), 62.1 (C-1'), 55.5 (C-2), 52.6 (C-2'), 36.4 (C-3, 3').

Example 81 methyl N-[N-4-(dimethylamino-acetamido)-benzoyl-L-phenylalanyl]-L-phenylalaninate Spectra Data: mp 192.5-194.0° C.; $^1$H-NMR (DMSO, 400 MHz): δ 9.92 (1H, s, ArNHCO), 8.52 (1H, d, J=7.6 Hz, NHCO), 8.41 (1H, d, J=8.4 Hz, NHCO), 7.71 (4H, m, H-3", 7", 4", 6"), 7.33-7.14 (10H, m, H-5-9, 5'-9'), 4.72 (1H, m, H-2), 4.50 (1H, m, H-2'), 3.57 (3H, s, OCH$_3$), 3.07 (2H, S, NHCOCH$_2$N<), 3.06-2.89 (4H, m, H-3, 3'), 2.26 (6H, s, —N(CH$_3$)$_2$); $^{13}$C-NMR (DMSO, 100 MHz): δ 172.5, 172.4, 169.8 (ArNHCO), 165.3 (C-1"), 142.1 (C-5"), 139.0 (C-4), 137.7 (C-4'), 129.83 (C-6, 8), 129.78 (C-6', 8'), 129.1 (C-2"), 128.9 (C-5', 9'), 128.8 (C-3", 7"), 128.7 (C-5, 9), 127.2 (C-7'), 126.9 (C-7), 119.1 (C-4", 6"), 63.9 (COCH$_2$N<), 55.1 (C-2), 54.4 (C-2'), 52.5 (OCH$_3$), 46.0 (—N(CH$_3$)$_2$), 37.6 (C-3), 37.2 (C-3').

Example 82 methyl N-{N-[4-(1-pyrrolidyl)acetamido-benzoyl]-L-phenylalanyl}-L-phenylalaninate Spectra Data: $^1$H-NMR (DMSO, 400 MHz): δ 9.93 (1H, s, ArNHCO), 8.53 (1H, d, J=7.2 Hz, NHCO), 8.43 (1H, d, J=8.8 Hz, NHCO), 7.75 (2H, d, J=8.8 Hz, H-3", 7"), 7.69 (2H, d, J=8.8 Hz, H-4", 6"), 7.34-7.15 (10H, m, H-5-9, 5'-9'), 4.74 (1H, m, H-2), 4.52 (1H, m, H-2'), 3.59 (3H, s, OCH$_3$), 3.26 (2H, COCH$_2$N<), 3.07-2.94 (4H, m, H-3, 3'), 2.59 (4H, m, COCH$_2$N(CH$_2$)$_2$), 1.74 (4H, m, >NCH$_2$CH$_2$CH$_2$CH$_2$N<); $^{13}$C-NMR (DMSO, 100 MHz): δ 171.8, 171.7, 169.2 (ArNHCO), 165.6 (C-1"), 141.4 (C-5"), 138.3 (C-4), 137.0 (C-4'), 129.2 (×2), 129.1 (×2), 128.5 (C-2"), 128.3 (×2), 128.2 (×2), 128.0 (×2), 126.6 (C-7'), 126.2 (C-7), 118.5 (C-4", 6"), 59.5 (COCH$_2$N<), 54.4 (C-2), 53.73 (C-2'), 53.69 (COCH$_2$N(CH$_2$)$_2$), 51.9 (OCH$_3$), 36.9 (C-3), 36.6 (C-3'), 23.5 (>NCH$_2$CH$_2$CH$_2$CH$_2$N<).

Example 83

N-[N-benzoyl-4-(3-carboxyl-propionamido)-L-phenylalanyl]-L-phenylalaninol

Spectra Data: $^1$H-NMR (DMSO, 400 MHz): δ 11.31 (1H s, ArNHCO), 8.96 (1H, d, J=8.4 Hz, NHCO), 8.37 (1H, d, J=8.0 Hz, NHCO), 7.79 (2H, m, H-3", 7"), 7.46 (2H, m, H-4", 6"), 7.40 (2H, d, J=8.4 Hz, H-6, 8), 7.24-7.11 (7H, m, H-5'-9', 5, 9), 5.05 (1H, br, OH), 4.58 (1H, m, H-2), 3.87 (1H, m, H-2'), 3.36-2.95 (2H, m, H-1'), 2.94-2.65 (4H, m, H-3, 3'), 2.33 (2H, m, CH$_2$COONa), 2.21 (2H, t, ArNHCOCH$_2$); $^{13}$C-NMR (DMSO, 100 MHz): δ 176.1 (CH$_2$COONa), 172.0 (ArNH-COCH$_2$), 171.1 (C-1), 165.0 (C-1"), 139.2 (C-4'), 138.0 (C-7), 135.9 (C-5"), 132.9 (C-4), 132.3 (C-2"), 129.34 (C-3", 7"), 129.30 (C-5, 9), 129.2 (C-6', 8'), 128.2 (C-4", 6"), 128.0 (C-5', 9'), 125.8 (C-7'), 118.3 (C-6, 8), 62.2 (C-1'), 55.6 (C-2), 52.6 (C-2'), 36.8, 36.4, 34.6 (CH$_2$COONa), 33.9 (ArNH-COCH$_2$).

Example 84

N-(N-benzoyl-4-dimethylamino-L-phenylalanyl)-L-phenylalaninol

Spectra Data: $^1$H-NMR (DMSO, 400 MHz): δ 7.74 (2H, d, J=7.2 Hz, H-3", 7"), 7.52 (1H, t, H-5"), 7.43 (2H, t, H-4", 6"), 7.21-7.08 (7H, m, H-5'-9', 5, 9), 6.90 (1H, d, J=7.2 Hz, NHCO), 6.62 (2H, d, J=8.4 Hz, H-6, 8), 5.96 (1H, d, J=7.6 Hz, NHCO), 4.70 (1H, m, H-2), 4.09 (1H, m, H-2'), 3.49-3.35 (2H, m, H-1'), 3.32 (4H, q, J=7.2 Hz, N(CH$_2$CH$_3$)$_2$), 3.19 (1H, dd, J=5.6, 13.2 Hz, H-3a), 2.88 (1H, dd, J=9.2, 13.6 Hz, H-3b), 2.77 (1H, dd, J=7.6, 13.6 Hz, H-3'a), 2.68 (1H, dd, J=7.2, 13.6 Hz, H-3'b), 2.18 (1H, t, OH), 1.14 (6H, t, J=7.2 Hz, N(CH$_2$CH$_2$)$_2$); $^{13}$C-NMR (DMSO, 100 MHz): δ 171.1 (C-1), 167.1 (C-1"), 146.9 (C-7), 137.4 (C-4'), 133.7 (C-2"), 131.8 (C-5"), 130.2 (C-5, 9), 129.1 (C-6', 8'), 128.6 (×2), 128.5 (×2), 127.1 (C-3", 7"), 126.5 (C-7'), 122.7 (C-4), 111.9 (C-6, 8), 63.4 (C-1'), 55.5 (C-2), 52.8 (C-2'), 44.3 (N(CH$_2$CH$_3$)$_2$), 37.9 (C-3'), 36.8 (C-3), 12.5 (N(CH$_2$CH$_3$)$_2$).

Example 85

N-(N-benzoyl-L-phenylalanyl)-L-tyrosine and sodium salt thereof

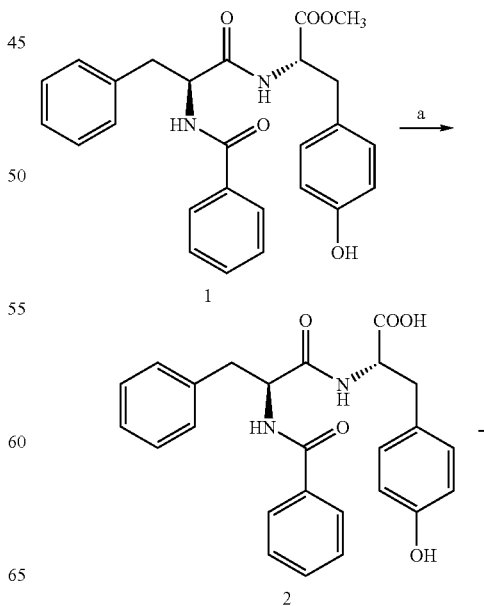

-continued

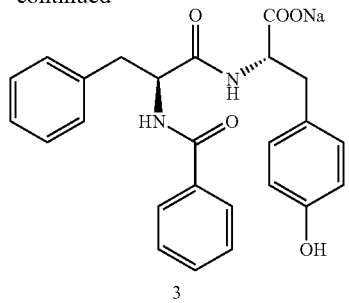

3

Reagents and Reaction Conditions:
(a) NaOH, DMF, rt., 5 hours; and
(b) NaOH/EtOH-CHCl₃
Preparation Procedures:
(a) The compound 1 previously prepared (Example 3) (2.0 mmol) was dissolved in a mixed solvent of DMF (5 ml) and EtOH (10 ml). To the solution was added 5 M NaOH (1 ml) with stirring. The reaction was kept overnight at room temperature. The pH of the resulting solution was adjusted with concentrated hydrochloric acid to 2-3. The reaction mixture was dispersed in an aqueous system of EtOAc (150 ml) and 10% Na₂CO₃ (30 ml). The solution was extracted. The organic layer was washed with saturated aqueous sodium chloride (2×20 ml) and dried over anhydrous Na₂SO₄. The solution was filtered and the filtrate was evaporated under reduced pressure to recover the solvents, giving the product N-(N-benzoyl-L-phenylalanyl)-L-tyrosine (compound 2) (674 mg, 78.0%) as a white powder.

Spectra Data: ¹H-NMR (DMSO, 400 MHz): δ 12.75 (COOH), 9.22 (1H, s, Ar—OH), 8.55 (1H, d, J=8.4 Hz, NHCO), 8.23 (1H, d, J=7.6 Hz, NHCO), 7.76 (2H, d, J=7.6 Hz, H-3", 7"), 7.51 (1H, t, H-5"), 7.43 (2H, t, H-4", 6"), 7.34 (2H, d, J=7.2 Hz, H-5, 9), 7.24 (2H, t, H-6, 8), 7.15 (1H, t, H-7), 7.02 (2H, d, J=8.4 Hz, H-5', 9'), 6.61 (2H, d, J=8.4 Hz, H-6', 8'), 4.74 (1H, m, H-2'), 4.38 (1H, m, H-2), 3.11-2.82 (4H, m, H-3, 3'); ¹³C-NMR (DMSO, 100 MHz): δ 172.9 (C-1'), 171.5 (C-1), 166.3 (C-1"), 156.0 (C-7'), 138.4 (C-4), 134.0 (C-2"), 131.3 (C-5"), 130.1 (C-5', 9'), 129.2 (C-6, 8), 128.2 (C-4", 6"), 128.0 (C-5, 9), 127.4 (C-3", 7"), 127.3 (C-4'), 126.2 (C-7), 115.0 (C-6', 8'), 54.6 (C-2'), 53.9 (C-2), 36.9 (C-3), 35.9 (C-3').

(b) The compound 2 prepared in the previous step (235 mg, 0.48 mmol) was fully dissolved in a mixed solvent of EtOH (10 ml) and CHCl₃ (5 ml). To the solution was dropwise added 1.0 M NaOH (0.48 ml). The reaction was kept overnight at room temperature. The solution was evaporated to dryness to recover the solvents. The resulting solid was recrystallized from ethyl acetate, giving N-(N-benzoyl-L-phenylalanyl)-L-tyrosine sodium salt (133 mg, 61.2%) as a white powder.

Following the similar synthetic process as that in example 85, derivatives of examples 86-106 were prepared, respectively, through hydrolyzing a carboxyl methyl ester or an acylated products of an alcoholic hydroxyl in some of the compounds of the examples mentioned above, or preparing sodium salts thereof.

Example 86

N-(N-benzoyl-L-phenylalanyl)-L-phenylalanine

Spectra Data: ¹H-NMR (DMSO, 400 MHz): δ 12.81 (1H, br, COOH), 8.53 (1H, d, J=8.4 Hz, NHCO), 8.31 (1H, d, J=8.0 Hz, NHCO), 7.74 (2H, d, J=7.6 Hz, H-3", 7"), 7.46 (1H, t, H-5"), 7.40 (2H, t, H-4", 6"), 7.33-7.12 (10H, m, H-5-9, 5'-9'), 4.72 (1H, m, H-2), 4.46 (1H, m, H-2'), 3.10-2.90 (4H, m, H-3, 3'); ¹³C-NMR (DMSO, 100 MHz): δ 172.8 (C-1'), 171.5 (C-1), 166.2 (C-1"), 138.4 (C-4), 137.4 (C-4'), 134.0 (C-2"), 131.3 (C-5"), 129.2 (×4, C-6, 8, C-6', 8'), 128.2 (×4, C-4", 6", C-5', 9'), 128.1 (C-5, 9), 127.4 (C-3", 7"), 126.5 (C-7'), 126.2 (C-7), 54.6 (C-2), 53.6 (C-2'), 36.9 (C-3), 36.7 (C-3').

Example 87

N-(N-benzoyl-4-acetamido-L-phenylalanyl)-L-phenylalanine

Spectra Data: mp 233.5-235.5° C.; ¹H-NMR (DMSO, 400 MHz): δ 9.84 (1H, s, ArNHCO), 8.46 (1H, d, J=8.4 Hz, NHCO), 7.89 (1H, d, J=8.0 Hz, NHCO), 7.79 (2H, d, J=7.6 Hz, H-3", 7"), 7.52 (1H, t, H-5"), 7.47-7.42 (4H, m, H-4", 6", 6, 8), 7.23-7.11 (7H, m, H-5'-9', 5, 9), 4.83 (1H, t, OH), 4.64 (1H, m, H-2), 3.90 (1H, m, H-2'), 3.34-3.25 (2H, m, H-1'), 3.00-2.64 (4H, m, H-3, 3'), 1.99 (3H, CH₃CO); ¹³C-NMR (DMSO, 100 MHz): δ 170.9 (C-1), 168.0 (ArNHCOCH₃), 166.0 (C-1"), 139.0 (C-7), 137.5 (C-4'), 134.1 (C-2"), 132.9 (C-4), 131.3 (C-5"), 129.4 (C-5, 9), 129.2 (C-6', 8'), 128.2 (×2), 128.1 (×2), 127.4 (C-3", 7"), 125.9 (C-7'), 118.6 (C-6 8), 62.2 (C-1'), 54.9 (C-2), 52.5 (C-2'), 36.7 (C-3'), 36.4 (C-3), 24.0 (NHCOCH₃).

Example 88

N-(N-benzoyl-4-nitro-L-phenylalanyl)-L-phenylalanine

Spectra Data: ¹H-NMR (DMSO, 400 MHz): δ 12.85 (1H, COOH), 8.54 (1H, d, J=8.8 Hz, NHCO), 8.42 (1H, d, J=8.4 Hz, NHCO), 8.14 (2H, d, J=8.8 Hz, H-6, 8), 7.77 (2H, d, J=6.8 Hz, H-3", 7"), 7.63 (2H, d, J=8.4 Hz, H-5, 9), 7.52 (1H, t, H-5"), 7.45 (2H, t, H-4", 6"), 7.26-7.18 (5H, m, H-5'-9'), 4.85 (1H, m, H-2), 4.49 (1H, m, H-2'), 3.24-2.94 (4H, m, H-3, 3'); ¹³C-NMR (DMSO, 100 MHz): δ 172.7 (C-1'), 171.0 (C-1), 166.3 (C-1'), 146.8 (C-7), 146.2 (C-4), 137.4 (C-4'), 133.8 (C-2"), 131.4 (C-5"), 130.5 (C-5, 9), 129.2 (C-6', 8'), 128.2 (×4, C-4", 6", 5', 9'), 127.4 (C-3", 7"), 126.5 (C-7'), 123.2 (C-6, 8), 53.9 (C-2'), 53.6 (C-2), 36.8, 36.6.

Example 89

N-(N-benzoyl-L-phenylalanyl)-4-acetamido-L-phenylalanine

Spectra Data: ¹H-NMR (DMSO, 400 MHz): δ 12.80 (1H, br, COOH), 9.87 (1H, s, ArNHCO), 8.55 (1H, d, J=8.4 Hz, NHCO), 8.32 (1H, d, J=8.0 Hz, NHCO), 7.75 (2H, d, J=7.2 Hz, Hi3", 7"), 7.51-7.13 (12H, m, H-4"-6", 5-9, 5', 9', 6', 8'), 4.73 (1H, m, H-2), 4.44 (1H, m, H-2'), 3.10-2.88 (4H, m, H-3, 3'), 2.02 (3H, s, COCH₃); ¹³C-NMR (DMSO, 100 MHz): δ 172.9 (C-1'), 171.6 (C-1), 168.1 (ArNHCOCH₃), 166.3 (C-1"), 138.5 (C-4), 137.9 (C-7'), 134.1 (C-2"), 131.8 (C-4'), 131.3 (C-5"), 129.4 (C-5', 9'), 129.2 (C-6, 8), 128.2 (C-4", 6"), 128.1 (C-5, 9), 127.4 (C-3", 7"), 126.3 (C-7'), 118.8 (C-6', 8'), 54.6 (C-2), 53.7 (C-2'), 37.0 (C-3), 36.1 (C-3'), 24.0 (COCH₃).

Example 90

N-(N-4-methyl-benzoyl-L-phenylalanyl)-4-acetamido-L-phenylalanine

Spectra Data: ¹H-NMR (DMSO, 400 MHz): δ 10.02 (1H, s, ArNHCO), 8.70 (1H, d, J=8.4 Hz, NHCO), 7.64 (2H, d, J=8.0 Hz, H-3", 7"), 8.49 (1H, d, J=6.4 Hz, NHCO), 7.33-7.27 (4H, m, H-6', 8', 5, 9), 7.21-7.17 (4H, m, H-4", 6", 6, 8), 7.10 (1H, t, H-7), 7.00 (2H, d, J=8.4 Hz, H-5', 9'), 4.50 (1H, m, H-2), 3.95 (1H, m, H-2'), 3.12-2.88 (4H, m, H-3, 3'), 2.29 (3H, s, Ar—CH$_3$), 1.94 (3H, s, COCH$_3$); $^{13}$C-NMR (DMSO, 100 MHz): δ 172.8 (C-1'), 170.1 (C-1), 168.0 (ArNHCO), 166.2 (C-1"), 141.1 (C-5"), 139.0 (C-4), 137.2 (C-7'), 133.6 (C-2"), 131.3 (C-4'), 129.9 (C-5', 9'), 129.1 (C-6, 8), 128.7 (C-4", 6"), 128.1 (C-5, 9), 127.5 (C-3", 7"), 126.1 (C-7), 118.5 (C-6', 8'), 55.9 (C-2'), 55.5 (C-2'), 36.9, 36.5, 23.9 (NHCOCH$_3$), 21.0 (Ar—CH$_3$).

Example 91

N-(N-4-hydroxyl-benzoyl-L-phenylalanyl)-L-phenylalanine sodium salt

Spectra Data: $^1$H-NMR (DMSO, 400 MHz): δ 8.45 (1H, d, J=8.4 Hz, NHCO), 7.62 (2H, d, J=8.4 Hz, H-3", 7"), 7.44 (1H, br, NHCO), 7.29-7.05 (10H, m, H-5-9, 5'-9'), 6.76 (3H, m, ArOH, H-4", 6"), 4.50 (1H, m, H-2), 4.02 (1H, m, H-2'), 3.11-2.92 (4H, m, H-3, 3'); $^{13}$C-NMR (DMSO, 100 MHz): δ 170.2 (C-1, 1'), 166.0 (C-1"), 160.6 (C-5"), 139.1, 139.0, 129.8 (C-3", 7"), 129.4 (C-6, 8), 129.1 (C-6', 8'), 128.1 (C-5', 9'), 127.5 (C-5, 9), 126.1 (C-7), 125.5 (C-7'), 124.5 (C-2"), 114.7 (C-4", 6"), 55.7 (C-2'), 55.4 (C-2), 37.2, 36.8.

Example 92

N-[N-4-(3-carboxyl-propionamido)-benzoyl-L-phenylalanyl]-L-phenylalanine sodium salt Spectra Data: $^1$H-NMR (DMSO, 400 MHz): δ 11.38 (1H, s, ArNHCO), 9.92 (1H, br, ArOH), 8.60 (1H, d, J=8.0 Hz, NHCO), 7.73 (2H, d, J=8.8 Hz, H-3", 7"), 7.62 (2H, d, J=8.4 Hz, H-4", 6"), 7.50 (1H, d, J=6.0 Hz, NHCO), 7.13-7.05 (7H, m, H-5-9, 5', 9'), 6.62 (2H, d, J=8.4 Hz, H-6, 8), 4.45 (1H, m, H-2), 4.04 (1H, m, H-2'), 3.14-2.79 (4H, m, H-3, 3'), 2.46 (2H, t, J=6.4 Hz, ArNHCOCH$_2$CH$_2$COONa), 2.27 (2H, t, J=6.0 Hz, ArNHCOCH$_2$CH$_2$COONa); $^3$C-NMR (DMSO, 100 MHz): δ 176.4 (COONa), 173.2, 172.7, 170.4, 165.7 (C-1"), 156.0 (C-7), 142.4 (C-5"), 139.0 (C-4'), 129.9 (C-5, 9), 129.8 (C-6', 8'), 128.5 (C-4), 128.3 (C-5', 9'), 127.9 (C-2"), 127.5 (C-3", 7"), 125.5 (C-7'), 117.8 (C-4", 6"), 115.0 (C-6, 8), 56.1 (C-2), 55.4 (C-2'), 37.3 (C-3'), 36.5 (C-3), 34.4, 33.5.

Example 93

N-(N-benzoyl-L-tyrosyl)-L-phenylalanine

Spectra Data: $^1$H-NMR (DMSO, 400 MHz): δ 12.79 (1H, br, COOH), 9.12 (1H, s, Ar—OH), 8.44 (1H, d, J=8.8 Hz, NHCO), 8.26 (1H, d, J=7.6 Hz, NHCO), 7.73 (2H, d, J=6.8 Hz, H-3", 7"), 7.48 (1H, t, H-5"), 7.41 (2H, t, H-4", 6"), 7.25-7.13 (5H, m, H-5'-9'), 7.09 (2H, d, J=8.4 Hz, H-5, 9), 6.58 (2H, d, J=8.4 Hz, H-6, 8), 4.61 (1H, m, H-2), 4.43 (1H, m, H-2'), 3.08-2.76 (4H, m, H-3, 3'); $^{13}$C-NMR (DMSO, 100 MHz): δ 172.8 (C-1'), 171.7 (C-1), 166.2 (C-1"), 155.7 (C-7), 137.4 (C-4'), 134.1 (C-2"), 131.3 (C-5"), 130.1 (C-5, 9), 129.2 (C-6', 8'), 128.4 (C-4), 128.2 (×4, C-4", 6", C-5', 9'), 127.4 (C-3", 7"), 126.5 (C-7'), 114.9 (C-6, 8), 55.0 (C-2), 53.5 (C-2'), 36.7, 36.2.

Example 94

N-(N-benzoyl-L-phenylalanyl)-4-propionamido-L-phenylalanine

Spectra Data: $^1$H-NMR (DMSO, 400 MHz): δ 12.78 (1H, br, COOH), 9.81 (1H, s, ArNHCO), 8.56 (1H, d, J=8.4 Hz, NHCO), 8.33 (1H, d, J=8.0 Hz, NHCO), 7.75 (2H, d, J=7.2 Hz, H-3", 7"), 7.50-7.48 (3H, m, H-5", 6', 8'), 7.42 (2H, t, H-4", 6"), 7.34 (2H, d, J=7.2 Hz, H-5, 9), 7.23 (2H, t, H-6, 8), 7.17-7.12 (3H, m, H-7, 5', 9'), 4.73 (1H, m, H-2), 4.44 (1H, m, H-2'), 3.10-2.86 (4H, m, H-3, 3'), 2.28 (2H, q, J=7.6 Hz, NHCOCH$_2$CH$_3$), 1.06 (3H, t, J=7.6 Hz, NHCOCH$_2$CH$_3$); $^{13}$C-NMR (DMSO, 100 MHz): δ 172.9 (C-1'), 171.9, 171.6, 166.3 (C-1"), 138.5 (C-4), 138.0 (C-7'), 134.1 (C-2"), 131.7 (C-4'), 131.3 (C-5"), 129.4 (C-5', 9'), 129.2 (C-6, 8), 128.2 (C-4", 6"), 128.1 (C-5, 9), 127.5 (C-3", 7"), 126.3 (C-7), 118.9 (C-6', 8'), 54.7 (C-2), 53.7 (C-2'), 37.0, 36.1, 29.6 (NHCOCH$_2$CH$_3$), 9.8 (NHCOCH$_2$CH$_3$).

Example 95

N-(N-benzoyl-L-tyrosyl)-4-acetamido-L-phenylalanine sodium salt

Spectra Data: $^1$H-NMR (DMSO, 400 MHz): δ 9.95 (1H, s, ArNHCO), 9.47 (1H, s, ArOH), 8.86 (1H, d, J=8.4 Hz, NHCO), 7.78-7.74 (3H, m, H-3", 7", NHCO), 7.48 (3H, m, H-6', 8', 5"), 7.34 (2H, t, H-4", 6"), 7.08 (2H, d, J=8.4 Hz, H-5, 9), 7.01 (2H, d, J=8.8 Hz, H-5', 9'), 6.61 (2H, d, J=8.4 Hz, H-6, 8), 4.44 (1H, m, H-2), 3.95 (1H, m, H-2'), 3.09-2.78 (4H, m, H-3, 3'), 1.97 (3H, CH$_3$CO); $^{13}$C-NMR (DMSO, 100 MHz): δ 172.6 (C-1'), 170.0 (C-1), 168.0 (ArNHCO), 165.3 (C-1"), 155.8 (C-7), 137.2 (C-7'), 136.0 (C-2"), 133.6 (C-4'), 132.9 (C-5"), 130.0 (C-5, 9), 129.9 (C-5', 9'), 129.4 (C-4", 6"), 128.7 (C-4), 128.3 (C-3", 7"), 118.4 (C-6', 8'), 115.0 (C-6, 8), 56.4 (C-2'), 55.5 (C-2), 36.5, 36.1, 23.9 (CH$_3$CO).

Example 96

N-(N-4-methyl-benzoyl-L-tyrosyl)-4-acetamido-L-phenylalanine

Spectra Data: $^1$H-NMR (DMSO, 400 MHz): δ 12.79 (1H, br, COOH), 9.86 (1H, s, ArNHCO), 9.14 (1H, s, Ar—OH), 8.36 (1H, d, J=8.8 Hz, NHCO), 8.23 (1H, d, J=7.6 Hz, NHCO), 7.66 (2H, d, J=8.0 Hz, H-3", 7"), 7.44 (2H, d, J=8.4 Hz, H-6', 8'), 7.23 (2H, d, J=7.6 Hz, H-4", 6"), 7.14 (2H, d, J=8.4 Hz, H-5', 9'), 7.10 (2H, d, J=8.4 Hz, H-5, 9), 6.60 (2H, d, J=8.4 Hz, H-6, 8), 4.61 (1H, m, H-2), 4.41 (1H, m, H-2'), 3.00-2.82 (4H, m, H-3, 3'), 2.32 (3H, s, Ar—CH$_3$), 2.01 (3H, s, COCH$_3$); $^{13}$C-NMR (DMSO, 100 MHz): δ 172.8 (C-1'), 171.7 (C-1), 168.1 (ArNHCO), 166.0 (C-1"), 155.7 (C-7), 141.2 (C-5"), 137.8 (C-7'), 131.8 (C-4'), 131.3 (C-2"), 130.1 (C-5, 9), 129.4 (C-5', 9'), 128.7 (C-4", 6"), 128.5 (C-4), 127.4 (C-3", 7"), 118.8 (C-6', 8'), 114.8 (C-6, 8), 55.0 (C-2), 53.6 (C-2'), 52.1 (OCH$_3$), 36.2 (t×2), 24.0 (COCH$_3$), 21.0 (Ar—CH$_3$).

Example 97

N-(N-4-chloro-benzoyl-L-phenylalanyl)-L-phenylalanine

Spectra Data: $^1$H-NMR (DMSO, 400 MHz): δ 12.83 (1H, br, COOH), 8.67 (1H, d, J=8.4 Hz, NHCO), 8.39 (1H, d, J=8.0 Hz, NHCO), 7.79 (2H, d, J=8.8 Hz, H-3", 7"), 7.53 (2H, m, H-4", 6"), 7.34-7.13 (10H, m, H-5-9, 5'-9'), 4.75 (1H, m, H-2), 4.48 (1H, m, H-2'), 3.13-2.88 (4H, m, H-3, 3'); $^{13}$C-NMR (DMSO, 100 MHz): δ 172.8 (C-1'), 171.5 (C-1), 165.1 (C-1"), 138.4 (C-4), 137.4 (C-4'), 136.2 (C-5"), 132.7 (C-2"), 129.4 (×2), 129.2 (×4), 128.3 (×2), 128.2 (×2), 128.1 (×2), 126.5, 126.3, 54.6 (C-2), 53.6 (C-2'), 36.9, 36.6.

Example 98

N-(N-4-chloro-benzoyl-L-phenylalanyl)-L-phenylalanine sodium salt

Spectra Data: $^1$H-NMR (DMSO, 400 MHz): δ 8.92 (1H, br, NHCO), 7.79 (2H, d, J=8.8 Hz, H-3", 7"), 7.51 (3H, m, H-4", 6", NHCO), 7.31-7.05 (10H, m, H-5-9, 5'-9'), 4.52 (1H, m, H-2), 3.90 (1H, m, H-2'), 3.13-3.09 (2H, m, H-3), 2.98-2.89 (2H, m, H-3'); $^{13}$C-NMR (DMSO, 100 MHz): δ 179.0 (C-1'), 169.7 (C-1), 165.1 (C-1"), 139.3 (C-4), 138.8 (C-4'), 136.0 (C-5"), 132.8 (C-2"), 129.8 (×2), 129.4 (×2), 129.1 (×2), 128.2 (×2), 128.1 (×2), 127.4 (×2), 126.1, 125.4, 55.9 (C-2), 55.5 (C-2'), 37.2, 36.8.

Example 99

N-(N-2-chloro-benzoyl-L-phenylalanyl)-L-phenylalanine

Spectra Data: $^1$H-NMR (DMSO, 400 MHz): δ 12.82 (1H, br, COOH), 8.56 (1H, d, J=8.4 Hz, NHCO), 8.23 (1H, d, J=7.6 Hz, NHCO), 7.43-7.12 (14H, m, H-5-9, 4"-7", 5'-9'), 4.74 (1H, m, H-2), 4.52 (1H, m, H-2'), 3.14-2.78 (4H, m, H-3, 3'); $^{13}$C-NMR (DMSO, 100 MHz): δ 172.6 (C-1'), 170.9 (C-1), 165.9 (C-1"), 137.8 (C-4), 137.3 (C-4'), 136.4 (C-5"), 130.7 (C-3"), 129.9 (C-2"), 129.5 (C-4'), 129.21 (C-6', 8'), 129.17 (C-6, 8), 128.8 (C-7"), 128.2 (C-5, 9), 128.0 (C-5', 9'), 126.8 (C-6"), 126.5 (C-7), 126.2 (C-7'), 54.1, 53.5, 37.2, 36.8.

Example 100

N-(N-4-nitro-benzoyl-L-tyrosyl)-L-phenylalanine

Spectra Data: $^1$H-NMR (DMSO, 400 MHz): δ 9.19 (1H, br, Ar—OH), 8.90 (1H, d, J=8.8 Hz, NHCO), 8.42 (1H, d, J=7.6 Hz, NHCO), 8.30 (2H, d, J=8.8 Hz, H-4", 6"), 7.99 (2H, d, J=8.8 Hz, H-3", 7"), 7.27-7.18 (5H, m, H-5'-9'), 7.13 (2H, d, J=8.4 Hz, H-5, 9), 6.63 (2H, d, J=8.4 Hz, H-6, 8), 4.70 (1H, m, H-2), 4.47 (1H, m, H-2'), 3.14-2.80 (4H, m, H-3, 3'); $^{13}$C-NMR (DMSO, 100 MHz): δ 172.9 (C-1'), 171.4 (C-1), 164.5 (C-1"), 155.8 (C-7), 149.1 (C-5"), 139.7 (C-2"), 137.6 (C-4'), 130.1 (C-5, 9), 129.2 (C-6', 8'), 128.9 (C-3", 7"), 128.2 (C-5', 9'), 128.2 (C-4), 126.5 (C-7'), 123.5 (C-4", 6"), 114.9 (C-6, 8), 55.2 (C-2), 53.7 (C-2'), 36.6, 36.3.

Example 101

N-(N-4-acetamido-benzoyl-L-phenylalanyl)-L-phenylalanine

Spectra Data: $^1$H-NMR (DMSO, 400 MHz): δ 12.82 (1H, br, COOH), 10.16 (1H, s, ArNHCO), 8.42 (1H, d, J=8.4 Hz, NHCO), 8.32 (1H, d, J=8.0 Hz, NHCO), 7.73 (2H, d, J=8.8 Hz, H-3", 7"), 7.62 (2H, d, J=8.8 Hz, H-4", 6"), 7.34-7.14 (10H, m, H-5-9, 6'-9'), 4.72 (1H, m, H-2), 4.47 (1H, m, H-2'), 3.12-2.91 (4H, m, H-3, 3'), 2.06 (3H, CH$_3$CO); $^{13}$C-NMR (DMSO, 100 MHz): δ 172.8 (C-1'), 171.6 (C-1), 168.7 (ArNHCO), 165.7 (C-1"), 142.0 (C-5"), 138.5 (C-4), 137.4 (C-4'), 129.4 (C-6, 8), 129.2 (C-6', 8'), 128.3 (C-3", 7"), 128.2 (C-2"), 128.2 (C-5', 9'), 128.1 (C-5, 9), 126.5 (C-7'), 126.2 (C-7), 117.9 (C-4", 6"), 54.5 (C-2), 53.6 (C-2'), 36.9 (C-3), 36.7 (C-3'), 24.1 (CH$_3$CO).

Example 102

N-(N-isonicotinyl-L-phenylalanyl)-L-tyrosine

Spectra Data: $^1$H-NMR (DMSO, 400 MHz): δ 12.78 (1H, br, COOH), 9.23 (1H, s, Ar—OH), 8.89 (1H, d, J=8.8 Hz, NHCO), 8.70 (2H, m, H-4", 6"), 8.36 (1H, d, J=8.0 Hz, NHCO), 7.65 (2H, d, J=5.2 Hz, H-3", 7"), 7.34 (2H, d, J=6.8 Hz, H-5, 9), 7.25 (2H, t, H-6, 8), 7.16 (1H, t, H-7), 7.03 (2H, d, J=8.4 Hz, H-5', 9'), 6.62 (2H, d, J=8.0 Hz, H-6', 8'), 4.77 (1H, m, H-2), 4.38 (1H, m, H-2'), 3.13-2.82 (4H, m, H-3, 3'); $^{13}$C-NMR (DMSO, 100 MHz): δ 172.9 (C-1'), 171.1 (C-1), 164.7 (C-1"), 156.0 (C-7'), 150.2 (C-4", 6"), 140.9 (C-2"), 138.2 (C-4), 130.1 (C-5', 9'), 129.2 (C-6, 8), 128.1 (C-5, 9), 127.4 (C-4'), 126.3 (C-7), 121.4 (C-3", 7"), 115.0 (C-6', 8'), 54.6 (C-2), 54.0 (C-2'), 37.0 (C-3), 35.8 (C-3').

Example 103

N-(N-4-acetamido-benzoyl-L-phenylalanyl)-L-tyrosine

Spectra Data: $^1$H-NMR (DMSO, 400 MHz): δ 12.77 (1H, br, COOH), 10.18 (1H, s, ArNHCO), 9.23 (1H, s, ArOH), 8.43 (1H, d, J=8.4 Hz, NHCO), 8.24 (1H, d, J=7.6 Hz, NHCO), 7.73 (2H, d, J=8.8 Hz, H-3", 7"), 7.63 (2H, d, J=8.8 Hz, H-4", 6"), 7.34 (2H, d, J=7.2 Hz, H-5, 9), 7.24 (2H, t, H-6, 8), 7.15 (1H, t, H-7), 7.02 (2H, d, J=8.4 Hz, H-5', 9'), 6.61 (2H, d, J=8.8 Hz, H-6', 8'), 4.72 (1H, m, H-2), 4.39 (1H, m, H-2'), 3.10-2.84 (4H, m, H-3, 3'), 2.07 (3H, CH$_3$CO); $^{13}$C-NMR (DMSO, 100 MHz): δ 172.9 (C-1'), 171.5 (C-1), 168.7 (ArNHCO), 165.7 (C-1"), 156.0 (C-7'), 142.0 (C-5"), 138.5 (C-4), 130.1 (C-5', 9'), 129.2 (C-6, 8), 128.3 (C-3", 7"), 128.2 (C-4'), 128.0 (C-5, 9), 127.3 (C-2"), 126.2 (C-7), 118.0 (C-4", 6"), 115.0 (C-6', 8'), 54.5 (C-2), 53.9 (C-2'), 36.9 (C-3), 36.0 (C-3'), 24.1 (CH$_3$CO).

Example 104

N-(N-4-propionamido-benzoyl-L-phenylalanyl)-L-phenylalanine

Spectra Data: $^1$H-NMR (DMSO, 400 MHz): δ 12.81 (1H, br, COOH), 10.09 (1H, s, ArNHCO), 8.40 (1H, d, J=8.4 Hz, NHCO), 8.31 (1H, d, J=7.6 Hz, NHCO), 7.73 (2H, d, J=9.2 Hz, H-3", 7"), 7.63 (2H, d, J=8.8 Hz, H-4", 6"), 7.34-7.13 (10H, m, H-5-9, 5'-9'), 4.72 (1H, m, H-2), 4.48 (1H m, H-2'), 3.11-3.05 (2H, m, H-3), 2.99-2.91 (2H, m, H-3'), 2.34 (2H, q, J=7.6 Hz, COCH$_2$CH$_3$), 1.08 (3H, t, J=7.6 Hz, COCH$_2$CH$_3$); $^{13}$C-NMR (DMSO, 100 MHz): δ 172.8 (C-1'), 172.4, 171.6, 165.7 (C-1"), 142.1 (C-5"), 138.5 (C-4), 137.4 (C-4'), 129.2 (×4, C-6, 8, 6', 8'), 128.3 (C-3", 7"), 128.2 (C-5', 9'), 128.1 (C-2"), 128.0 (C-5, 9), 126.5 (C-7), 126.2 (C-7'), 118.0 (C-4", 6"), 54.5 (C-2), 53.5 (C-2'), 36.9 (C-3), 36.6 (C-3'), 29.6 (COCH$_2$CH$_3$), 9.5 (COCH$_2$CH$_3$).

Example 105

N-(N-4-acetamido-benzoyl-L-tyrosyl)-L-phenylalanine

Spectra Data: $^1$H-NMR (DMSO, 400 MHz): δ 12.79 (1H, br, COOH), 10.16 (1H, s, ArNHCO), 9.14 (1H, s, ArOH), 8.32 (1H, d, J=8.8 Hz, NHCO), 8.27 (1H, d, J=7.6 Hz, NHCO), 7.73 (2H, d, J=8.4 Hz, H-3", 7"), 7.62 (2H, d, J=8.4 Hz, H-4", 6"), 7.25-7.17 (5H, m, H-5'-9'), 7.11 (2H, d, J=8.4 Hz, H-5, 9), 6.61 (2H, d, J=8.8 Hz, H-6, 8), 4.62 (1H, m, H-2), 4.46 (1H, m, H-2'), 3.11-2.73 (4H, m, H-3, 3'), 2.07 (3H, CH$_3$CO); $^{13}$C-NMR (DMSO, 100 MHz): δ 172.8 (C-1'), 171.8 (C-1), 168.7 (ArNHCO), 165.6 (C-1"), 155.7 (C-7), 142.0 (C-5"), 137.4 (C-4'), 130.1 (C-5, 9), 129.2 (6', 8'), 128.4 (C-4, 2"), 128.3 (C-3", 7"), 128.2 (C-5', 9'), 126.5 (C-7'), 117.9 (C-4", 6"), 114.8 (C-6, 8), 54.9 (C-2), 53.5 (C-2'), 36.7, 36.2, 24.2 (CH$_3$CO).

Example 106

N-(N-isonicotinyl-L-tyrosyl)-4-nitro-L-phenylalanine

Spectra Data: $^1$H-NMR (DMSO, 400 MHz): δ 12.96 (1H, br, COOH), 9.17 (1H, s, ArOH), 8.79 (1H, d, J=8.4 Hz, NHCO), 8.69 (2H, d, J=5.6 Hz, H-4", 6"), 8.50 (1H, d, J=8.4 Hz, NHCO), 8.08 (2H, d, J=8.8 Hz, H-6', 8'), 7.65 (2H, m, H-3", 7"), 7.52 (2H, d, J=8.4 Hz, H-5', 9'), 7.11 (2H, d, J=8.8 Hz, H-5, 9), 6.62 (2H, d, J=8.4 Hz, H-6, 8), 4.67-4.54 (2H, m, H-2, 2'), 3.26 (1H, dd, J=5.2, 13.6 Hz, H-3'a), 3.08 (1H, dd, J=9.2, 13.6 Hz, H-3'b), 2.98-2.73 (2H, m, H-3); $^{13}$C-NMR (DMSO, 100 MHz): δ 172.4 (C-1'), 171.3 (C-1), 164.5 (C-1"), 155.8 (C-7), 150.2 (C-4", 6"), 146.2 (C-7'), 145.9 (C-4'), 140.9 (C-2"), 130.6 (C-5', 9'), 130.1 (C-5, 9), 128.1 (C-4), 123.2 (C-6', 8'), 121.3 (C-3", 7"), 114.9 (C-6, 8), 55.0 (C-2), 52.9 (C-2'), 36.3, 36.1.

C. Biological Activity Tests of Some Derivatives
1. In Vitro Tests
   Test Principle:
   2.2.15 cells were used as a vector of hepatitis B virus. Samples were assayed for their abilities to inhibit NBV to carry out DNA replication and to produce HBsAg and HBeAg.
   Test Materials and Method:
   a. cell line: 2.2.15 cells;
   b. treatment of samples: A sample was dissolved in DMSO in a suitable concentration right before use. The resulting solution was diluted in triple folds with culture media. There are eight dilutions.
   c. positive control: Lamivudine (3TC) produced by Glaxo Wellcome;
   d. reagents: radioimmunological kits of e antigen and s antigen of hepatitis B virus, α$^{32}$PdCTP;
   e. test method: 2.2.15 cells were seeded in a 96-well microplate. After 36 hours, samples and positive controls in the above dilutions were added into the wells. Cell control wells were simultaneously set up. Culture media were replaced with fresh culture media containing samples in different dilutions, respectively, after 96 hours of addition of samples and positive controls. At the eighth day of addition of samples and positive controls, cell supernatants and 2.2.15 cells were harvested, respectively. Secretory volumes of HBsAg and HBeAg in the cell supernatants were assayed with the RIA method. The degree of HBV DNA replication in the cells was assayed with dot blot method. IC$_{50}$ and SI were calculated, respectively.
The test results are listed in Table 1.

TABLE 1

Test Results of In Vitro Anti-HBV Activities of Some Derivatives

| Compound | TC$_{50}$ (µg/ml) | Inhibition of HBsAg | | Inhibition of HBeAg | | Inhibition of DNA Replication | |
|---|---|---|---|---|---|---|---|
| | | IC$_{50}$ (µg/ml) | SI | IC$_{50}$ (µg/ml) | SI | IC$_{50}$ (µg/ml) | SI |
| Example 01 | 1101.11 | — | — | — | — | — | — |
| Example 02 | 231.12 | — | — | — | — | — | — |
| Example 03 | 17.81 | — | — | — | — | 0.63 | 28.27 |
| Example 04 | 450.67 | — | — | — | — | 51.78 | 8.70 |
| Example 05 | 77.04 | — | — | — | — | 25.19 | 3.06 |
| Example 06 | 53.42 | — | — | — | — | — | — |
| Example 07 | 28.74 | — | — | — | — | 1.02 | 28.29 |
| Example 08 | 166.70 | — | — | — | — | — | — |
| Example 09 | 240.38 | — | — | — | — | — | — |
| Example 10 | 288.68 | — | — | — | — | — | — |
| Example 11 | 500.00 | — | — | — | — | — | — |
| Example 12 | 388.03 | — | — | — | — | — | — |
| Example 13 | 776.06 | — | — | — | — | — | — |
| Example 14 | 53.42 | — | — | — | — | 1.16 | 45.93 |
| Example 15 | 45.69 | — | — | — | — | — | — |
| Example 16 | 52.34 | — | — | — | — | — | — |
| Example 17 | 465.23 | — | — | — | — | — | — |
| Example 18 | 45.28 | — | — | — | — | — | — |
| Example 19 | 587.06 | — | — | — | — | 103.25 | 5.69 |
| Example 20 | 198.46 | — | — | — | — | 48.50 | 4.09 |
| Example 21 | 28.74 | — | — | — | — | — | — |
| Example 22 | 346.68 | — | — | — | — | 105.88 | 3.27 |
| Example 23 | 240.38 | — | — | — | — | 52.00 | 4.62 |
| Example 24 | 396.81 | — | — | — | — | 95.98 | 4.13 |
| Example 25 | 574.76 | — | — | — | — | 68.70 | 8.37 |
| Example 26 | 472.10 | — | — | — | — | — | — |
| Example 27 | 441.29 | — | — | — | — | — | — |
| Example 27 | 456.75 | — | — | — | — | — | — |
| Example 36 | 388.03 | — | — | — | — | 4.56 | 85.09 |
| Example 37 | 129.34 | — | — | — | — | 1.43 | 90.45 |
| Example 38 | 80.13 | — | — | — | — | 2.39 | 33.53 |
| Example 39 | 14.37 | — | — | — | — | 0.34 | 42.26 |

TABLE 1-continued

Test Results of In Vitro Anti-HBV Activities of Some Derivatives

| Compound | $TC_{50}$ (μg/ml) | Inhibition of HBsAg $IC_{50}$ (μg/ml) | SI | Inhibition of HBeAg $IC_{50}$ (μg/ml) | SI | Inhibition of DNA Replication $IC_{50}$ (μg/ml) | SI |
|---|---|---|---|---|---|---|---|
| Example 43 | 86.23 | — | — | — | — | 11.67 | 7.39 |
| Example 46 | 388.03 | — | — | — | — | 2.41 | 161.01 |
| Example 47 | 256.78 | — | — | — | — | — | — |
| Example 49 | 86.23 | — | — | — | — | 7.28 | 11.84 |
| Example 50 | 64.15 | — | — | — | — | 7.04 | 9.11 |
| Example 51 | 78.52 | — | — | — | — | 6.98 | 11.25 |
| Example 52 | 89.23 | — | — | — | — | 24.20 | 3.69 |
| Example 53 | 354.18 | — | — | — | — | — | — |
| Example 54 | 43.11 | — | — | — | — | 0.82 | 52.57 |
| Example 55 | 53.42 | — | — | — | — | 4.96 | 10.78 |
| Example 56 | 333.33 | — | — | — | — | — | — |
| Example 57 | 451.20 | — | — | — | — | 59.48 | 7.59 |
| Example 58 | 28.74 | — | — | — | — | — | — |
| Example 59 | 258.69 | — | — | — | — | — | — |
| Example 63 | 358.02 | — | — | — | — | 53.12 | 6.74 |
| Example 64 | 58.54 | — | — | — | — | — | — |
| Example 68 | 388.03 | — | — | — | — | 13.12 | 29.57 |
| Example 69 | 75.46 | — | — | — | — | — | — |
| Example 70 | 17.81 | — | — | — | — | — | — |
| Example 71 | 388.03 | — | — | — | — | 6.62 | 58.61 |
| Example 72 | 577.35 | — | — | — | — | 87.50 | 6.60 |
| Example 74 | >500 | 25.19 | 19.85 | — | — | 32.96 | >15.2 |
| Example 75 | 388.03 | 33.51 | 11.58 | 13.51 | 28.72 | 2.41 | 58.60 |
| Example 76 | 37.04 | — | — | — | — | — | — |
| Example 77 | 160.25 | — | — | — | — | 13.51 | 11.86 |
| Example 78 | 257.31 | — | — | — | — | 54.28 | 4.74 |
| Example 79 | 86.23 | — | — | — | — | 9.59 | 8.99 |
| Example 80 | 388.03 | 150.20 | 2.58 | — | — | 27.28 | 14.22 |
| Example 81 | 58.64 | — | — | — | — | — | — |
| Example 82 | 59.19 | — | — | — | — | — | — |
| Example 83 | >1000 | — | — | — | — | 252.60 | >3.96 |
| Example 84 | 86.23 | — | — | — | — | 1.44 | 59.97 |
| Example 86 | 130.56 | — | — | — | — | 10.56 | 12.36 |
| Example 87 | 43.11 | — | — | — | — | 1.81 | 23.82 |
| Example 88 | 388.03 | — | — | — | — | 25.00 | 15.52 |
| Example 92 | 379.36 | — | — | — | — | — | — |
| Example 93 | 577.35 | — | — | — | — | — | — |
| Example 94 | 561.21 | — | — | — | — | — | — |
| Example 95 | 79.46 | — | — | — | — | — | — |
| Example 96 | 199.67 | — | — | — | — | — | — |
| 3TC | 786.00 | — | — | — | — | 18.90 | 41.59 | wherein:
$TC_{50}$—median toxic concentration;
$IC_{50}$—50% inhibiting concentration; and
SI—stimulation index 2. In Vivo Tests Test compounds: the compound prepared in Example 75

Test method: One-day-old ducklings were infected with serum containing DHBV positive virus (about $10^{8-9}$ virions/ml). After a week, blood was collected and tested. The successfully transfected ducklings were randomly divided into three to five groups. Blank group, positive control group and treatment group(s) (one to three groups) were subjected to treatment tests. The treatment groups were divided into high, median and low dose groups. Intraperitoneal injection was carried out daily for ten days. Physiological saline was used to replace drugs in the blank group. Lamivudine was administered in the positive control group. Blood was collected before the administration, at the fifth day and tenth day of the administration and at the fifth day of the drug withdrawal. Serum was separated and kept at −70° C. for tests. Duck hepatitis B virus surface antigen (DHBsAg) was assayed with DHBsAg dot molecular hybridization (DOT EIA). Duck hepatitis B virus deoxyribonucleic acid (DHBV DNA) contents in serum and duck livers were assayed with dot blot hybridization.

The test results are listed in Table 2.

TABLE 2

In Vivo Inhibition Action and Effects of Test Compounds on DHBV-DNA in ducklings

| Group | $5^{th}$ Day of Test OD Value | Inhibition Ratio | $10^{th}$ Day of Test OD Value | Inhibition Ratio | $3^{rd}$ Day of Withdrawal OD Value | Inhibition Ratio |
|---|---|---|---|---|---|---|
| DHBV | 1.33 | | 1.09 | | 1.08 | |
| Example 75 (12.5 mg/kg) | 1.11 | 12.87 | $1.11^a$ | $12.92^a$ | 1.09 | 9.23 |
| Example 75 (25.0 mg/kg) | $1.15^a$ | $18.67^c$ | $0.95^b$ | $32.91^d$ | $0.87^b$ | $38.12^d$ |
| Example 75 (50.0 mg/kg) | $0.94^a$ | $36.43^c$ | $0.73^b$ | $54.62^d$ | $0.83^b$ | $42.30^d$ |

TABLE 2-continued

In Vivo Inhibition Action and Effects of Test Compounds on DHBV-DNA in ducklings

| Group | 5th Day of Test | | 10th Day of Test | | 3rd Day of Withdrawal | |
|---|---|---|---|---|---|---|
| | OD Value | Inhibition Ratio | OD Value | Inhibition Ratio | OD Value | Inhibition Ratio |
| 3TC (50.0 mg/kg) | $0.73^b$ | $53.71^d$ | $0.68^b$ | $57.22^d$ | 1.54 | 0.3 |

Note:
self (pairing) comparison:
[a] $p < 0.05$;
[b] $p < 0.01$;
intergroup (group) comparison:
[c] $p < 0.05$;
[d] $p < 0.01$ From the foregoing it will be appreciated that, although specific preferred embodiments and examples of the invention have been described herein for the purposes of illustration, various modifications and replacements may be made without deviating from the spirit and scope of the invention. Accordingly, the invention is not limited except as by the appended claims.

What is claimed is:

1. A compound of formula I and pharmaceutically acceptable salts thereof,

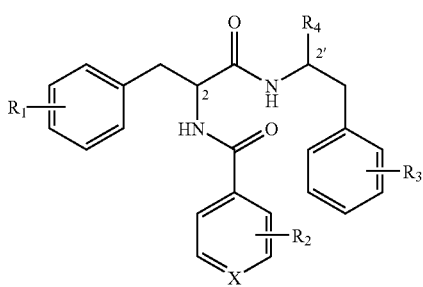

wherein,
each $R_1$, $R_2$ and $R_3$ independently represent a single substituent, wherein $R_1$ is independently selected from the group consisting of H, $NO_2$, $NH_2$, NRR', NHCOR, $NHCO(CH_2)_nCOOH$, OH, OCOR, OR and $O(CH_2)_nNRR'$;
$R_3$ is selected from the group consisting of H, $NO_2$, $NH_2$, NRR', NHCOR, $NHCO(CH_2)_nCOOH$, and $CH_2NRR'$;
$R_2$ is selected from the group consisting of H, $NO_2$, $NH_2$, NRR', NHCOR, $NHCO(CH_2)_nCOOH$, $NHOC(CH_2)_nNRR'$; OH, OCOR, OR, $O(CH_2)_nNRR'$, $O(CH_2)_nCOOH$, CN, $CH_2NRR'$, COOH, $C_1$-$C_6$ alkyl, halo, (1-pyrrolidyl) acetamido,

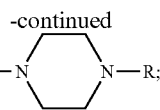

$R_4$ is selected from the group consisting of $CH_2OH$, COOR, $CH_2OCOC_2$-$C_6$ (linear or branched alkyl), $CH_2OCOC_3$-$C_7$ cycloalkyl, $CH_2OCO(CH_2)_nCOOH$, COONa and —COOH;
each R and R' in the $R_1$ to $R_4$ described above represent identical or different, linear or branched $C_1$-$C_6$ alkyl or $C_3$-$C_7$ cycloalkyl;
said alkyl and cycloalkyl may be further optionally substituted with one or two substituents selected from the group consisting of OH, $NO_2$, CN, $CF_3$ and halo;
X is CH or N; and
n is an integral number of 1 to 4;
with the proviso that the following compounds are excluded where:
X is CH, $R_1$ is $CH_2N(CH_3)_2$, $R_2$ is H, $R_3$ is H, and $R_4$ is $CH_2OH$ or $CH_2OCOMe$;
X is CH, $R_1$ is H, $R_2$ is $NHCH_2CH_2N(CH_3)_2$, $R_3$ is H, and $R_4$ is $CH_2OH$ or $CH_2OCOMe$;
X is CH, $R_1$ is H, $R_2$ is H, $R_3$ is $CH_2N(CH_3)_2$, and $R_4$ is $CH_2OH$ or $CH_2OCOMe$;
X is CH, each $R_1$, $R_2$ and $R_3$ are H, and $R_4$ is $CH_2OH$.

2. The compound of claim 1, wherein $R_2$ is selected from the group consisting of H, $NO_2$, NHCOR, $NHCO(CH_2)_n$ COOH, OH, OCOR, $O(CH_2)_nNRR'$, $CH_2NRR'$, $C_1$-$C_6$ alkyl, halo, (1-pyrrolidyl) acetamido,

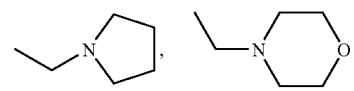

and COOH.

3. The compound of claim 1, wherein $R_1$ is selected from the group consisting of H, $NO_2$, $NHCOCH_3$, $NHCOCH2CH3$, $N(CH_3)_2$, $NHCO(CH_2)_2COOH$, OH, $OCH_3$, $OCOCH_3$, $O(CH_2)_2N(CH_3)_2$ and $OCH_2COOH$.

4. The compound of claim 1, wherein $R_3$ is selected from the group consisting of H, $NO_2$, $NHCOCH_3$, and $NHCOCH_2CH_3$.

5. The compound of claim 1, wherein $R_2$ is selected from the group consisting of H, F, Cl, $NO_2$, $NHCOCH_3$, $NHCOCH_2Cl$, $NHCOCH_2CH_3$, $NHCO(CH_2)_2COOH$, $NHCOCH_2N(CH_3)_2$, OH, $OCOCH_2CH_3$, $O(CH_2)_2N(CH_3)_2$, $CH_3$, $CH_2N(CH_3)_2$, COOH, (1-pyrrolidyl)acetamido,

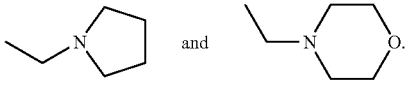

6. The compound of claim 1, wherein $R_4$ is selected from the group consisting of $CH_2OH$, $COOCH_3$, $CH_2OCOCH_3$, $CH_2OCOCH_2CH_3$, $CH_2OCOCH_2COOH$, $CH_2OCO(CH_2)_2COOH$, COONa and COOH.

7. A pharmaceutical composition, comprising a therapeutically effective amount of a compound of claim 1, or a pharmaceutically acceptable salt thereof, and a pharmaceutically acceptable carrier.

* * * * *